United States Patent
Yasuhara et al.

(10) Patent No.: US 8,039,647 B2
(45) Date of Patent: Oct. 18, 2011

(54) 2-AMINO-BICYCLO (3.1.0) HEXANE-2,6-DICARBOXYLIC ESTER DERIVATIVE

(75) Inventors: Akito Yasuhara, Toshima-ku (JP); Kazunari Sakagami, Toshima-ku (JP); Hiroshi Ohta, Toshima-ku (JP); Atsuro Nakazato, Toshima-ku (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/511,482

(22) Filed: Jul. 29, 2009

(65) Prior Publication Data

US 2009/0306408 A1 Dec. 10, 2009

Related U.S. Application Data

(62) Division of application No. 10/562,018, filed as application No. PCT/JP2004/009398 on Jun. 25, 2004.

(30) Foreign Application Priority Data

Jun. 26, 2003 (JP) ................. 2003-181930
Oct. 31, 2003 (JP) ................. 2003-373511
Apr. 23, 2004 (JP) ................. 2004-128663

(51) Int. Cl.
*C07D 317/08* (2006.01)
(52) U.S. Cl. .................................. 549/229
(58) Field of Classification Search ............. 549/229
See application file for complete search history.

(56) References Cited

U.S. PATENT DOCUMENTS

| 5,750,566 A | 5/1998 | Monn et al. |
| 2006/0142388 A1 | 6/2006 | Yasuhara et al. |

FOREIGN PATENT DOCUMENTS

| EP | 1295865 A1 | 3/2003 |
| EP | 1459765 A1 | 9/2004 |
| GB | 2341179 A | 3/2000 |
| JP | 2000-500754 A | 1/2000 |
| JP | 2000-086597 A | 3/2000 |
| JP | 2000-336071 A | 12/2000 |
| JP | 2001-525825 A | 12/2001 |
| WO | 02/00605 A1 | 1/2002 |
| WO | 02/068380 A1 | 9/2002 |
| WO | 03/061698 A1 | 7/2003 |
| WO | 2005/000789 A1 | 1/2005 |
| WO | 2005/000790 A1 | 1/2005 |

OTHER PUBLICATIONS

Camille G. Wermuth, The Practice of Medicinal Chemistry: Second Edition, 2003, Elsevier Academic Press, pp. 561-585.
B.J.R. Nicolaus, "Symbiotic Approach to Drug Design", Decision making in Drug Research, 1983, pp. 173-186.

*Primary Examiner* — Victor Oh
(74) *Attorney, Agent, or Firm* — Sughrue Mion, PLLC

(57) ABSTRACT

A drug effective for the treatment and prevention of psychiatric disorders such as schizophrenia, anxiety and related ailments thereof, depression, bipolar disorder and epilepsy. The drug antagonizes the action of group II metabotropic glutamate receptors and shows high activity in oral administration A 2-amino-bicyclo[3.1.0]hexane-2,6-dicarboxylic ester derivative represented by formula [I]

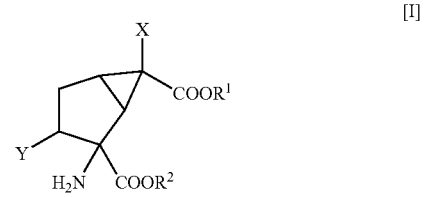

[wherein $R^1$ and $R^2$ are identical or different, and each represents a hydrogen atom, a $C_{1-10}$alkyl group or the like; X represents a hydrogen atom or a fluorine atom; Y represents —OCHR³R⁴ or the like (wherein $R^3$ and $R^4$ are identical or different, and each represents a hydrogen atom, a $C_{1-10}$alkyl group or the like; and n represents integer 1 or 2)], a pharmaceutically acceptable salt thereof or a hydrate thereof.

6 Claims, No Drawings

2-AMINO-BICYCLO (3.1.0) HEXANE-2,6-DICARBOXYLIC ESTER DERIVATIVE

CROSS-REFERENCE TO RELATED APPLICATIONS

This is a divisional of U.S. patent application Ser. No. 10/562,018 filed Jun. 30, 2006, which is a National Stage Application filed under §371 of PCT Application No. PCT/JP2004/009398 filed Jun. 25, 2004. The entire disclosures of the prior applications, U.S. patent application Ser. No. 10/562,018 and PCT/JP2004/009398 are hereby incorporated by reference.

FIELD OF THE INVENTION

The present invention relates to a pharmaceutically effective 2-amino-bicyclo[3.1.0]hexane-2,6-dicarboxylic ester derivative, a pharmaceutically acceptable salt thereof, a hydrate thereof or a prodrug containing the above as an active ingredient. More specifically, the present invention relates to a prodrug of 2-amino-bicyclo[3.1.0]hexane-2,6-dicarboxylic acid derivative and so on that are a compound that acts as an antagonist of mGlu2/mGluR3 belonging to sub group II of metabolic (metabotropic) glutamate receptors (mGluR), which is effective for the treatment and prevention of psychiatric disorders such as schizophrenia, anxiety and related ailments thereof, depression, bipolar disorder and epilepsy; and also of neurological diseases such as drug dependence, cognitive disorders, Alzheimer's disease, Huntington's chorea, Parkinson's disease, dyskinesia associated with muscular rigidity, cerebral ischemia, cerebral failure, myelopathy and head trauma.

Further, the present invention relates to the finding that a prodrug of a compound that acts as an antagonist of mGluR2/mGluR3 shows high activity in oral administration and increases the amount of exposure in vivo of the parent compound.

BACKGROUND OF THE INVENTION

Metabotropic glutamate receptors are classified pharmacologically into three groups. Of these, group II (mGluR2/mGluR3) bind with adenylcyclase, and inhibit the accumulation of the Forskolin stimulation of cyclic adenosine monophosphate (cAMP) (see Trends Pharmacol. Sci., 14, 13, 1993 (non-patent document 1 mentioned below)). Thus it is suggested that compounds that antagonize the action of group II metabotropic glutamate receptors are effective for the treatment and prevention of acute and chronic psychiatric disorders and neurological diseases. A 2-amino-bicyclo[3.1.0] hexane-2,6-dicarboxylic acid derivative is a compound that has a strong antagonistic effect on group II metabotropic glutamate receptors.

LIST OF RELATED DOCUMENTS

Non-Patent Document 1
Trends Pharmacol. Sci., 14, 13, 1993

It is an object of the present invention to provide a drug that is effective for the treatment and prevention of psychiatric disorders such as schizophrenia, anxiety and related ailments thereof, depression, bipolar disorder and epilepsy; and also effective for the treatment and prevention of neurological diseases such as drug dependence, cognitive disorders, Alzheimer's disease, Huntington's chorea, Parkinson's disease, dyskinesia associated with muscular rigidity, cerebral ischemia, cerebral failure, myelopathy and head trauma; which is a drug that antagonizes the action of group II metabotropic glutamate receptors and shows high activity in oral administration.

DISCLOSURE OF THE INVENTION

The present inventors have conducted extensive examinations into 2-amino-bicyclo[3.1.0]hexane-2,6-dicarboxylic ester derivatives, and by conducting animal tests with a parent compound as the test drug, discovered that a prodrug of a 2-amino-bicyclo[3.1.0]hexane-2,6-dicarboxylic acid derivative that affects group II metabotropic glutamate receptors increases the amount of exposure in vivo of the parent compound, thereby completing the present invention.

The present invention provides a 2-amino-bicyclo[3.1.0] hexane-2,6-dicarboxylic ester derivative, (hereinafter may be referred to as 'the compound of the present invention'), a pharmaceutically acceptable salt thereof or a hydrate thereof, represented by formula [I]

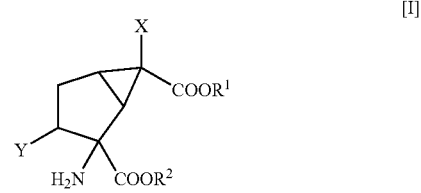

[wherein,
$R^1$ and $R^2$ are identical or different, and each represents a $C_{1\text{-}10}$alkyl group, a $C_{2\text{-}10}$alkenyl group, a $C_{2\text{-}10}$alkynyl group, a $C_{1\text{-}10}$alkyl group substituted by one or two aryl groups, a hydroxy$C_{2\text{-}10}$alkyl group, a halogeno$C_{1\text{-}10}$alkyl group, an azido$C_{1\text{-}10}$alkyl group, an amino$C_{2\text{-}10}$alkyl group, a $C_{1\text{-}10}$alkoxy$C_{1\text{-}10}$alkyl group, a $C_{1\text{-}10}$alkoxycarbonyl$C_{1\text{-}10}$ alkyl group, a farnesyl group, a 4-morpholinyl$C_{1\text{-}10}$alkyl group, a $C_{1\text{-}10}$alkyl group substituted by a group represented by formula —C(O)NR$^a$R$^b$ (wherein R$^a$ and R$^b$ are identical or different, and each represents a hydrogen atom or a $C_{1\text{-}10}$alkyl group), a group represented by formula —CHR$^c$OC(O)ZR$^d$ (wherein Z represents an oxygen atom, a nitrogen atom, a sulfur atom or a single bond; R$^c$ represents a hydrogen atom, a $C_{1\text{-}10}$alkyl group, a $C_{2\text{-}10}$alkenyl group or an aryl group; and R$^d$ represents a $C_{1\text{-}10}$alkyl group, a $C_{2\text{-}10}$alkenyl group or an aryl group), a group represented by formula [i].

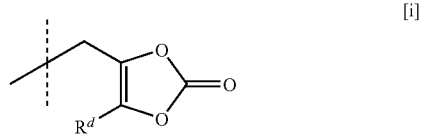

(wherein $R^d$ is the same as described above) or a group represented by formula [ii]; or,

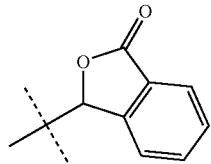

[ii]

in the case where either $R^1$ or $R^2$ represents a hydrogen atom, the other represents a $C_{1-10}$alkyl group, a $C_{2-10}$alkenyl group, a $C_{2-10}$alkynyl group, a $C_{1-10}$alkyl group substituted by one or two aryl groups, a hydroxy$C_{2-10}$alkyl group, a halogeno$C_{1-10}$alkyl group, an azido$C_{1-10}$alkyl group, an amino$C_{2-10}$alkyl group, a $C_{1-10}$alkoxy$C_{1-10}$alkyl group, a $C_{1-10}$alkoxycarbonyl$C_{1-10}$alkyl group, a farnesyl group, a 4-morpholinyl$C_{1-10}$alkyl group, a $C_{1-10}$alkyl group substituted by a group represented by formula —C(O)NR$^a$R$^b$ (wherein R$^a$ and R$^b$ are the same as described above), a group represented by formula —CHR$^c$OC(O)ZR$^d$ (wherein Z, R$^c$ and R$^d$ are the same as described above), a group represented by formula [i]

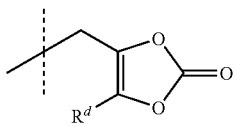

[i]

(wherein $R^d$ is the same as described above) or a group represented by formula [ii].

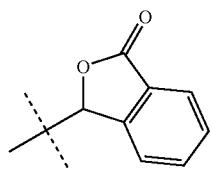

[ii]

X represents a hydrogen atom or a fluorine atom. Y represents —OCHR$^3$R$^4$, —SR$^3$, —S(O)$_n$R$^5$, —SCHR$^3$R$^4$, —S(O)$_n$CHR$^3$R$^4$, —NHCHR$^3$R$^4$, —N(CHR$^3$R$^4$)(CHR$^{3'}$R$^{4'}$), —NHCOR$^3$ or —OCOR$^5$ (wherein R$^3$, R$^{3'}$, R$^4$ and R$^{4'}$ are identical or different, and each represents a hydrogen atom, a $C_{1-10}$alkyl group, a $C_{1-10}$alkenyl group, a phenyl group, a naphthyl group, a naphthyl group substituted by one to seven halogen atoms, a heteroaromatic group or a phenyl group substituted by one to five substituents selected from a group consisting of a halogen atom, a phenyl group, a $C_{1-10}$alkyl group, a $C_{1-10}$alkoxy group, a trifluoromethyl group, a phenyl group, a hydroxycarbonyl group, an amino group, a nitro group, a cyano group and a phenoxy group; R$^5$ represents a $C_{1-10}$alkyl group, a $C_{1-10}$alkenyl group, a phenyl group, a naphthyl group, a naphthyl group substituted by one to seven halogen atoms, a heteroaromatic group or a phenyl group substituted by one to five substituents selected from a group consisting of a halogen atom, a phenyl group, a $C_{1-10}$alkyl group, a $C_{1-10}$alkoxy group, a trifluoromethyl group, a phenyl group, a hydroxycarbonyl group, an amino group, a nitro group, a cyano group and a phenoxy group; and n represents integer 1 or 2)]

In an aspect of the present invention, it is preferred that in formula [I],

R$^1$ and R$^2$ are identical or different, and each represents a $C_{1-10}$alkyl group, a $C_{2-10}$alkenyl group, a $C_{2-10}$alkynyl group, a $C_{1-10}$alkyl group substituted by one or two phenyl groups, a hydroxy$C_{2-10}$alkyl group, a halogeno$C_{1-10}$alkyl group, an azido$C_{1-10}$alkyl group, an amino$C_{2-10}$alkyl group, a $C_{1-10}$alkoxy$C_{1-10}$alkyl group or a $C_{1-10}$alkoxycarbonyl$C_{1-10}$alkyl group; or, in the case where either R$^1$ or R$^2$ represents a hydrogen atom, the other represents a $C_{1-10}$alkyl group, a $C_{2-10}$alkenyl group, a $C_{2-10}$alkynyl group, a $C_{1-10}$alkyl group substituted by one or two phenyl groups, a hydroxy$C_{2-10}$alkyl group, a halogeno$C_{1-10}$alkyl group, an azido$C_{1-10}$alkyl group, an amino$C_{2-10}$alkyl group, a $C_{1-10}$alkoxy$C_{1-10}$alkyl group or a $C_{1-10}$alkoxycarbonyl$C_{1-10}$alkyl group.

In another aspect of the present invention, it is preferred that in formula [I], R$^1$ and R$^2$ are identical or different, and each represents a farnesyl group, a $C_{1-10}$alkyl group substituted by one or two aryl groups, a $C_{1-10}$alkoxycarbonyl$C_{1-10}$alkyl group, a 4-morpholinyl$C_{1-10}$alkyl group, a $C_{1-10}$alkyl group substituted by a group represented by formula —C(O)NR$^a$R$^b$ (wherein R$^a$ and R$^b$ are identical or different, and each represents a hydrogen atom or a $C_{1-10}$alkyl group), a group represented by formula —CHR$^c$OC(O)ZR$^d$ (wherein Z represents an oxygen atom, a nitrogen atom, a sulfur atom or a single bond; R$^c$ represents a hydrogen atom, a $C_{1-10}$alkyl group, a $C_{2-10}$alkenyl group or an aryl group; and R$^d$ represents a $C_{1-10}$alkyl group, a $C_{2-10}$alkenyl group or an aryl group), a group represented by formula [i]

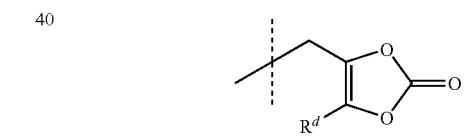

[i]

(wherein $R^d$ is the same as described above) or a group represented by formula [ii]; or,

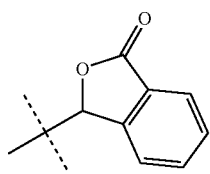

[ii]

in the case where either R$^1$ or R$^2$ represents a hydrogen atom, the other represents a farnesyl group, a $C_{1-10}$alkyl group substituted by one or two aryl groups, a $C_{1-10}$alkoxycarbonyl$C_{1-10}$alkyl group, a 4-morpholinyl$C_{1-10}$alkyl group, a $C_{1-10}$alkyl group substituted by a group represented by formula —C(O)NR$^a$R$^b$ (wherein R$^a$ and R$^b$ are the same as described above), a group represented by formula —CHR$^c$ OC(O)ZR$^d$ (wherein Z, R$^c$ and R$^d$ are the same as described above), a group represented by formula [i]

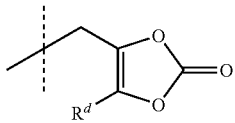

[i]

(wherein R$^d$ is the same as described above) or a group represented by formula [ii];

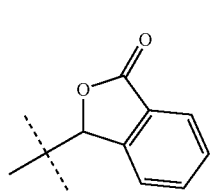

[ii]

In another aspect of the present invention, it is preferred that in formula [I], R$^2$ represents a hydrogen atom.

In a further aspect of the present invention, it is preferred that in formula [I], X represents a fluorine atom.

Further, in another aspect of the present invention, it is preferred that in formula [I], Y represents —OCHR$^3$R$^4$, —SR$^3$, —SCHR$^3$R$^4$, —S(O)$_n$CHR$^3$R$^4$, —NHCHR$^3$R$^4$ or —N(CHR$^3$R$^4$)(CHR$^{3'}$R$^{4'}$) (wherein R$^3$, R$^{3'}$, R$^4$ and R$^{4'}$ are the same as described above).

In another aspect of the present invention, it is preferred that in formula [I], Y represents —SR$^3$, —SCHR$^3$R$^4$, —S(O)$_n$ CHR$^3$R$^4$, —NHCHR$^3$R$^4$ or —N(CHR$^3$R$^4$)(CHR$^{3'}$R$^{4'}$) (wherein R$^3$, R$^{3'}$, R$^4$ and R$^{4'}$ are the same as described above).

It is preferred that in formula [I], R$^3$, R$^{3'}$, R$^4$ and R$^{4'}$ used for describing Y each independently represents a hydrogen atom, a phenyl group, a naphthyl group or a phenyl group substituted by one to five substituents selected from a group consisting of a halogen atom, a phenyl group, a C$_{1-10}$alkyl group, a C$_{1-10}$alkoxy group, a trifluoromethyl group, a phenyl group, a hydroxycarbonyl group, an amino group, a nitro group, a cyano group and a phenoxy group. Of the above, it is more preferred that R$^3$, R$^{3'}$, R$^4$ and R$^{4'}$ each independently represents a hydrogen atom, a phenyl group, a naphthyl group or a phenyl group substituted by one to five halogen atoms.

In a further aspect of the present invention, it is preferred that in formula [I], R$^1$ and R$^2$ each independently represents a hydrogen atom, a C$_{1-10}$alkyl group, a C$_{2-6}$alkenyl group, a C$_{2-6}$alkynyl group, a C$_{1-6}$alkyl group substituted by one or two phenyl groups, a hydroxyC$_{2-6}$alkyl group, a halogenoC$_{1-6}$ alkyl group, an azidoC$_{1-6}$alkyl group, an aminoC$_{2-6}$ alkyl group, a C$_{1-6}$alkoxyC$_{1-6}$alkyl group or a C$_{1-6}$alkoxycarbonylC$_{1-6}$alkyl group. Of the above, it is more preferred that R$^2$ represents a hydrogen atom and R$^1$ represents a straight-chain or branched chain C$_{1-10}$alkyl group, C$_{2-6}$alkenyl group, or C$_{1-6}$alkyl group substituted by one or two phenyl groups.

Further, in another aspect of the present invention, it is preferred that in formula [I], R$^1$ and R$^2$ each independently represents a hydrogen atom, a farnesyl group, a C$_{1-6}$alkyl group substituted by one or two aryl groups, a C$_{1-6}$alkoxycarbonylC$_{1-6}$alkyl group, a 4-morpholinylC$_{1-6}$alkyl group, a C$_{1-10}$alkyl group substituted by a group represented by formula —C(O)NR$^a$R$^b$ (wherein R$^a$ and R$^b$ are the same as described above), a group represented by formula —CHR$^c$ OC(O)ZR$^d$ (wherein Z, R$^c$ and R$^d$ are the same as described above), a group represented by formula [i]

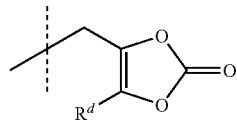

[i]

(wherein R$^d$ is the same as described above) or a group represented by formula [ii].

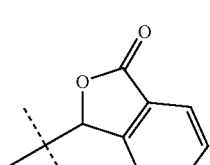

[ii]

Of the above, it is more preferred that R$^2$ represents a hydrogen atom; and R$^1$ represents a farnesyl group, a C$_{1-6}$alkyl group substituted by one or two unsubstituted or substituted phenyl groups, a C$_{1-6}$alkoxycarbonylC$_{1-6}$alkyl group, a 4-morpholinylC$_{1-6}$alkyl group, a C$_{1-10}$alkyl group substituted by a group represented by formula —C(O)NR$^a$R$^b$ (wherein R$^a$ and R$^b$ are the same as described above), a group represented by formula —CHR$^c$OC(O)ZR$^d$ (wherein Z, R$^c$ and R$^d$ are the same as described above), a group represented by formula [i]

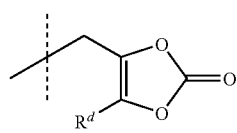

[i]

(wherein R$^d$ is the same as described above) or a group represented by formula [ii].

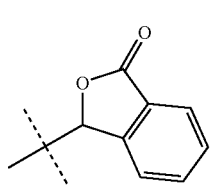

[ii]

It is preferred that in formula [I], R$^a$ and R$^b$ used to describe R$^1$ and R$^2$ represent a hydrogen atom or a C$_{1-6}$alkyl group. It is preferred that R$^c$ represents a hydrogen atom, a C$_{1-6}$alkyl group, a C$_{2-6}$alkenyl group or an aryl group. And it is preferred that R$^d$ represents a C$_{1-6}$alkyl group, a C$_{2-6}$alkenyl group or an aryl group. The terms used in the present invention are defined as follows. C$_{n-m}$ means that the group following C$_{n-m}$ has from n to m carbon atoms.

The C$_{1-10}$alkyl group means a straight-chain alkyl group having one to ten carbon atoms, a branched chain alkyl group having three to ten carbon atoms or a cyclic alkyl group having three to ten carbon atoms. Examples of the straight-chain alkyl group include a methyl group, an ethyl group, a propyl group, a butyl group, a pentyl group, a hexyl group, a heptyl group, an octyl group, a nonyl group and a decyl group. Examples of the branched chain alkyl group include an iso-propyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 5-methylhexyl group, a 3-ethylpentyl group, a 1-propylbutyl group, a 1,4-dimethylpentyl group, a 3,4-dimethylpentyl group, a 1,2,3-trimethylbutyl group, a 1-isopropylbutyl group, a 4,4-dimethylpentyl group, a 5-methylheptyl group, a 6-methylheptyl group, a 4-ethylhexyl group, a 2-propylpentyl group, a 2,5-dimethylhexyl group, a 4,5-dimethylhexyl group, a 2-ethyl-3-methylpentyl group, a 1,2,4-trimethylpentyl group, a 2-methyl-1-isopropylbutyl group, a 3-methyloctyl group, a 2,5-dimethylheptyl group, a 1-(1-methylpropyl)-2-methylbutyl group, a 1,4,5-trimethylhexyl group, a 1,2,3,4-tetramethylpentyl group, a 7-methyloctyl group, a 6-methylnonyl group, a 8-methylnonyl group, a 5-ethyl-2-methylheptyl group, a 2,3-dimethyl-1-(1-methylpropyl)butyl group, a cyclopropylmethyl group, a 2-(cyclopropyl)ethyl group, a 3,7-dimethyloctyl group, a 3-(cyclobutyl)pentyl group, a cyclopentylmethyl group and a cyclohexylmethyl group. Examples of the cyclic alkyl group include a cyclopropyl group, a cyclobutyl group, a cyclopentyl group, a cyclohexyl group, a cycloheptyl group and a cyclooctyl group.

The $C_{2-10}$alkenyl group means a straight-chain alkenyl group having two to ten carbon atoms with at least one double bond, a branched chain alkenyl group having three to ten carbon atoms or a cyclic alkenyl group having five to ten carbon atoms, examples of which include a vinyl group, an allyl group, a 3-butenyl group, a 4-pentenyl group, a 5-hexenyl group, a 6-heptenyl group, a 7-octenyl group, a 8-nonenyl group, a 9-decenyl group, a 1-methyl-2-butenyl group, a 2-methyl-2-butenyl group, a 2-methyl-3-butenyl group, a 2-pentenyl group, a 2-methyl-2-hexenyl group and a 2-cyclopentenyl group.

The $C_{2-10}$alkynyl group means a straight-chain alkynyl group having two to ten carbon atoms with at least one triple bond or a branched chain alkynyl group having four to ten carbon atom, examples of which include a 2-propynyl group, a 3-butynyl group, a 4-pentynyl group, a 5-hexynyl group, a 6-heptynyl group, a 7-octynyl group, a 8-nonynyl group, a 9-decinyl group, a 3-pentynyl group and a 4-methyl-2-pentynyl group.

The $C_{1-10}$alkyl group substituted by one or two aryl groups means, for example, a benzyl group, a diphenylmethyl group, a 2-phenyethyl group, a 2-phenylpropyl group, a 1-methyl-1-phenyethyl group, a 1-methyl-2-phenylpentyl group, a 2-nitrobenzyl group, a 3-nitrobenzyl group, a 4-nitrobenzyl group, a 2,4-dinitrobenzyl group, a 2,4,6-trinitrobenzyl group, a 2-phenylbenzyl group, a 3-phenylbenzyl group, a 4-phenylbenzyl group, a 2-hydroxybenzyl group, a 3-hydroxybenzyl group, a 4-hydroxybenzyl group, a 2-chlorobenzyl group, a 3-chlorobenzyl group, a 4-chlorobenzyl group, a 2-fluorobenzyl group, a 3-fluorobenzyl group, a 4-fluorobenzyl group, a 2-beromobenzyl group, a 3-beromobenzyl group, a 4-beromobenzyl group, a 2-iodobenzyl group, a 2-iodobenzyl group, a 2,3-dichlorobenzyl group, a 2,4-dichlorobenzyl group, a 2,5-dichlorobenzyl group, a 2,6-dichlorobenzyl group, a 3,4-dichlorobenzyl group, a 3,5-dichlorobenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-isopropylbenzyl group, a 3-isopropylbenzyl group, a 4-isopropylbenzyl group, a 2-methoxybenzyl group, a 3-methoxybenzyl group, a 4-methoxybenzyl group, a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, a 3,5-dimethoxybenzyl group, a 2-ethoxybenzyl group, a 3-ethoxybenzyl group, a 4-ethoxybenzyl group, a 2-isopropoxybenzyl group, a 3-isopropoxybenzyl group, a 4-isopropoxybenzyl group, a 2-methoxymethylbenzyl group, a 3-methoxymethylbenzyl group, a 4-methoxymethylbenzyl group, a 2-isopropyxymethylbenzyl group, a 3-isopropyxymethylbenzyl group, a 4-isopropyxymethylbenzyl group, a 2-trifluoromethyl group, a 3-trifluoromethyl group, a 4-trifluoromethyl group, a 2-hydroxycarbonylbenzyl group, a 3-hydroxycarbonylbenzyl group, a 4-hydroxycarbonylbenzyl group, a 2-aminobenzyl group, a 3-aminobenzyl group, a 4-aminobenzyl group, a 2-aminomethylbenzyl group, a 3-aminomethylbenzyl group, a 4-aminomethylbenzyl group, a 2-cyanobenzyl group, a 3-cyanobenzyl group, a 4-cyanobenzyl group, a 2-hydroxymethylbenzyl group, a 3-hydroxymethylbenzyl group, a 4-hydroxymethylbenzyl group, a 2-phenoxybenzyl group, a 3-phenoxybenzyl group and a 4-phenoxybenzyl group.

The aryl group means a phenyl group, a substituted phenyl group or a polycyclic aromatic group such as a 1-naphthyl group or a 2-naphthyl group.

The substituted phenyl group means a phenyl group substituted by one to three substituents selected from a group containing a halogen atom, a hydroxyl group, a phenyl group, a $C_{1-10}$alkyl group, a $C_{1-10}$alkoxy group, a $C_{1-10}$alkoxy$C_{1-10}$alkyl group, a trifluoromethyl group, a hydroxycarbonyl group, an amino group, a nitro group, a cyano group, a hydroxymethyl group, a aminomethyl group and a phenoxy group. Examples of the substituted phenyl group include a 2-nitrophenyl group, a 3-nitrophenyl group, a 4-nitrophenyl group, a 2,4-dinitrophenyl group, a 2,4,6-trinitrophenyl group, a 2-phenylphenyl group, a 3-phenylphenyl group, a 4-phenylphenyl group, a 2-hydroxyphenyl group, a 3-hydroxyphenyl group, a 4-hydroxyphenyl group, a 2-chlorophenyl group, a 3-chlorophenyl group, a 4-chlorophenyl group, a 2-fluorophenyl group, a 3-fluorophenyl group, a 4-fluorophenyl group, a 2-beromophenyl group, a 3-beromophenyl group, a 4-beromophenyl group, a 2-iodophenyl group, a 2-iodophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-methylphenyl group, a 3-methylphenyl group, a 4-methylphenyl group, a 2-ethylphenyl group, a 3-ethylphenyl group, a 4-ethylphenyl group, a 2-isopropylphenyl group, a 3-isopropylphenyl group, a 4-isopropylphenyl group, a 2-methoxyphenyl group, a 3-methoxyphenyl group, a 4-methoxyphenyl group, a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 2-ethoxyphenyl group, a 3-ethoxyphenyl group, a 4-ethoxyphenyl group, a 2-isopropoxyphenyl group, a 3-isopropoxyphenyl group, a 4-isopropoxyphenyl group, a 2-methoxymethylphenyl group, a 3-methoxymethylphenyl group, a 4-methoxymethylphenyl group, a 2-isopropyxymethylphenyl group, a 3-isopropyxymethylphenyl group, a 4-isopropyxymethylphenyl group, a 2-trifluoromethyl group, a 3-trifluoromethyl group, a 4-trifluoromethyl group, a 2-hydroxycarbonylphenyl group, a 3-hydroxycarbonylphenyl group, a 4-hydroxycarbonylphenyl group, a 2-aminophenyl group, a 3-aminophenyl group, a 4-aminophenyl group, a 2-aminomethylphenyl group, a 3-aminomethylphenyl group, a 4-aminomethylphenyl group, a 2-cyanophenyl group, a 3-cyanophenyl group, a 4-cyanophenyl group, a 2-hydroxymethylphenyl group, a 3-hydroxymethylphenyl group, a 4-hydroxymethylphenyl group, a 2-phenoxyphenyl group, a 3-phenoxyphenyl group and a 4-phenoxyphenyl group.

Of the above $C_{1-10}$alkyl groups substituted by one or two aryl groups, the $C_{1-10}$alkyl group substituted by one or two phenyl groups is preferred.

The hydroxy$C_{2-10}$alkyl group means a $C_{2-10}$alkyl group substituted by at least one hydroxyl group, examples of which include a 2-hydroxyethyl group, a 3-hydroxypropyl group, a 4-hydroxybutyl group, a 5-hydroxypentyl group, a 6-hydroxyhexyl group, a 7-hydroxyheptyl group, a 8-hydroxyoctyl group, a 9-hydroxynonyl group, a 10-hydroxydecyl group, a 2-hydroxypropyl group, a 2,3-dihydroxypropyl group and a 2-hydroxy-3-methylbutyl group.

The halogeno$C_{1-10}$alkyl group means a $C_{1-10}$alkyl group substituted by at least one fluorine atom, chlorine atom, bromine atom or iodine atom, examples of which include a 2-chloroethyl group, a 2-bromoethyl group, a 2-iodoethyl group, a 3-chloropropyl group, a 3-bromopropyl group, a 3-iodopropyl group, a 4-chlorobutyl group, a 4-bromobutyl group, a 4-iodobutyl group, a 5-chloropentyl group, a 6-chlorohexyl group, a 7-chloroheptyl group, a 8-chlorooctyl group, a 9-chlorononyl group, a 10-chlorodecyl group, a 2-chloropropyl group, a 2-chlorobutyl group, a 2,4-dichlorobutyl group and a 2-chloro-3-methylbutyl group.

The azido$C_{1-10}$alkyl group means a $C_{1-10}$alkyl group substituted by at least one azide group, examples of which include a 2-azidoethyl group, a 3-azidopropyl group, a 4-azidobutyl group, a 5-azidopentyl group, a 6-azidohexyl group, a 7-azidoheptyl group, a 8-azidooctyl group, a 9-azidononyl group, a 10-azidodecyl group, a 2-azidopropyl group, a 2-azidobutyl group and a 2-azido-3-methylbutyl group.

The amino$C_{2-10}$alkyl group means a $C_{2-10}$alkyl group substituted by at least one amino group, examples of which include a 2-aminoethyl group, a 3-aminopropyl group, a 6-aminohexyl group, a 7-aminoheptyl group, a 8-aminooctyl group, a 9-aminononyl group, a 10-aminodecyl group, a 4-aminobutyl group and a 2,4-diaminobutyl group.

The $C_{1-10}$alkoxy$C_{1-10}$alkyl group means a alkyl group having one to ten carbons which is substituted by a straight-chain alkoxy group having one to ten carbons, a branched chain alkoxy group having three to ten carbon atoms or a cyclic alkoxy group having three to ten carbon atoms, examples of which include a 2-methoxyethyl group, a 2-ethoxyethyl group, a 2-propoxyethyl group, a 2-isopropoxyethyl group, a 2-butoxyethyl group, a 2-isobutoxyethyl group, a 2-t-butoxyethyl group, a 2-pentyloxyethyl group, a 2-hexenyloxyethyl group, a 3-ethoxypropyl group, a 4-ethoxybutyl group, a 4-ethoxy-3-methoxybutyl group and a 4-ethoxy-3-methylpentyl group.

The $C_{1-10}$alkoxycarbonyl$C_{1-10}$alkyl group means a alkyl group having one to ten carbons which is substituted by a straight-chain alkoxycarbonyl group having one to ten carbons, a branched chain alkoxycarbonyl group having three to ten carbon atoms or a cyclic alkoxycarbonyl group having three to ten carbon atoms, examples of which include a methoxycarbonylmethyl group, an ethoxycarbonylmethyl group, a propyloxycarbonylmethyl group, an isopropoxycarbonylmethyl group, a butyltoxycarbonylmethyl group, an isobutoxycarbonylmethyl group, a t-butoxycarbonylmethyl group, a pentyloxycarbonylmethyl group, a hexyloxycarbonylmethyl group, a 2-(ethoxycarbonyl)ethyl group, a 3-(ethoxycarbonyl)propyl group, a 4-(ethoxycarbonyl)butyl group, a 4-(ethoxycarbonyl)pentyl group and a 4-(ethoxycarbonyl)-3-methylpentyl group.

The farnesyl group means a (2Z,6Z)-3,7,1-trimethyldodeca-2,6,10-trienyl group.

The 4-morpholinyl$C_{1-10}$alkyl means a alkyl group having one to ten carbons which is substituted by a 4-morpholinyl group, examples of which include a 2-(4-morpholinyl)ethyl group, a 3-(4-morpholinyl)propyl group, a 4-(4-morpholinyl)butyl group, a 5-(4-morpholinyl)pentyl group, a 6-(4-morpholinyl)hexyl group, a 7-(4-morpholinyl)heptyl group, a 8-(4-morpholinyl)octyl group, a 9-(4-morpholinyl)nonyl group, a 10-(4-morpholinyl)decyl group, a 2-(4-morpholinyl)pentyl group, and a 1-methyl-3-(4-morpholinyl)butyl group.

The $C_{1-10}$alkyl group substituted by formula $C(O)NR^aR^b$ (wherein $R^a$ and $R^b$ are identical or different, and each represents a hydrogen atom or a $C_{1-10}$alkyl group) means, for example, a 2-(N,N-dimethylaminocarbonyl)ethyl group, a 2-(N,N-diethylaminocarbonyl)ethyl group, a 3-(N,N-diethylaminocarbonyl)propyl group, a 2-(N-methylaminocarbonyl)ethyl group, a 2-(N-ethylaminocarbonyl)ethyl group, a 2-(N,N-methylethylaminocarbonyl)ethyl group, a 2-(N,N-ethylpropylaminocarbonyl)ethyl group or a 2-(N,N-diethylaminocarbonyl)-1-methylethyl group.

The naphthyl group substituted by one to seven halogen atoms means a naphthyl group substituted by at least one fluorine atom, chloride atom, bromine atom or iodine atom, examples of which include a 1-fluoro-2-naphthyl group, a 2-fluoro-1-naphthyl group, a 1-chloro-2-naphthyl group, a 2-chloro-1-naphthyl group, a 1-bromo-2-naphthyl group, a 2-bromo-1-naphthyl group, a 1-iodo-2-naphthyl group, a 2-iodo-1-naphthyl group, and a 1,3-difluoro-2-naphthyl group.

The heteroaromatic group means a monocyclic aromatic 5 membered or 6 membered ring containing at least one atom selected from an oxygen atom, a nitrogen atom or a sulfur atom; a monocyclic ring such as above which is fused with a benzene ring; or a hetrocyclic aromatic ring which is fused with one another. Examples of the hetero aromatic group include furyl, pyrrolyl, thiophenyl, oxazoyl, isoxazoyl, imidazoyl, pyrazoyl, thiazoyl, isothiazoyl, oxadiazoyl, thiadiazoyl, benzofuranyl, indolyl, benzothiophenyl, indazoyl, benzoisoxazoyl, benzoisothiazoyl, benzoimidazoyl, benzooxazoyl, benzothiazoyl, pyrizinyl, quinolinyl, isoquinolinyl, pyrodazinyl, pyrimizinyl, pyradinyl, cinnolinyl, phthalazinyl, quinazolinyl and quinoxalinyl.

The $C_{1-10}$alkoxy group means a straight-chain or branched chain alkoxy group having one to ten carbon atoms, examples of which include a methoxy group, an ethoxy group, a propoxy group, an isopropoxy group, a butoxy group, an isobutoxy group, a t-butoxy group, a pentyloxy group and an isopentyloxy group.

The phenyl group substituted by one to five substituents selected from a group containing a halogen atom, a phenyl group, a $C_{1-10}$alkyl group, a $C_{1-10}$alkoxy group, a trifluoromethyl group, a phenyl group, a hydroxycarbonyl group, an amino group, a nitro group, a cyano group and a phenoxy group means a phenyl group substituted by one to five substituents selected from a fluorine atom, a chloride atom, a bromine atom, an iodine atom, a $C_{1-10}$alkyl group, a cyclic $C_{3-10}$ alkyl group, a $C_{1-10}$alkoxy group, a cyclic $C_{3-10}$alkoxy group, a trifluoromethyl group, a phenyl group, a hydroxycarbonyl group, an amino group, a nitro group, a cyano group or a phenoxy group. Examples of the phenyl group substituted by one substituent include a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-methylphenyl group, a 3-methylphenyl group, a 4-methylphenyl group, a 2-ethylphenyl group, a 3-ethylphenyl group, a 4-ethylphenyl group, a 2-isopropylphenyl group, a 3-isopropylphenyl group, a 4-isopropylphenyl group, a 2-cyclopropylphenyl group, a 3-cyclopropylphenyl group, a 4-cyclopropylphenyl group, a 2-cyclohexylphenyl group, a 3-cyclohexylphenyl group, a 4-cyclohexylphenyl group, a 2-methoxyphenyl group, a 3-methoxyphenyl group, a 4-methoxyphenyl group, a 2-isopropoxyphenyl group, a 3-isopropoxyphenyl group, a 4-isopropoxyphenyl group, a 2-cyclobutyloxyphenyl group, a 3-cyclobutyloxyphenyl group, a 4-cyclobutyloxyphenyl group, a 2-cyclohexyloxyphenyl group, a 3-cyclohexyloxyphenyl group, a 4-cyclohexyloxyphenyl group, a 2-trifluoromethylphenyl group, a 3-fluoromethylphenyl group, a 4-trifluoromethylphenyl group, a 2-phenylphenyl group, a 3-phenylphenyl group, a 4-phenylphenyl group, a 2-hydroxycarbonylphenyl group, a 3-hydroxycarbonylphenyl group, a 4-hydroxycarbonylphenyl group, a 2-aminophenyl group, a 3-aminophenyl group, a 4-aminophenyl group, a 2-nitrophenyl group, a 3-nitrophenyl group, a 4-nitrophenyl group, a 2-cyanophenyl group, a 3-cyanophenyl group, a 4-cyanophenyl group, a 2-phenoxyphenyl group, a 3-phenoxyphenyl group and a 4-phenoxyphenyl group. Examples of the phenyl group substituted by two substituents include a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2,3-dibromophenyl group, a 2,4-dibromophenyl group, a 2,5-dibromophenyl group, a 2,6-dibromophenyl group, a 3,4-dibromophenyl group, a 3,5-dibromophenyl group, a 2,3-diiodophenyl group, a 2,4-diiodophenyl group, a 2,5-diiodophenyl group, a 2,6-diiodophenyl group, a 3,4-diiodophenyl group, a 3,5-diiodophenyl group, a 3-chloro-4-fluorophenyl group, a 4-chloro-3-fluorophenyl group, a 3-bromo-4-fluorophenyl group, a 4-bromo-3-fluorophenyl group, a 4-bromo-3-chlorophenyl group, a 3-bromo-4-chlorophenyl group, a 3-chloro-4-methylphenyl group, a 4-chloro-3-methylphenyl group, a 3-fluoro-4-methylphenyl group, a 4-fluoro-3-methylphenyl group, a 3-fluoro-4-methoxyphenyl group, a 4-fluoro-3-methoxyphenyl group, a 3-bromo-4-methoxyphenyl group, a 4-bromo-3-methoxyphenyl group, a 3-chloro-4-phenoxyphenyl group, a 4-chloro-3-phenoxyphenyl group, a 3-chloro-4-nitrophenyl group, a 4-chloro-3-nitrophenyl group, a 4-bromo-3-nitrophenyl group, a 3-bromo-4-nitrophenyl group, a 3-amino-4-bromophenyl group, a 4-amino-3-bromophenyl group, a 3-bromo-4-hydroxycarbonyl group, a 4-bromo-3-hydroxycarbonylphenyl group, a 4-fluoro-3-hydroxycarbonyl group, a 3-fluoro-4-hydroxycarbonylphenyl group, a 4-fluoro-3-hydroxycarbonyl group, a 3-cyano-4-fluorophenyl group, a 3-cyano-4-fluorophenyl group, a 4-cyano-3-methylphenyl group, a 3-cyano-4-methylphenyl group, a 3-cyano-4-methoxyphenyl group and a 4-cyano-3-methoxyphenyl group. Examples of the phenyl group substituted by three substituents include a 2,3,4-trifluorophenyl group, a 3,4,5-trifluorophenyl group, a 3,4,5-trichlorophenyl group, a 3-chloro-2,6-difluorophenyl group, a 3,5-dichloro-4-methoxyphenyl group and a 3,5-dibromo-4-methoxyphenyl group. Examples of the phenyl group substituted by four substituents include a 2,5-dibromo-3,4-dimethoxyphenyl group and a 3,4-dibromo-2,4-dimethoxyphenyl group. Examples of the phenyl group substituted by five substituents include a 2,3,4,5,6-pentafluorophenyl group.

The pharmaceutically acceptable salt in the present invention means, for example, a salt with a mineral acid such as sulfuric acid, hydrochloric acid or phosphoric acid; a salt with organic acids such as acetic acid, oxalic acid, lactic acid, tartaric acid, fumaric acid, maleic acid, methanesulfonic acid or benzenesulfonic acid; a salt with an amine such as trimethylamine or methylamine; or a salt with a metal ion such as sodium ion, potassium ion or calcium ion.

The hydrate in the present invention means a pharmaceutically acceptable hydrate of the compound of the present invention or of the salt thereof. The compound of the present invention or the salt thereof may absorb moisture and accumulate drops of water or become a hydrate by being exposed to the atmosphere or by recrystallization. The hydrate in the present invention includes such a hydrate.

In the compounds represented by formula [I], five assymetric carbon atoms are present in the bicyclo[3.1.0]hexane ring.

The preferred stereostructure of the compounds of the present invention are optically active bodies having the absolute structure represented by formula [II], but the compounds of the present invention may be present as enantiomers or enantiomer mixtures such as racemic bodies. Therefore, the compounds of the present invention include all of the optically active bodies, the enantiomer mixtures such as racemic bodies and the diastereomer mixtures of the compounds represented by formula [II] below.

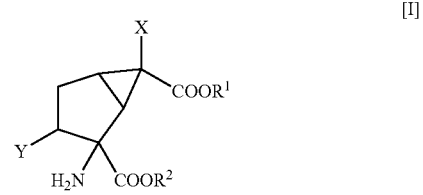

[I]

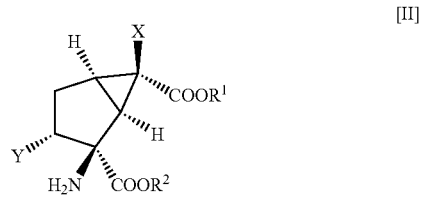

[II]

The compounds of the present invention represented by formula [I] and formula [II] have no effect on group II metabotropic glutamate receptors. However, they can be hydrolyzed with oxygen or with chemicals in vivo, thereby yielding compounds represented by formula [III] and formula [V], respectively, which are compounds that have a strong antagonistic effect on group II metabotropic receptors. Therefore, the compounds of the present invention are effective as drugs that affect the action of group II metabotropic glutamate receptors. The compounds relates to 2-amino-bicyclo[3.1.0]hexane-2,6-dicarboxylic ester derivative, a pharmaceutically acceptable salt thereof or a hydrate thereof,

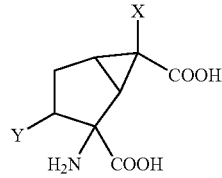

[III]

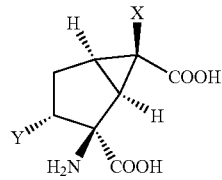

[IV]

[wherein X represents a hydrogen atom or a fluorine atom. Y represents —OCHR$^3$R$^4$, —SR$^3$—S(O)$_n$R$^5$, —SCHR$^3$R$^4$, —S(O)$_n$CHR$^{3'}$R$^{4'}$, —NHCHR$^3$R$^4$, —N(CHR$^3$R$^4$)(CHR$^{3'}$R$^{4'}$), —NHCO R$^3$ or —OCOR$^5$ (wherein R$^3$, R$^{3'}$, R$^4$ and R$^{4'}$ are identical or different, and each represents a hydrogen atom, a C$_{1-10}$alkyl group, a C$_{1-10}$alkenyl group, a phenyl group, a naphthyl group, a naphthyl group substituted by one to seven halogen atoms, a heteroaromatic group or a phenyl group substituted by one to five substituents selected from a group consisting of a halogen atom, a phenyl group, a C$_{1-10}$alkyl group, a C$_{1-10}$alkoxy group, a trifluoromethyl group, a phenyl group, a hydroxycarbonyl group, an amino group, a nitro group, a cyano group and a phenoxy group; R$^5$ represents a C$_{1-10}$alkyl group, a C$_{1-10}$alkenyl group, a phenyl group, a naphthyl group, a naphthyl group substituted by one to seven halogen atoms, a heteroaromatic group or a phenyl group substituted by one to five substituents selected from a group consisting of a halogen atom, a phenyl group, a C$_{1-10}$alkyl group, a C$_{1-10}$alkoxy group, a trifluoromethyl group, a phenyl group, a hydroxycarbonyl group, an amino group, a nitro group, a cyano group and a phenoxy group; and n represents integer 1 or 2)].

BEST METHOD FOR CARRYING OUT THE INVENTION

The present invention relates to a compound of the present invention represented by formula [I] or formula [II], a pharmaceutically acceptable salt thereof or a hydrate thereof. The compounds of the present invention may be synthesized using publicly known methods of organic synthesis. The compounds of the present invention may be prepared, for example, according to the following methods.

First, compounds (9), (16), (24), (27), (30) and (33) which are synthetic intermediates required for synthesizing the compounds of the present invention represented by formula [I] may be prepared as follows. (In the formulas below, X, Y, Z, n, R$^1$, R$^2$, R$^3$, R$^4$ and R$^5$ are the same as described above. R$^6$ represents an aryl- or alkyl-sulfonyl group such as a methyl group, a phenylsulfonyl group, a tosyl group or a trifluoromethylsulfonyl group, a benzoyl group or a 4-nitrobenzoyl group. R$^7$ represents a protecting group for an amino group, examples of which include an alkoxycarbonyl group such as a methoxycarbonyl group, an ethoxycarbonyl group, a t-butoxycorbonyl group or a benzyloxycarbonyl group; an acyl group such as a benzoyl group, a p-phenylbenzoyl group or a (pyridine-2-yl) carbonyl group; an alkyl group such as an aryl group, a benzyl group, a p-methoxybenzyl group or a di(p-methoxyphenyl)methyl group; an alkenyl group such as a 5,5-dimethyl-3-oxo-1-cyclohexenyl group; a sulfenyl group such as a benzenesulfenyl group or a 2,4-dinitrosulfenyl group; a benzylsulfonyl group; a diphenylphosphinyl group; and a dialkylphosphoryl group. A$^1$ represents formula R$^3$ or formula CHR$^3$R$^4$. A$^2$ represents formula R$^5$ or formula CHR$^3$R$^4$. And Q represents formula SR$^3$, formula S(O)$_n$R$^5$, formula SCHR$^3$R$^4$ or formula S(O)$_n$CHR$^3$R$^4$).

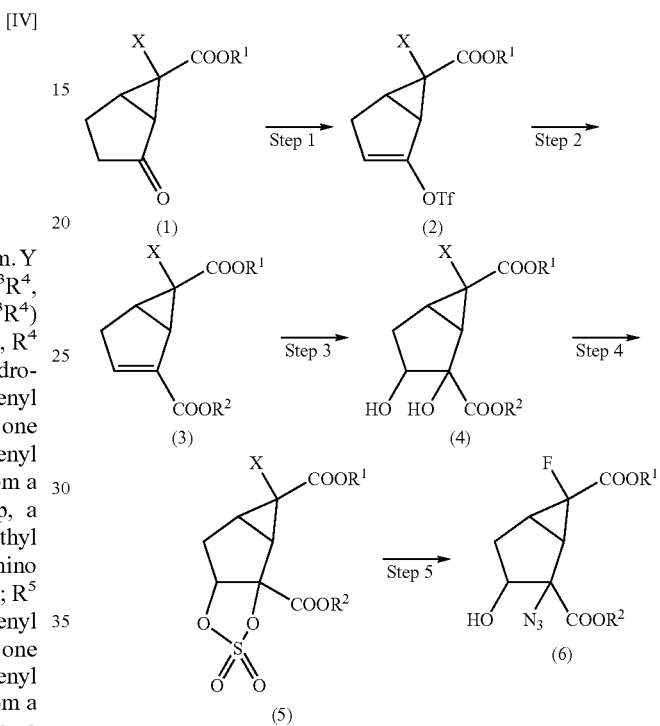

Step 1: Compound (2) may be prepared, for example, by reacting compound (1) with a trifluoromethanesulfonylation agent such as trifluoromethane sulfonic acid anhydride or N-phenyl-bis(trifluoromethanesulfonimide), in an inert solvent, in the presence of a base. Examples of the inert solvent include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; or a mixture of these solvents. Examples of the base include amines such as triethylamine, N-methylmorpholine, diisopropylethylamine and pyridine; inorganic bases such as potassium hydride and sodium hydride; metal amides such as lithium diisopropylamide, potassium bis(trimethylsilyl)amide and lithium hexamethyldisilazane; and metal alcoholates such as sodium methoxide and potassium t-butoxide. Preferably, compound (2) may be prepared by reacting compound (1) with N-phenyl-bis(trifluoromethanesulfonimide) for 2 to 4 hours at −78° C. to room temperature, in tetrahydrofuran, in the presence of lithium hexamethyldisilazane.

Step 2: Compound (3) may be prepared, for example, by reacting compound (2) with carbon monoxide and R$^2$OH, in the presence of organic bases such as triethylamine, N-methylmorpholine, diisopropylethylamine and pyridine or inorganic bases such as potassium carbonate and sodium hydrogen carbonate, in an inert solvent, in the presence of a transition metal catalyst (see Tetrahedron Letters 26, 1109

(1985)). Examples of the transition metal catalyst include a zero-valent palladium reagent which may be prepared in the reaction system, for example, from a divalent palladium such as palladium(II) acetate and a ligand such as triphenylphosphine or 2,2'-bis(diphenylphosphino)-1,1-binaphthyl (BINAP). It is also possible to directly use a zero-valent palladium reagent such as tetrakis(triphenylphosphine) palladium (0). Examples of the inert solvent include hydrocarbon type solvents such as benzene, toluene and hexane; ether type solvents such as tetrahydrofuran, diethyl ether and 1,2-dimethoxyethane; acetonitrile; N,N-dimethylformamide; or a mixture of these solvents. Preferably, compound (3) is prepared by reacting compound (2) with carbon monoxide and $R^2OH$ for 2 to 7 hours at room temperature, in N,N-dimethylformamide, in the presence of diisopropylethylamine, palladium(II) acetate and triphenylphosphine.

Step 3: Compound (4) may be prepared, for example, by oxidizing compound (3) by means of a common diol-formation reaction with osmium tetraoxide (see M. Hudlicky, "Oxidations in Organic Chemistry" or a Sharpless asymmetric cis-dihydroxylation reaction (Sharpless AD) with AD-mix as the reagent (see Tetrahedron Asymmetry 4, 133 (1993), J. Org. Chem. 57, 2768 (1992), J. Org. Chem. 61, 2582 (1996)), in an inert solvent. Examples of the inert solvent include alcohol type solvents such as t-butylalcohol; hydrocarbon type solvents such as benzene, toluene and hexane; ether type solvents such as tetrahydrofuran, diethyl ether and 1,2-dimethoxyethane; acetonitrile; acetone; N,N-dimethylformamide; water; or a mixture of these solvents. Preferably, compound (4) may be prepared by oxidizing compound (3) into diol with osmium tetraoxide for 30 minutes to 3 hours at room temperature, in a mixture of acetonitrile and water.

Step 4: Compound (5) may be prepared, for example, by reacting compound (4) with thionyl chloride, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; or a mixture of these solvents, in the presence or absence of organic bases such as triethylamine, N-methylmorpholine, diisopropylethylamine and pyridine or inorganic bases such as potassium carbonate and sodium hydrogen carbonate, followed by oxidation with a common oxidizing agent such as hydrogen peroxide, OXONE® or ruthenium trichloride-sodium metaperiodate (see M. Hudlicky, "Oxidations in Organic Chemistry"), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents. Preferably, compound (5) may be prepared by reacting compound (4) with thionyl chloride for 30 minutes to 2 hours at ice-cooling, in dichloromethane, in the presence of triethylamine, followed by oxidation for 30 minutes to 2 hours at 0° C. to room temperature, in a mixture of carbon tetrachloride, acetonitrile and water.

Step 5: Compound (6) may be prepared, for example, by reacting compound (5) with sodium azide in an inert solvent, examples of which include ether type solvents such as tetrahydrofuran; ketones such as acetone; N,N-dimethylformamide; water; or a mixture of these solvents, followed by hydrolysis (see J. Am. Chem. Soc. 110, 7538 (1988)). Preferably, compound (6) may be prepared by reacting compound (5) with sodium azide for 1 to 20 hours at room temperature, in a mixture of N,N-dimethylformamide and water, followed by hydrolysis with 20% sulfuric acid for 1 to 2 days at room temperature, in a mixture of diethyl ether and water.

Compound (9), which is a synthetic intermediate of the compound of the present invention, may be prepared from the obtained compound (6) according to Steps 7, 8 and 9 below in the case where in formula [III], Y represents formula $OCHR^3R^4$.

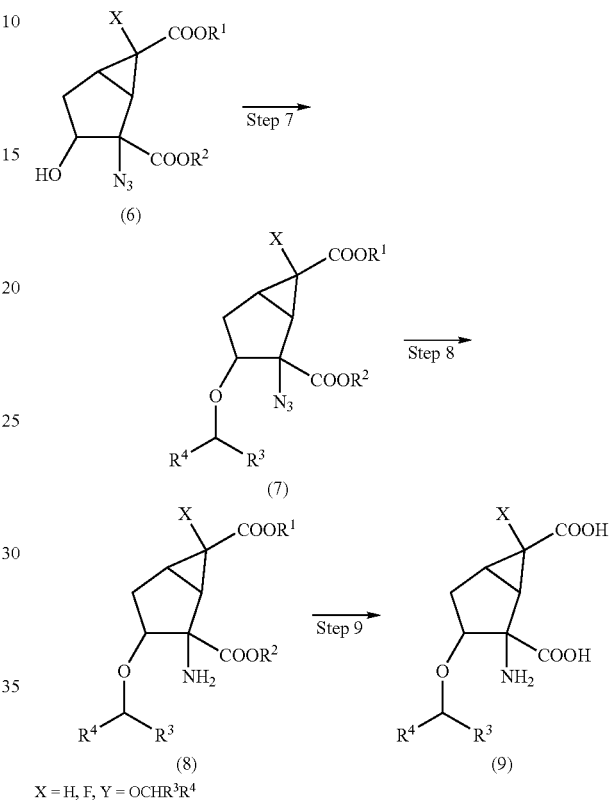

X = H, F, Y = $OCHR^3R^4$

Step 7: Compound (7) may be prepared from compound (6) wherein $R^1$ and $R^2$ represent something other than a hydrogen atom, for example, by reacting the hydroxyl group of compound (6) with a compound of formula $R^3R^4CHL^1$ wherein $L^1$ represents a 2,2,2-trichloroacetimidoyloxy group, in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane, or a mixture of these solvents, in the presence of a Bronsted-acid catalyst such as trifluoromethanesulfonic acid, trifluoroacetic acid or hydrogen chloride, or a Lewis-acid catalyst such as boron trifluoride-diethyl ether complex, zinc chloride, tin chloride or trimethylsilyl-trifluoromethansulfonate (see J. Chem. Soc. Perkin Trans. 1, 2247 (1985), Synthesis, 568 (1987)). In this case, $L^1$ represents a leaving group, for example, a halogen atom, an ethoxycarbonyloxy group or a phenoxycarbonyloxy group.

It is also possible to prepare compound (7) from compound (6) wherein $R^1$ and $R^2$ represent something other than a hydrogen atom, for example, by reacting the hydroxyl group of compound (6) with a compound of formula $R^3R^4CHL^2$ wherein $L^2$ represents something other than a 2,2,2-trichloroacetimidoyloxy group, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence of inorganic bases such as sodium hydride, potassium hydride, potassium carbonate, sodium carbonate, sodium hydroxide and potassium hydroxide; metal amides such as lithium bis(trimethylsilyl)amide, lithium diisopropylamide and sodium amide; organic bases such as triethylamine, diisopropylethylamine, 4-(N,N-dimethylamino)pyridine and 2,6-di-t-butylpyridine; or bases such as potassium t-butoxide. In this case, $L^2$ represents a leaving group, for example, a halogen atom, a tosylsulfonate, a trifluoromethansulfonate or a tolylsulfonate. Preferably, compound (7) may be prepared by reacting compound (6) with the hydroxyl group of a compound of formula $R^3R^4CHL^1$ for 1 to 3 hours at room temperature, in a mixture of chloroform and cyclohexane, in the presence of trifluoromethane sulfonic acid.

Step 8: Compound (8) may be prepared from compound (7), for example, by means of a common reduction reaction of an azide group, typical examples of which include: (a) Staudinger reaction with triethyl phosphite, trimethylphosphine, tributylphosphine, triphenylphosphine or the like (see Bull. Chem. Soc. Fr., 815 (1985)), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents; (b) hydrogenation in an inert solvent, examples of which include alcohols such as ethanol and methanol, esters such as ethyl acetate; N,N-dimethylformamide; water; or a mixture of these solvents, in the presence of a metal catalyst such as palladium/carbon or palladium black; and (c) hydride reduction with lithium aminoborohydride or the like (see A. F. Abdel-Magid, "Reductions in Organic Synthesis"). Preferably, compound (8) may be prepared by reacting compound (7) by means of a Staudinger reaction with trimethylphosphine for 2 to 12 hours at room temperature, in a mixture of tetrahydrofuran and water.

Step 9: Compound (9), which is a synthetic intermediate of the compound of the present invention, may be prepared from compound (8) wherein $R^1$ and $R^2$ represent something other than a hydrogen atom, by converting the moieties represented by formula $COOR^1$ and formula $COOR^2$ of compound (8) into carboxylic acid by means of a common hydrolysis reaction (see T. W. Greene, P. G. M. Wuts, "Protective Groups in Organic Synthesis"). Preferably, compound (9), which is a synthetic intermediate of the compound of the present invention, may be prepared by hydrolizing compound (8) with lithium hydroxide for 1 to 7 days at room temperature to 50° C., in a mixture of tetrahydrofuran and water.

Compound (16), which is a synthetic intermediate of the compound of the present invention, may be prepared from compound (6) according to Steps 10, 11, 12, 13, 14 and 15 below in the case where in formula [III], Y represents formula $SR^3$, formula $S(O)_nR^5$, formula $SCHR^3R^4$ and formula $S(O)_nCHR^3R^4$.

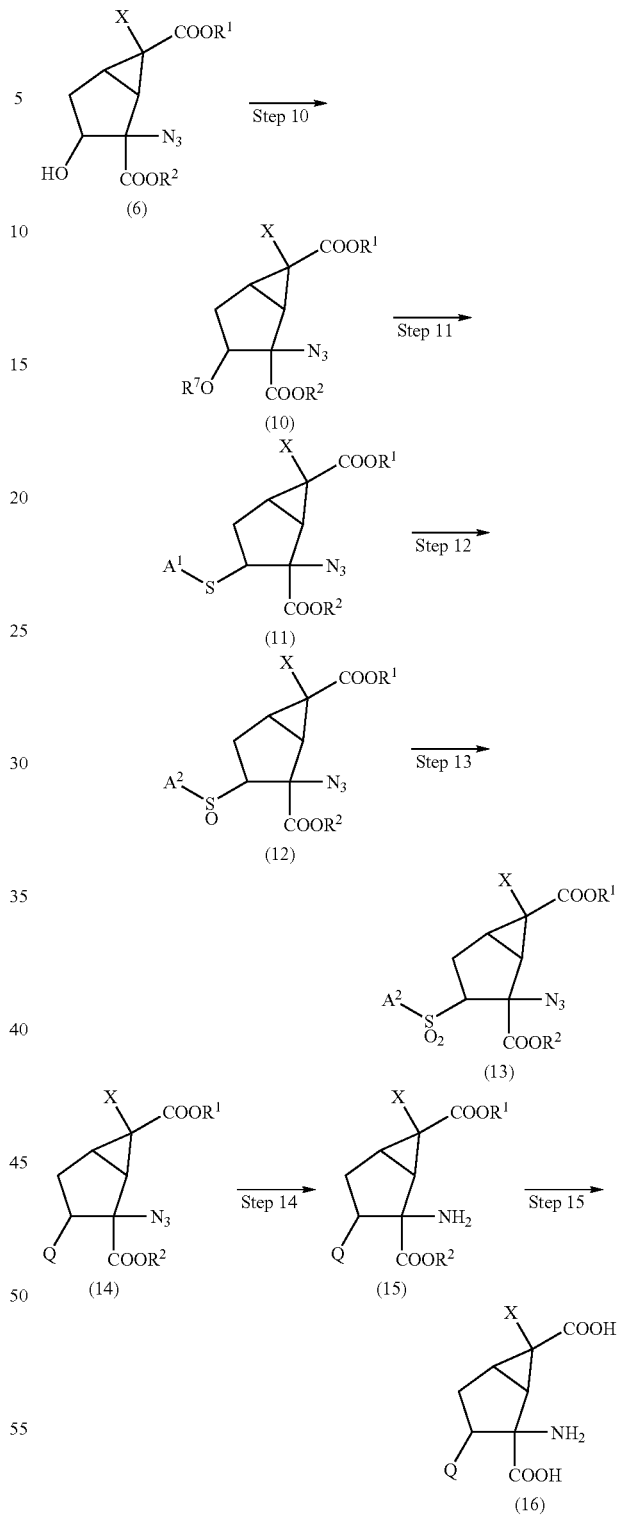

$X = H, F, Y = SR^3, S(O)_nR^5, SCHR^3R^4, S(O)_nCHR^3R^4$

Step 10: Compound (10) may be prepared from compound (6) wherein $R^1$ and $R^2$ represent something other than a hydrogen atom, for example, by reacting the hydroxyl group of compound (6) with a trifluoromethanesulfonylation agent such as trifluoromethane sulfonic acid anhydride or N-phenyl-bis(trifluoromethanesulfonimide); or with an alkyl- or aryl-sulfonylation agent such as methanechloride sulfonic acid, benzenechloride sulfonic acid or toluenechloride sulfonic acid, in an inert solvent, examples of which include hydrocarbon type solvents such as benzene, toluene, hexane and cyclohexan; halogen type solvents such as dichloromethane, chloroform and carbon tetrachloride; ether type solvents such as tetrahydrofuran, diethyl ether and 1,2-dimethoxyethane, amides such as N,N-dimethylformamide and N-methyl-2-pyrrolidinone; dimethylsulfoxide; or a mixture of these solvents, in the presence of inorganic bases such as sodium hydride, potassium hydride, potassium carbonate, sodium carbonate, sodium hydroxide and potassium hydroxide; metal amides such as lithium bis(trimethylsilyl)amide, lithium diisopropylamide and sodium amide; organic bases such as triethylamine, pyridine, diisopropylethylamine, 4-(N, N-dimethylamino)pyridine and di-t-butylpyridine; or bases such as potassium t-butoxide. Preferably, compound (10) may be prepared by reacting the hydroxyl group of compound (6) with trifluoromethane sulfonic acid anhydride for 30 minutes to 3 hours at −78° C. to ice-cooling, in dichloromethane, in the presence of pyridine.

Step 11: Compound (1) may be prepared, for example, by reacting compound (10) with a compound of formula $A^1SNa$, formula $A^1SK$ or the like, which is prepared from metal alcoholates such as sodium ethoxide and potassium t-butoxide; sodium; potassium; sodium hydride; potassium hydride; and mercaptans and thiophenols represented by formula $A^1SH$, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; dimethylsulfoxide; N,N-dimethylformamide; or a mixture of these solvents. Preferably, compound (11) is prepared by reacting compound (10) with a compound of formula $A^1SHNa$, which is prepared from sodium and from a compound of formula $A^1SH$, for 10 minutes to 1 hour at room temperature, in dimethylsulfoxide.

Step 12: Compound (12) may be prepared from compound (11) wherein $A^1$ represents something other than a hydrogen atom, for example, by means of a common oxidation reaction that coverts sulfides into sulfoxides using sodium periodate, peracetic acid or the like (see M. Hudlicky, "Oxidations in Organic Chemistry"), in an inert solvent, examples of which include hydrocarbon type solvents such as benzene, toluene and hexane; halogen type solvents such as dichloromethane, chloroform and carbon tetrachloride, ether type solvents such as tetrahydrofuran, diethyl ether and 1,2-dimethoxyethane; acetonitrile; acetone; dimethylsulfoxide; N,N-dimethylformamide; methanol; ethanol; acetic acid; water; or a mixture or these solvents.

Step 13: Compound (13) may be prepared from compound (12) or from compound (11) wherein $A^1$ represents something other than a hydrogen atom, for example, by means of a common oxidation reaction that converts sulfides or sulfoxides into sulfines using 3-chloroperbenzoic acid, hydrogen peroxide or the like (see M. Hudlicky, "Oxidations in Organic Chemistry"), in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; dimethylsulfoxide; N,N-dimethylformamide; water; or a mixture of these solvents. It is also possible to prepare a mixture of compound (12) and compound (13) from compound (11) wherein $A^1$ represents something other than a hydrogen atom, for example, by using a common oxidizing agent such as 3-chloroperbenzoic acid or hydrogen peroxide (see M. Hudlicky, "Oxidations in Organic Chemistry") and by controlling the reaction conditions such as the amount, reaction time, reaction temperature and solvent of the oxidizing agent, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; dimethylsulfoxide; N,N-dimethylformamide; water; or a mixture of these solvents. Preferably, compound (12) and compound (13) may be prepared by reacting compound (11) with 3-chloroperbenzoic acid for 1 to 24 hours at −78° C. to room temperature, in dichloromethane.

Step 14: Compound (15) may be prepared from compound (14), for example, by means of a common reduction reaction of an azide group, typical examples of which include: (a) Staudinger reaction with triethyl phosphite, trimethylphosphine, tributylphosphine or triphenylphosphine (see Bull. Chem. Soc. Fr., 815 (1985)) in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water, or a mixture of these solvents; (b) hydrogenation in an inert solvent, examples of which include alcohols such as ethanol and methanol, esters such as ethyl acetate; N,N-dimethylformamide; water; or a mixture of these solvents, in the presence of a metal catalyst such as palladium/carbon or palladium black; and (c) hydride reduction with lithium aminoborohydride or the like (see A. F. Abdel-Magid, "Reductions in Organic Synthesis"). Preferably, compound (15) may be prepared by reacting compound (14) by means of a Staudinger reaction with trimethylphosphine for 1 to 2 hours at room temperature, in a mixture of tetrahydrofuran and water.

Step 15: Compound (16), which is a synthetic intermediate of the compound of the present invention, may be prepared from compound (15) wherein at least one of $R^1$ and $R^2$ represent something other than a hydrogen atom, by hydrolyzing the moieties represented by formula $COOR^1$ and formula $COOR^2$ of compound (15) by means of the same method as Step 9. Preferably, compound (16), which is a synthetic intermediate of the compound of the present invention, may be prepared by hydrolyzing compound (15) with lithium hydroxide for 5 to 7 days at room temperature to 40° C., in a mixture of tetrahydrofuran and water. Or preferably, compound (16) may be prepared by hydrolyzing compound (15) with 60% sulfuric acid for 1 to 5 days at 100° C. to 150° C.

Compounds (24) and (27), which are synthetic intermediates of the compound of the present invention, may be prepared from synthetic intermediate (6) according to Steps 16, 17, 18, 19, 20, 21 and 22 below in the case where in formula [III], Y represents formula $NHCHR^3R^4$ or formula $N(CHR^3R^4)(CHR^3R^4)$.

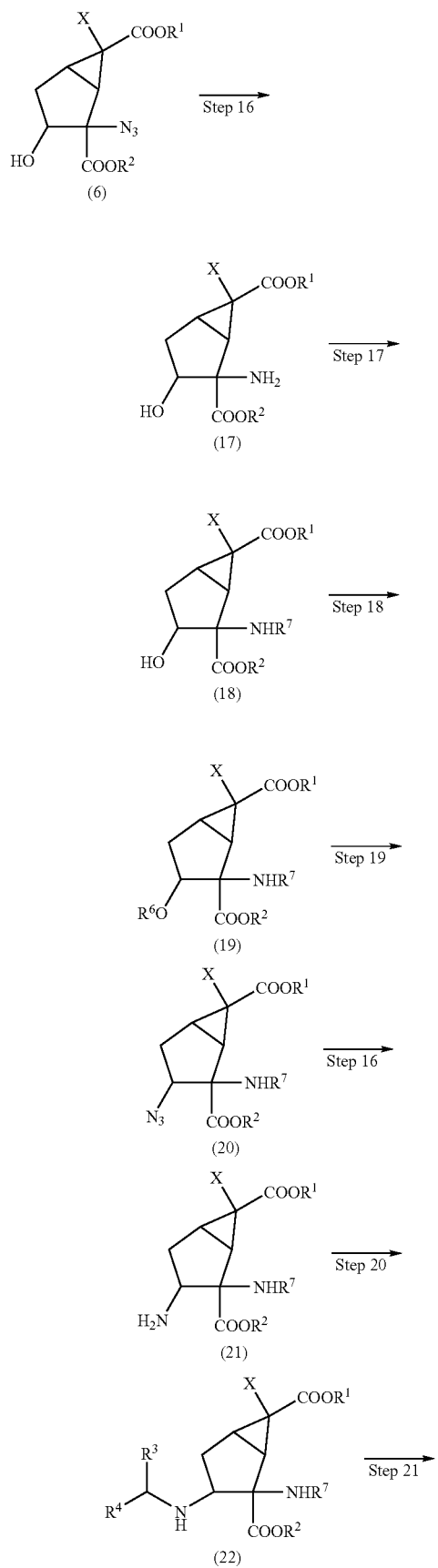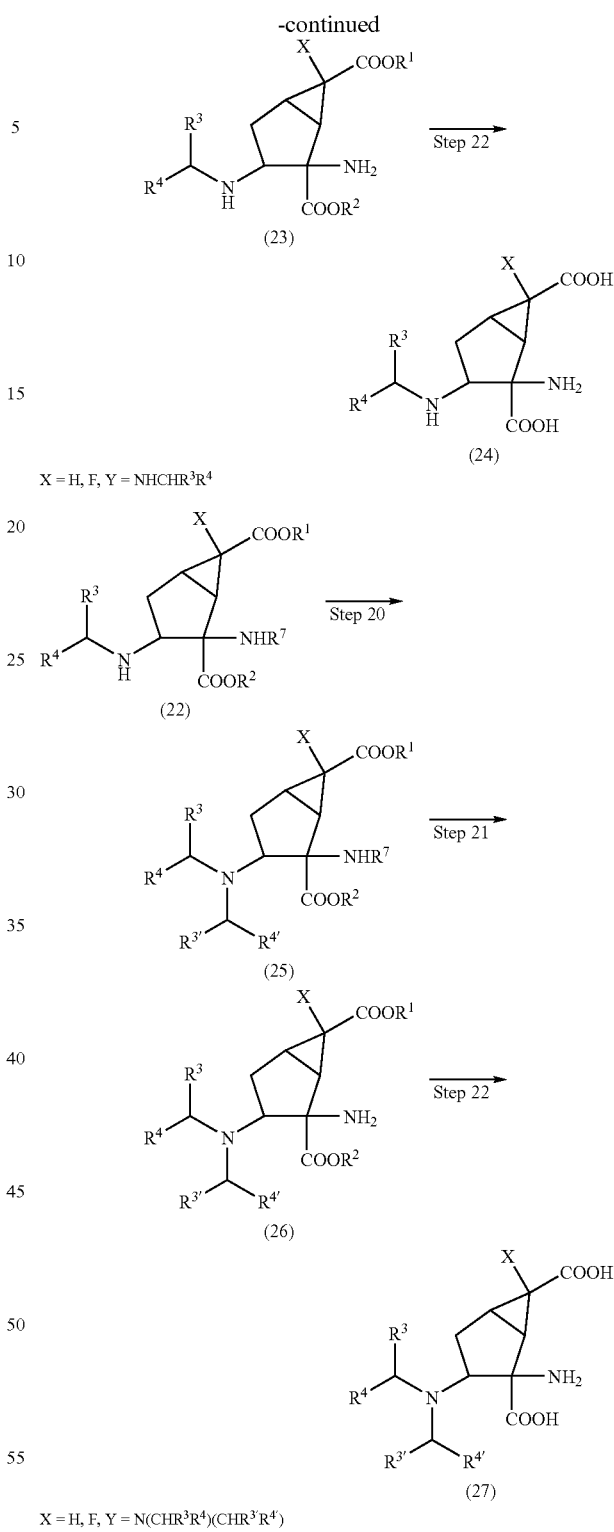

X = H, F, Y = NHCHR³R⁴

X = H, F, Y = N(CHR³R⁴)(CHR³'R⁴')

Step 16: Compounds (17) and (21) may be prepared from compounds (6) and (20), respectively, by reducing the azide group by means of the same method as Step 14. Preferably, compound (17) and compound (21) may be prepared from compound (6) and compound (20), respectively, by means of a Staudinger reaction with trimethylphosphine for 1 to 12 hours at room temperature, in a mixture of tetrahydrofuran and water.

Step 17: Compound (18) may be prepared from compound (17) by protecting the amino group of compound (17) by means of a common protection reaction of an amino group (see T. W. Greene, P. G. M. Wuts, "Protective Groups in Organic Synthesis"). Preferably, compound (18) may be prepared by reacting compound (17) with di-t-butyldicarbonate for 2 to 6 hours at room temperature, in tetrahydrofuran, in the presence of a saturated aqueous solution of sodium hydrogen carbonate.

Step 18: Compound (19) may be prepared from compound (18) wherein $R^1$ and $R^2$ represent something other than a hydrogen atom, by alkyl- or aryl-sulfonylating the hydroxyl group of compound (18) by means of the same method as Step 0. Preferably, compound (19) may be prepared by reacting the hydroxyl group of compound (18) with trifluoromethane sulfonic acid anhydride for 30 minutes to 2 hours at −78° C. to ice-cooling, in dichloromethane, in the presence of pyridine.

Step 19: Compound (20) may be prepared, for example, by reacting compound (19) with sodium azide in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; ethyl acetate; acetonitrile; acetone; dimethylsulfoxide; N,N-dimethylformamide; water; or a mixture of these solvents. Preferably, compound (20) may be prepared by reacting compound (19) with sodium azide for 1 to 2 days at room temperature to 35° C., in N,N-dimethylformamide.

Step 20: Compounds (22) and (25) may be prepared from compounds (21) and (22), respectively, for example, by reacting the amino groups represented by formula —$NH_2$ and formula —$R^3R^4CHNH$ of compounds (21) and (22) with a compound of formula $R^3R^4CHL^2$ or formula $R^3{}'R^4CHL^2$, in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence or absence of inorganic bases such as sodium hydride, potassium hydride, potassium carbonate, sodium carbonate, sodium hydrogen carbonate, sodium hydroxide and potassium hydroxide; metal amides such as lithium bis(trimethylsilyl)amide, lithium diisopropylamide and sodium amide; organic bases such as triethylamine, pyridine, diisopropylethylamine, 4-(N,N-dimethylamino)pyridine and 2,6-di-t-butylpyridine; or bases such as potassium t-butoxide. In this case, $L^2$ represents a leaving group, for example, a halogen atom, a tosylsulfonate, a trifluoromethansulfonate or a tolylsulfonate. It is also possible to prepare compounds (22) and (25), respectively, for example, by reductively aminating compounds (21) and (22) by means of a Borch reaction in which compounds (21) and (22) are reacted with compounds of formula $R^3COR^4$ or formula $R^3{}'COR^{4'}$ (see A. F. Abdel-Magid et al., Tetrahedron Lett., 31, 5595 (1990)) in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; ethanol; methanol; water; or a mixture of these solvents, in the presence of a reducing agent such as sodium triacetoxyborohydride or sodium cyanotrihydroborate. Preferably, compound (22) may be prepared by reacting compound (21) with a compound of formula $R^3R^4CHBr$ for 1 to 4 days at room temperature, in chloroform, in the presence of pyridine. And preferably, compound (25) may be prepared by reacting compound (22) with a compound of formula $R^3{}'R^4CHI$ for 1 to 4 days at room temperature, in N,N-dimethylformamide, in the presence of potassium carbonate.

Step 21: Compounds (23) and (26) may be prepared from compound (22) and compound (25), respectively, by deprotecting $R^7$, which is the protecting group for the amino group of compounds (22) and (25), by means of a common deprotection reaction (see T. W. Greene, P. G. M. Wuts, "Protective Groups in Organic Synthesis") that converts $R^7$ into an amino group. Preferably, compound (23) and compound (26) may be prepared by deprotecting compound (22) and compound (25) with 4N hydrogen chloride/ethyl acetate for 12 to 36 hours at ice-cooling to room temperature.

Step 22: Compounds (24) and (27), which are synthetic intermediates of the compound of the present invention, may be prepared from compounds (23) and (26) wherein at least one of $R^1$ and $R^2$ represent something other than a hydrogen atom, by hydrolyzing the moieties represented by formula $COOR^1$ and $COOR^2$ of compounds (23) and (26), by means of the same method as Step 9. Preferably, compound (24) and compound (27), which are synthetic intermediates of the compound of the present invention, may be prepared by hydrolyzing compound (23) and compound (26), respectively, with lithium hydroxide for 1 to 7 days, in a mixture of tetrahydrofuran and water.

Compound (30), which is a synthetic intermediate of the compound of the present invention, may be prepared from compound (21) according to Steps 23, 24 and 25 below in the case where in formula [III], Y represents formula —$NHCOR^3$.

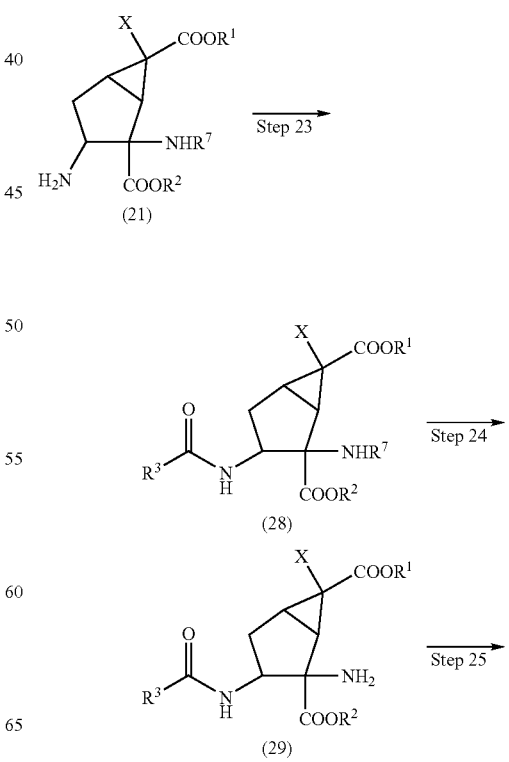

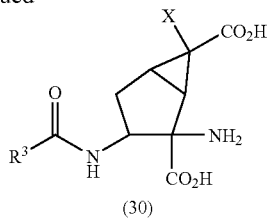

(30)

Y = NHCOR³

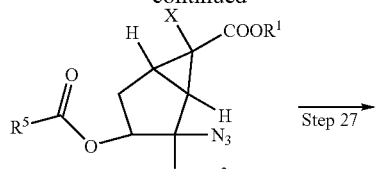

(31)

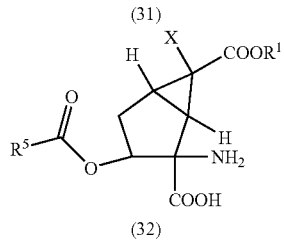

(32)

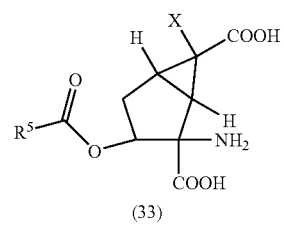

(33)

Y = OCOR⁵, R² = Bn

Step 23: Compound (28) may be prepared from compound (21), for example, by reacting the 3-position amino group of compound (21) with a compound of formula L¹COR³ or formula R³COOCOR³ in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence or absence of organic bases such as triethylamine, pyridine, morpholine, diisopropylethylamine, 4-(N,N-dimethylamino)pyridine and 2,6-di-t-butylpyridine.

In this case, L¹ represents a leaving group, for example, a halogen atom, an ethoxycarbonyloxy group or a phenoxycarbonyloxy group. It is also possible to prepare compound (28) by means of a common formylation reaction (see T. W. Greene, P. G. M. Wuts, "Protective Groups in Organic Synthesis") in the case where R³ represents a hydrogen atom. Preferably, compound (28) may be prepared by reacting compound (21) with a compound of formula R³COCl for 1 to 4 hours at room temperature, in chloroform, in the presence of pyridine.

Step 24: Compound (29) may be prepared from compound (28) by means of the same deprotection reaction of formula —NHR⁷ as Step 21. Preferably, compound (29) may be prepared by deprotecting compound (28) with 4N hydrogen chloride/ethyl acetate for 30 minutes to 2 hours at ice-cooling.

Step 25: Compound (30), which is an intermediate of the compound of the present invention, may be prepared from compound (29) wherein at least one of R¹ and R² represent something other than a hydrogen atom, by means of the same method of hydrolysis reaction of formula —COOR¹ and formula —COOR² as Step 9. Preferably, compound (30), which is a synthetic intermediate of the compound of the present invention may be prepared by hydrolyzing compound (29) with lithium hydroxide for 1 to 7 hours at room temperature, in a mixture of tetrahydrofuran and water. Compound (33), which is a synthetic intermediate of the compound of the present invention, may be prepared from synthetic intermediate (6) wherein R² represents a benzyl group, according to Steps 26, 27 and 28 below in the case where in formula [III], Y represents formula —OCOR⁵.

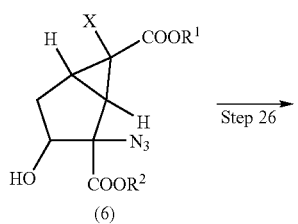

(6)

Step 26: Compound (31) may be prepared from compound (6) wherein R¹ represents something other than a hydrogen atom and R² represents a benzyl group, for example, by reacting the hydroxyl group of compound (6) with a compound of formula L¹COR⁵ or formula R⁵COOCOR⁵ either in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethan; amides such as N,N-dimethylformamide and N-methyl-2-pyrrolidinone; dimethylsulfoxide; or a mixture of these solvents or in the absence of any solvent, in the presence or absence of organic bases such as triethylamine, pyridine, morpholine, diisopropylethylamine, 4-(N,N-dimethylamino)pyridine and 2,6-di-t-butylpyridine. In this case, L¹ represents a leaving group, for example, a halogen atom, an ethoxycarbonyloxy group or a phenoxycarbonyloxy group. Preferably, compound (31) may be prepared by reacting compound (6) with a compound of formula R⁵COCl for 12 to 36 hours at room temperature, in pyridine.

Step 27: compound (32) may be prepared from compound (31), for example, by yielding an amino body by means of a Staudinger reaction with triethyl phosphite, trimethylphosphine, tributylphosphine or triphenylphosphine, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents (see Bull. Chem. Soc. Fr., 815 (1985)), and then, for example, by reductively deprotecting the benzyl group of the obtained amino body by means of a hydrogenation reaction, in an inert solvent, examples of which include alcohols such as ethanol and methanol; esters such as ethyl acetate; N,N-dimethylformamide; water; or a mixture of these solvents, in the presence of a metal catalyst such as palladium/carbon or palladium black. It is also possible to directly prepare compound (32) from compound (31), for example, by means of a hydrogenation reaction, in an inert solvent, examples of which include alcohols such as ethanol and methanol; esters such as ethyl acetate; N,N-dimethylformamide; water; or a mixture of these solvents, in the presence of a metal catalyst such as palladium/carbon or palladium black. Preferably, an amine body may be prepared by reacting compound (31) by means of a Staudinger reaction with trimethylphosphine for 30 minutes to 2 hours at room temperature, in a mixture of tetrahydrofuran and water. Compound (32) may then be prepared by reacting the amine body for 30 minutes to 2 hours at room temperature, in ethanol, in the presence of 5% palladium carbon, under a hydrogen atmosphere.

Step 28: Compound (33), which is a synthetic intermediate of the compound of the present invention, may be prepared from compound (32) wherein $R^1$ represents something other than a hydrogen atom, by means of the same method as Step 9. Preferably, compound (33), which is a synthetic intermediate of the compound of the present invention, may be prepared by hydrolyzing compound (32) with lithium hydroxide for 30 minutes to 2 hours at room temperature, in a mixture of tetrahydrofuran and water.

Compound [I] of the present invention may be prepared by means of monoesterification or diesterification of the two carboxylic acid moieties of the obtained synthetic intermediate [III].

Compound [I], which is the compound of the present invention, may be prepared by means of diesterification or monoesterification of the carboxylic acid moieties of compound [III] according to Step 29 below.

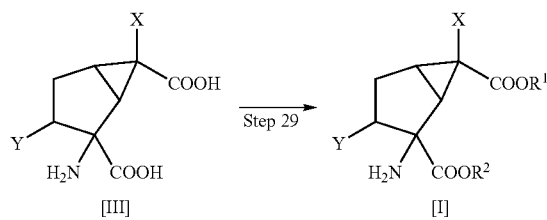

Step 29: Compound [I], which is the compound of the present invention, may be prepared by means of a common esterification reaction of the carboxylic acid moiety of compound [III] (see T. W. Greene, P. G. M. Wuts, "Protective Groups in Organic Synthesis"). Preferably, compound [I] of the present invention may be prepared by converting the carboxylic acid moiety of compound [III] to lithium salt using lithium hydroxide at room temperature in tetrahydrofuran, and then by reacting compound [III] with compounds of formula $R^1Br$ and formula $R^2Br$ for 4 to 12 hours at room temperature to 90° C., in N,N-dimethylformamide. It is also possible to selectively prepare compound [I], which is the compound of the present invention and wherein $R^2$ represents a hydrogen atom, by reacting the carboxylic acid moiety on the 6-position carbon of compound [III] with alcohol represented by formula $R^1OH$, for a short period of time or by controlling the reaction temperature, either in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; dimethylsulfoxide; N,N-dimethylformamide; or a mixture of these solvents or without any solvent, in the presence or absence of mineral acids such as sulfuric acid, phosphoric acid and hydrochloric acid; organic acids such as acetic acid, oxalic acid and methanesulfonic acid; or chloride acids such as thionyl chloride and phosphoryl chloride. Preferably, compound [I] of the present invention wherein $R^2$ represents a hydrogen atom may be prepared by reacting the carboxylic acid moiety on the 6-position carbon of compound [III] for 1 hour to 3 days at ice-cooling to 80° C., in the presence of alcohol represented by formula $R^1OH$ and of thionyl chloride.

It is also possible to selectively prepare compound [I] wherein $R^2$ represents a hydrogen atom by protecting the amino acid moiety on the 2-position carbon by means of a protection method of α-amino acid using triethylboran, copper(II) complex or the like (see International Journal of Peptide & Protein Research, 37, 210 (1991); Synthesis, 119 (1990); Helv. Chem. Acta, 44, 159 (1961)), and then esterifying the carboxylic acid moiety on the 6-position carbon by means of a common esterification reaction (see T. W. Greene, P. G. M. Wuts, "Protective Groups in Organic Synthesis"), followed by a deprotection reaction of the α-amino acid moiety (see International Journal of Peptide & Protein Research, 37, 210 (1991); Synthesis, 119 (1990); Helv. Chem. Acta, 44, 159 (1961)).

After compound [I] wherein $R^2$ represents an hydrogen atom has been selectively prepared, compound [I] of the present invention wherein $R^1$ and $R^2$ both represent something other than a hydrogen atom may be prepared by either protecting or not protecting the amino group on the 2-position carbon with a common protecting group for an amino group such as an allyloxycarbonyl group or a tert-butoxycarbonyl group (see T. W. Greene, P. G. M. Wuts, "Protective Groups in Organic Synthesis") and then esterifying the carboxylic acid moiety on the 2-position carbon by means of a common esterification reaction (see T. W. Greene, P. G. M. Wuts, "Protective Groups in Organic Synthesis"), and in the case where the amino group has been protected, followed by a deprotection reaction of amino groups (see T. W. Greene, P. G. M. Wuts, "Protective Groups in Organic Synthesis"). Preferably, Compound [I] of the present invention wherein $R^1$ and $R^2$ both represent something other than a hydrogen atom may be prepared by protecting the amino group on the 2-position carbon with an allyloxycarbonyl group by reacting the amino group for 8 hours at room temperature, in the presence of allyl chloroformate and saturated sodium hydrogen carbonate; and then reacting the amino group with $R^2X'$ (wherein $R^2$ represents a halogen atom and X' preferably represents a bromine atom or a iodine atom) for 1 to 24 hours, in the presence of potassium carbonate; followed by a deprotection reaction of an amino group in which the amino group is reacted with tetrakis(triphenylphosphine)palladium for 1 to 24 hours at room temperature to 80° C., in the presence of 1,3-dimethylbarbituric acid.

It is also possible to selectively prepare compound [I], which is the compound of the present invention wherein $R^1$ represents a hydrogen atom, from compound [I] wherein $R^1$ and $R^2$ represent something other than a hydrogen atom, by converting the moiety represented by formula $COOR^1$ of compound [I] into a carboxylic acid by means of a common hydrolysis reaction (see T. W. Greene, P. G. M. Wuts, "Protective Groups in Organic Synthesis"), for a short period of time or at a low temperature. Preferably, compound [I] of the present invention wherein $R^1$ represents a hydrogen atom may be prepared from compound [I] wherein $R^1$ and $R^2$ represent something other than a hydrogen atom, by hydrolyzing the moiety represented by formula $COOR^1$ of compound [1] with lithium hydroxide for 30 minutes to 3 hours at 0° C. to room temperature, in a mixture of tetrahydrofuran and water.

It is further possible to prepare compound [I] wherein at least one of $R^1$ and $R^2$ represent an azido$C_{1-10}$alkyl group from a corresponding compound [I] wherein at least one of $R^1$ and $R^2$ represent a halogeno$C_{1-10}$alkyl, for example, by reacting compound [I] with sodium azide in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; ethyl acetate; acetonitrile; acetone; dimethylsulfoxide; N,N-dimethylformamide; water; or a mixture of these solvents. Preferably, compound [I] wherein at least one of $R^1$ and $R^2$ represent an azido$C_{1-10}$alkyl group may be prepared by reacting a compound [I] wherein at least one of $R^1$ and $R^2$ represent a halogeno$C_{1-10}$alkyl group with sodium azide for 6 to 18 hours at room temperature to 60° C., in a mixture of N,N-dimethylformamide and water.

It is further possible to prepare compound [I] wherein at least one of $R^1$ and $R^2$ represent an amino$C_{2-10}$alkyl group from a corresponding compound [I] wherein at least one of $R^1$ and $R^2$ represent an azido$C_{1-10}$alkyl group, by hydrolyzing the azido moiety of compound [I] by means of a common reduction reaction of an azide group, typical examples of which include: (a) Staudinger reaction with triethyl phosphite, trimethylphosphine, tributylphosphine or triphenylphosphine (see Bull. Chem. Soc. Fr., 815 (1985)) in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; acetonitrile; acetone; water; or a mixture of these solvents; (b) hydrogenation in an inert solvent, examples of which include alcohols such as ethanol and methanol, esters such as ethyl acetate; N,N-dimethylformamide; water; or a mixture of these solvents, in the presence of a metal catalyst such as palladium/carbon or palladium black; and (c) hydride reduction with lithium aminoborohydride or the like (see A. F. Abdel-Magid, "Reductions in Organic Synthesis"). Preferably, compound [I] wherein at least one of $R^1$ and $R^2$ represent a amino$C_{1-10}$alkyl group may be prepared by reacting compound [I] wherein at least one of $R^1$ and $R^2$ represent an azido$C_{1-10}$alkyl group by means of a Staudinger reaction with trimethylphosphine for 6 to 18 hours at room temperature, in a mixture of tetrahydrofuran and water.

Further, it is also possible to prepare compound [I] of the present invention wherein $R^1$ represents something other than a hydrogen atom and $R^2$ represents a hydrogen atom from the obtained compound [III] according to Steps 30, 31, 32 and 33 below.

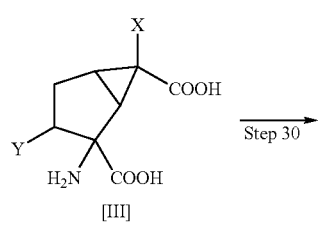

[III]

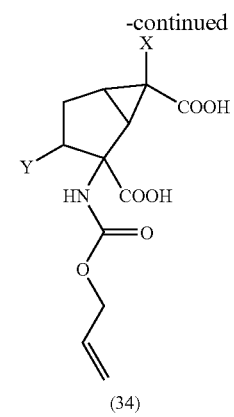

(34)

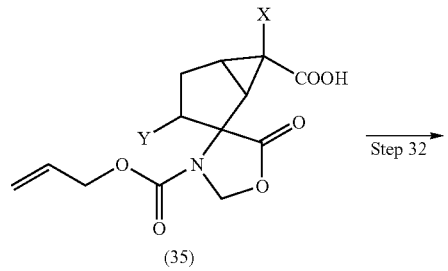

(35)

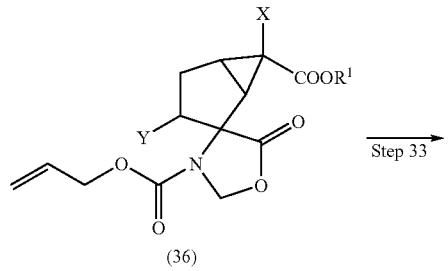

(36)

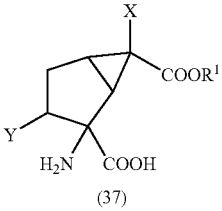

(37)

Step 30: compound (34) may be prepared, for example, by reacting the amino group of compound [III] with allyl chloroformate in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether, 1,2-dimethoxyethane and 1,4-dioxane; amides such as N,N-dimethylformamide and N-methyl-2-pyrrolidinone; dimethylsulfoxide; water; or a mixture of these solvents, in the presence or absence of organic bases such as triethylamine, pyridine, morpholine, diisopropylethylamine, 4-(N,N-dimethylamino)pyridine and 2,6-di-t-butylpyridine or inorganic bases such as potassium carbonate, sodium carbonate and sodium hydrogen carbonate. Preferably, compound (34) may be prepared by reacting compound [III] with allyl chloroformate for 6 to 18 hours at room temperature, in 1,4-dioxane, in the presence of a saturated aqueous solution of sodium hydrogen carbonate.

Step 31: Compound (35) may be prepared, for example, by reacting compound (34) with an appropriate catalyst such as p-toluenesulfonic acid or oxalic acid, and either with or without using a dehydration apparatus such as a Dean-Stark distillation trap, in an inert solvent, examples of which include hydrocarbon type solvents such as benzene, toluene and hexane; halogen type solvents such as dichloromethane, chloroform and carbon tetrachloride; ether type solvents such as tetrahydrofuran, diethyl ether and 1,2-dimethoxyethane; or a mixture of these solvents, in the presence of an aldehyde such as paraformaldehyde. Preferably, compound (35) may be prepared by heat refluxing compound (34) with paraformaldehyde using a Dean-Stark distillation trap for 1 to 5 hours, in benzene, in the presence of paratoluenesulfonic acid.

Step 32: Compound (36) may be prepared from compound (35) by means of a common esterification reaction (see T. W. Greene, P. G. M. Wuts, "Protective Groups in Organic Synthesis"). It is also possible to prepare compound (36) by reacting the ester moieties of a compound of formula $L^2CHR^cOC(O)ZR^d$ (wherein $L^2$ represents a leaving group, for example, a halogen atom, a tosylsulfonate, a trifluoromethansulfonate or a tolylsulfonate) and of compound (35), in an inert solvent, examples of which include hydrocarbon type solvents such as benzene, toluene, hexane and cyclohexane; halogen type solvents such as dichloromethane, chloroform and carbon tetrachloride; ether type solvents such as tetrahydrofuran, diethyl ether and 1,2-dimethoxyethane; amides such as N,N-dimethylformamide and N-methyl-2-pyrrolidinone; dimethylsulfoxide; or a mixture of these solvents, in the presence of inorganic bases such as sodium hydride, potassium hydride, potassium carbonate, sodium carbonate, sodium hydrogen carbonate, sodium hydroxide and potassium hydroxide; metal amides such as lithium bis(trimethylsilyl)amide, lithium diisopropylamide and sodium amide; organic bases such as triethylamine, pyridine, diisopropylethylamine, 4-(N,N-dimethylamino)pyridine and 2,6-di-t-butylpyridine; or bases such as potassium t-butoxide, in the presence or absence of an appropriate activating agent such as sodium iodide. Preferably, compound (36) may be prepared by reacting compound (35) with $R^1Cl$ for 2 to 24 hours at room temperature to 75° C., in N,N-dimethylformamide, in the presence of sodium iodide.

Step 33: Compound (37), which is the compound of the present invention, may be prepared from compound (36) by deprotecting the α-amino acid moiety, in an inert solvent, examples of which include hydrocarbon type solvents such as benzene, toluene and hexane; halogen type solvents such as dichloromethane, chloroform and carbon tetrachlorid; ether type solvents such as tetrahydrofuran, diethyl ether and 1,2-dimethoxyethan; or a mixture of these solvents, in the presence of a zero-valent palladium catalysts such as tetrakis(triphenylphosphine)palladium(0) and a regeneration reagent of a metal catalyst such as 1,3-dimethylbarbituric acid. Preferably, compound (37) of the present invention may be prepared by deprotecting compound (36) for 30 minutes to 3 hours at room temperature to 50° C., in chloroform, in the presence of tetrakis(triphenylphosphine)palladium and 1,3-dimethylbarbituric acid.

The compounds of the present invention may be made into pharmaceutical formulations or pharmaceutical compositions by being combined with one or more pharmaceutically acceptable carriers, excipients or diluents. Examples of the carriers, excipients and diluents include water, lactose, dextrose, fructose, sucrose, sorbitol, mannitol, polyethylene glycol, propylene glycol, starch, gum, gelatin, arginate, calcium silicate, calcium phosphate, cellulose, water syrup, methylcellulose, polyvinyl pyrrolidone, alkyl parahydroxybenzoate, talc, magnesium stearate, stearic acid, glycerol and oils such as sesame oil, olive oil and soybean oil.

The compounds of the present invention may be formulated by means of common formulation procedures into drugs for oral or parenteral administration, in particular as group II metabotropic glutamate receptor antagonists, in the form of tablets, pills, capsules, granules, powders, liquids, emulsions, suspensions, ointments, injections and skin plasters, after being mixed with the said carriers, excipients or diluents and if necessary, with additives such as commonly employed fillers, binders, disintegrants, pH regulators and solubilizers.

The compounds of the present invention can be administered orally of parenterally to an adult patient in a quantity of 0.01 to 500 mg per day in a single dose or in several doses. Oral administration is preferable from the point of usability and medicinal benefits. The dosage can be increased or decreased as appropriate according to the type of the disease targeted for treatment and the age, weight and symptoms of the patient.

EXAMPLE

The following Reference Examples, Examples and Test Example illustrate the present invention in detail. It should be understood that the present invention is not limited to these examples.

Reference Example 1

Synthesis of (1R,2R,3R,5R,6R)-2-amino-3-(3,4-dichlorobenzyloxy)-6-fluorobicyclo[3.1.0]hexane-2,6-dicarboxylic acid (1) 245 mL of a 2.66M n-butyl lithium hexane solution was added dropwise to 700 mL of a tetrahydrofuran solution containing 137 mL of hexamethyldisilazane, and the mixture was stirred for 1 hour while being maintained at −63° C. to −54° C. 340 mL of a tetrahydrofuran solution containing 101 g of (1R,5R,6R)-6-fluoro-2-oxo-bicyclo[3.1.0]hexane-6-carboxylate ethyl ester was added dropwise thereto while being maintained at −63° C. to −52° C. 700 mL of a tetrahydrofuran solution containing 213 g of N-phenyl-bis(trifluoromethanesulfonimide) was added an hour later at −63° C. to −45° C. The reaction solution was warmed naturally to room temperature and further stirred for 2.5 hours. The reaction solution was diluted with diethyl ether, washed three times with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200 (made by Wako Pure Chemical Industries Ltd.), eluent: hexane-ethyl acetate=30:1 to 20:1 to 5:1). The obtained 175 g of (1R,5R,6R)-6-fluoro-2-trifluoromethanesulfonyloxy-bicyclo[3.1.0]hex-2-en-6-carboxylate ethyl ester was dissolved in 875 mL of N,N-dimethylformamide and 875 mL of ethanol, and after 95.1 mL of diisopropylethylamine, 8.65 g of triphenylphosphine and 3.70 g of palladium acetate were added, the mixture was stirred for 5.5 hours at room temperature under a carbon monoxide atmosphere. 1N hydrochloric acid was added thereto, and the reaction solution was extracted six times with diethyl ether. The organic layers were combined, washed four times with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200 (made by Wako Pure Chemical Industries Ltd.), eluent: hexane-ethyl acetate=30:1 to 20:1 to 10:1), thereby yielding 92.6 g of (1R,5R,6R)-6-fluorobicyclo[3.1.0]hex-2-en-2,6-dicarboxylic acid diethyl ester.

$^1$H-NMR (200 MHz, CDCl$_3$, TMS); 10.31 (t, J=7.03 Hz, 3H), 1.33 (t, J=7.03 Hz, 3H), 2.37-2.51 (m, 1H), 2.65-2.81 (m, 1H), 2.88-3.04 (m, 1H), 3.10 (dd, J=7.47, 2.64 Hz, 1H), 4.12-4.40 (m, 4H), 6.77-6.79 (m, 1H).

MS (ESI)(Pos) m/z; 265 (M+Na)$^+$

[α]$_D^{21}$=+158.0° (CHCl$_3$, c=1.5)

(2) 160 mL of a 50% N-methylmorpholine N-oxide solution and 121 mL of a 5% osmium (VIII) oxide solution was added to 92.4 g of (1R,5R,6R)-6-fluorobicyclo[3.1.0]hexa-2-en-2,6-dicarboxylic acid diethyl ester dissolved in 1.76 L of acetonitrile and 680 mL of water, and the mixture was stirred for 1 hour at room temperature. Sodium sulfite was added thereto at ice cooling, and the reaction solution was stirred for 30 minutes at room temperature and then filtered through celite. A saturated aqueous solution of sodium chloride was added thereto, and the filtrate was extracted twice with ethyl acetate. The organic layers were combined, washed with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=4:1 to 1:1), thereby yielding 95.6 g of (1R,2S,3R,5R,6R)-6-fluoro-2,3-dihydroxybicyclo[3.1.0]hexane-2,6-dicarboxylic acid diethyl ester.

$^1$H-NMR (200 MHz, CDCl$_3$, TMS); 1.31 (t, J=7.25 Hz, 6H), 2.03-2.34 (m, 3H), 2.40-2.55 (m, 1H), 2.70 (d, J=9.23 Hz, 1H), 4.09 (s, 1H), 4.18-4.47 (m, 5H).

MS (ESI)(Nega) m/z; 275 (M−H)$^−$

[α]$_D^{27}$=−69.1° (CHCl$_3$, c=1.4)

(3) 106 mL of triethylamine was added to 1.24 L of a dichloromethane solution containing 95.4 g of (1R,2S,3R,5R,6R)-6-fluoro-2,3-dihydroxybicyclo[3.1.0]hexane-2,6-dicarboxylic acid diethyl ester at ice-cooling, 37.6 mL of thionyl chloride was added dropwise thereto, and the mixture was stirred for 30 minutes. The reaction solution was washed twice with water and with a saturated aqueous solution of sodium chloride, and then dried over anhydrous magnesium sulfate. After the desiccant was filtered off, the filtrate was concentrated under reduced pressure. The residue was dissolved in 640 mL of carbon tetrachloride, 640 mL of acetonitrile and 760 mL of water. 96.0 g of sodium metaperiodate and 655 mg of ruthenium (III) chloride hydrate were added thereto, and the solution was stirred for 1 hour at room temperature. After the mixture was filtered through celite, the filtrate was separated, and the aqueous layer was extracted with diethyl ether. The organic layers were combined, washed with a saturated aqueous solution of sodium chloride, and then dried over anhydrous magnesium sulfate. After the desiccant was filtered off, the filtrate was concentrated under reduced pressure, and the residue was purified by column chromatography (silica gel: Wako gel C200, eluent: hexane-ethyl acetate=4:1), thereby yielding 109 g of (1R,1aR,1bS,4aR,5aR)-1-fluoro-3,3-dioxotetrahydro-2,4-dioxa-3λ$^6$-thiacyclopropa[a]pentalen-1,1b-dicarboxylic acid diethyl ester.

$^1$H-NMR (200 MHz, CDCl$_3$, TMS); 1.33 (t, J=7.03 Hz, 3H), 1.34 (t, J=7.03 Hz, 3H), 2.52-2.94 (m, 4H), 4.23-4.47 (m, 4H), 5.40-5.53 (m, 1H).

MS (ESI)(Pos) m/z; 361 (M+Na)$^+$

[α]$_D^{28}$=+18.3° (CHCl$_3$, c=1.0)

(4) 37.7 g of sodium azide was added to 109 g of (1R,1aR,1bS,4aR,5aR)-1-fluoro-3,3-dioxotetrahydro-2,4-dioxa-3λ$^6$-thiacyclopropa[a]pentalen-1,1b-dicarboxylic acid diethyl ester dissolved in 1.10 L of N,N-dimethylformamide and 110 mL of water, and the mixture was stirred for 14 hours at 50° C. The solvent was distilled under reduced pressure, and after the residue was dissolved in 6.48 L of diethyl ether and 177 mL of water, 516 mL of 20% (V/V) sulfuric acid was added thereto, and the mixture was stirred for 34 hours at room temperature. After the reaction solution was separated, the organic layers were washed twice with a saturated aqueous solution of sodium chloride, and then dried over anhydrous magnesium sulfate. After the desiccant was filtered off the, filtrate was concentrated under reduced pressure, and the residue was purified by column chromatography (silica gel: Wako gel C200, eluent: hexane-ethyl acetate=4:1), thereby yielding 88.5 g of (1R,2R,3R,5R,6R)-2-azide-6-fluoro-3-hydroxybicyclo[3.1.0]hexane-2,6-dicarboxylic acid diethyl ester.

$^1$H-NMR (200 MHz, CDCl$_3$, TMS); 1.33 (t, J=7.03 Hz, 3H), 1.38 (t, J=7.03 Hz, 3H), 2.18-2.61 (m, 5H), 4.21-4.48 (m, 5H).

MS (ESI)(Pos) m/z; 324 (M+Na)$^+$

[α]$_D^{22}$=−48.7° (CHCl$_3$, c=1.0)

(5) 1.36 g of 60% sodium hydride (oily) was washed twice with hexane and suspended in 46 mL of tetrahydrofuran, and then 60.1 g of 3,4-dichlorobenzyl alcohol dissolved in 68 mL of tetrahydrofuran was added dropwise thereto. The mixture was stirred for 30 minutes at room temperature, and 34 mL of trichloroacetonitrile was added dropwise thereto while being cooled with salt-ice. The solution was stirred for 30 minutes at this temperature, 30 minutes at ice-cooling, 30 minutes in a water bath, and a further 2 hours at room temperature. The reaction solution was concentrated under reduced pressure, and after 45 mL of pentane and 1.1 mL of methanol was added thereto, the residue was stirred vigorously for 30 minutes at room temperature. After the inorganic salt was filtered off, the filtrate was concentrated under reduced pressure, thereby yielding 106.8 g of crude 3,4-dichlorobenzyl-2,2,2-trichloroacetimidate.

2.03 g of the crude 3,4-dichlorobenzyl-2,2,2-trichloroacetimidate and 1.27 g of (1R,2R,3R,5R,6R)-2-azide-3-hydroxy-6-fluorobicyclo[3.1.0]hexane-2,6-dicarboxylic acid diethyl ester were dissolved in 5.4 mL of chloroform and 10.8 mL of cyclohexane. After being cooled in an ice bath, 187 μL of trifluoromethane sulfonic acid was added thereto. After the mixture was stirred for 1.5 hours at 30° C., 93 μL of trifluoromethane sulfonic acid was further added thereto, and the mixture was stirred for 1 hour. The inorganic salt was filtered off, and a saturated aqueous solution of sodium hydrogen carbonate was added thereto at ice-cooling. After the solution was extracted twice with chloroform, the organic layers were combined, washed with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=15:1), thereby yielding 771 mg of (1R,2R,3R,5R,6R)-2-azide-3-(3,4-dichlorobenzyloxy)-6-fluorobicyclo[3.1.0]hexane-2,6-dicarboxylic acid diethyl ester.

$^1$H-NMR (200 MHz, CDCl$_3$, TMS); 1.26-1.39 (m, 6H), 2.24-2.51 (m, 4H), 3.91-4.05 (m, 1H), 4.18-4.35 (m, 4H), 4.42 (d, J=11.9 Hz, 1H), 4.64 (d, J=11.9 Hz, 4H), 7.05-7.14 (m, 1H), 7.36-7.43 (m, 2H).

MS (ESI)(Pos) m/z; 482 (M+Na)$^+$ $[\alpha]_D^{24}$=14.5° (CHCl$_3$, c=0.94)

(6) 65.7 mL of a 1M trimethylphosphine/tetrahydrofuran solution was added to 27.5 g of (1R,2R,3R,5R,6R)-2-azide-3-(3,4-dichlorobenzyloxy)-6-fluorobicyclo[3.1.0]hexane-2,6-dicarboxylic acid diester dissolved in 825 mL of tetrahydrofuran and 82.5 mL of water, and the mixture was stirred for 4 hours at room temperature. The mixture was diluted with 825 mL of diethyl ether, washed with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=4:1 to 3:2), thereby yielding 23.1 g of (1R,2R,3R,5R,6R)-2-amino-3-(3,4-dichlorobenzyloxy)-6-fluorobicyclo[3.1.0]hexane-2,6-dicarboxylic acid diethyl ester.

$^1$H-NMR (200 MHz, CDCl$_3$, TMS); 1.24-1.40 (6H, m), 2.02-2.28 (2H, m), 2.51-2.80 (2H, m), 3.98-4.08 (1H, m), 4.18-4.34 (4H, m), 4.43 (1H, d, J=12.5 Hz), 4.53 (1H, d, J=12.5 Hz), 7.10-7.19 (1H, m), 7.36-7.45 (2H, m).

MS (ESI)(Pos) m/z; 456 (M+Na)$^+$ $[\alpha]_D^{22}$=+11.6° (CHCl$_3$, c=0.50%)

(7) 5.53 g of lithium hydroxide hydrate was added to 22.9 g of (1R,2R,3R,5R,6R)-2-amino-3-(3,4-dichlorobenzyloxy)-6-fluorobicyclo[3.1.0]hexane-2,6-dicarboxylic acid diethyl ester dissolved in 480 mL of tetrahydrofuran and 240 mL of water, and the mixture was stirred for three days at room temperature. 443 mg of lithium hydroxide hydrate was further added thereto, and the mixture was stirred for 1 day at room temperature. 169 mL of 1N hydrochloric acid was added dropwise thereto at ice-cooling, and the mixture was stirred for 14 hours at room temperature. The precipitated solids were filtered, and then washed with 200 mL of tetrahydrofuran and 100 mL of water, thereby yielding 12.3 g of (1R,2R,3R,5R,6R)-2-amino-3-(3,4-dichlorobenzyloxy)-6-fluorobicyclo[3.1.0]hexane-2,6-dicarboxylic acid.

$^1$H-NMR (300 MHz, D$_2$O, TMSP); 2.28-2.45 (3H, m), 2.50 (1H, dd, J=7.6, 13.4 Hz), 4.05-4.11 (1H, m), 4.52 (1H, d, J=12.1 Hz), 4.60 (1H, d, J=12.1 Hz), 7.26-7.58 (3H, m).

MS (ESI)(Nega) m/z; 376 (M−H)$^-$ $[\alpha]_D^{27}$=~10.0° (1N NaOH, c=1.02)

Reference Example 2

Synthesis of (1R,2S,3R,5R,6R)-2-amino-3-(3,4-dichlorobenzylsulfanyl)-6-fluorobicyclo[3.1.0]hexane-2,6-dicarboxylic acid (1) 48 μL of pyridine, and 78 μL of trifluoromethane sulfonic acid anhydride dissolved in 0.4 mL of dichloromethane was added dropwise to 120 mg of (1R,2R,3R,5R,6R)-2-azide-6-fluoro-3-hydroxybicyclo[3.1.0]hexane-2,6-dicarboxylic acid diethyl ester dissolved in 20 mL of dichloromethane at −75° C. under a nitrogen atmosphere, and the mixture was stirred for 1.5 hours at ice-cooling. 39 μL of trifluoromethane sulfonic acid anhydride dissolved in 24 μL of pyridine and 0.2 mL of dichloromethane was added dropwise thereto at −75° C., and the mixture was stirred for 25 minutes at ice-cooling. 10 mL of ether was added thereto, and after the solids were filtered off, the filtrate was concentrated under reduced pressure, and the residue was purified by column chromatography (silica gel: Wako gel C200, eluent: hexane-ethyl acetate=5:1), thereby yielding 166 mg of (1R,2R,3R,5R,6R)-2-azide-6-fluoro-3-trifluoromethanesulfonyloxy-bicyclo[3.1.0]hexane-2,6-dicarboxylic acid diethyl ester.

$^1$H-NMR (200 MHz, CDCl$_3$, TMS); 1.35 (t, J=7.0 Hz, 3H), 1.38 (t, J=7.0 Hz, 3H), 2.35-2.50 (m, 2H), 2.62-2.86 (m, 2H), 4.31 (q, J=7.0 Hz, 2H), 4.27-4.55 (m, 2H), 4.94-5.10 (m, 1H).

MS (FAB)(Pos) m/z; 434 (M+H)$^+$ $[\alpha]_D^{26}$=−31.2° (CHCl$_3$, c=0.4)

(2) 688 mg of potassium nitrite and 428 mg of 18-crown-6 ether was added to 701 mg of (1R,2R,3R,5R,6R)-2-azide-6-fluoro-3-trifluoromethanesulfonyloxy-bicyclo[3.1.0]hexane-2,6-dicarboxylic acid diethyl ester dissolved in 6.9 mL of N,N-dimethylformamide, and the mixture was stirred for 1.5 days at room temperature under a nitrogen atmosphere, and further stirred for 3.5 days at 45° C. Water was added thereto, and the mixture was extracted twice with ethyl acetate. The organic layers were combined, washed with a saturated aqueous solution of sodium chloride, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=5:1), thereby yielding 388 mg of (1R,2R,3S,5R,6R)-2-azide-6-fluoro-3-hydroxybicyclo[3.1.0]hexane-2,6-dicarboxylic acid-2,6-diethyl ester.

$^1$H-NMR (200 MHz, CDCl$_3$, TMS); 1.34 (t, J=7.0 Hz, 3H), 1.36 (t, J=7.0 Hz, 3H), 2.16 (dd, J=2.9 Hz, 14.9 Hz, 1H), 2.17-2.30 (m, 1H), 2.44 (dd, J=3.1 Hz, 8.1 Hz, 1H), 2.61 (dd, J=12.3 Hz, 16.0 Hz, 1H), 2.80-2.99 (m, 1H), 4.29 (q, J=7.0 Hz, 2H), 4.34 (q, J=7.0 Hz, 2H), 4.48-4.64 (m, 1H).

MS (ESI)(Pos) m/z; 324 (M+Na)$^+$ $[\alpha]_D^{25}$=+6.4° (CHCl$_3$, c=1.0)

(3) Under a nitrogen atmosphere, 0.36 mL of trifluoromethane sulfonic acid anhydride dissolved in 1.2 mL of dichloromethane was added dropwise to 364 mg of (1R,2R,3S,5R,6R)-2-azide-6-fluoro-3-hydroxybicyclo[3.1.0]hexane-2,6-dicarboxylic acid diethyl ester dissolved in 6.1 mL of dichloromethane and 0.21 mL of pyridine at −77° C. to −69° C. The solution was stirred for 30 minutes at −77° C., and further stirred for 30 minutes at ice-cooling. 30 mL of diethyl ether was added thereto, and after the solids were filtered off, the filtrate was concentrated under reduced pressure. The residue was purified by column chromatography (silica gel: Wako gel C200, eluent: hexane-ethyl acetate=5:1), thereby yielding 487 mg of (1R,2R,3S,5R,6R)-2-azide-6-fluoro-3-trifluoromethanesulfonyloxy-bicyclo[3.1.0]hexane-2,6-dicarboxylic acid diethyl ester.

$^1$H-NMR (200 MHz, CDCl$_3$, TMS); 1.36 (t, J=7.03 Hz, 3H), 1.39 (t, J=7.47 Hz, 3H), 2.26-2.63 (m, 3H), 2.91-3.10 (m, 1H), 4.25-4.45 (m, 4H), 5.57 (dd, J=9.01, 2.86 Hz, 1H).

MS (ESI)(Pos) m/z; 456 (M+Na)$^+$ $[\alpha]_D^{26}$=−41.4 (CHCl$_3$, c=1.1)

(4) 2.59 g of 3,4-dichlorobenzylmercaptan was added to 308 mg of sodium dissolved in 18 mL of ethanol at room temperature under a nitrogen atmosphere, and the mixture was stirred for 5 minutes and then concentrated under reduced pressure. 64 mL of dimethylsulfoxide was added to the filturate, and after 3.23 g of (1R,2R,3S,5R,6R)-2-azide-6-fluoro-3-trifluoromethanesulfonyloxy-bicyclo[3.1.0]hexane-2,6-dicarboxylic acid diethyl ester dissolved in 6.4 mL of dimethylsulfoxide was added thereto at room temperature, the mixture was stirred for ten minutes. 250 mL of diethyl ether was added thereto, and then the upper and lower layers were separated. The lower layer was extracted twice with diethyl ether. The organic layers were combined, washed with a cooled 1N hydrochloric acid and with a saturated aqueous solution of sodium chloride, and then dried over anhydrous sodium sulfate. After the desiccant was filtered off, the filtrate was concentrated under reduced pressure. The residue was purified by column chromatography (silica gel: Wako gel C200, eluent: hexane-ethyl acetate=10:1 to 5:1), thereby yielding 3.35 g of (1R,2S,3R,5R,6R)-2-azide-3-(3,4-dichlorobenzylsulfanyl)-6-fluorobicyclo[3.1.0]hexane-2,6-dicarboxylic acid diethyl ester.

$^1$H-NMR (200 MHz, CDCl$_3$, TMS); 1.34 (t, J=7.03 Hz, 3H), 1.38 (t, J=7.03 Hz, 3H), 2.20-2.49 (m, 4H) 2.99-3.13 (m, 1H), 3.68 (d, J=13.62 Hz, 1H), 3.84 (d, J=13.62 Hz, 1H), 4.22-4.51 (m, 4H), 7.16 (dd, J=8.13, 1.98 Hz, 1H), 7.34-7.46 (m, 2H).

MS (ESI)(Pos) m/z; 498 (M+Na)$^+$ $[\alpha]_D^{24}$=+129.9° (CHCl$_3$, c=0.5)

(5) 7.7 mL of a 1M trimethylphosphine/tetrahydrofuran solution was added to 3.35 g of (1R,2S,3R,5R,6R)-2-azide-3-(3,4-dichlorobenzylsulfanyl)-6-fluorobicyclo[3.1.0]hexane-2,6-dicarboxylic acid diethyl ester dissolved in 100 mL of tetrahydrofuran and 10 mL of water, and the mixture was stirred for 1 hour at room temperature. After the solution was diluted with 200 mL of diethyl ether, 50 mL of a saturated aqueous solution of sodium hydrogen carbonate was added thereto, and the mixture was stirred for 1.5 hours at room temperature. After separation, the organic layers were washed with a saturated aqueous solution of sodium chloride and then dried over anhydrous sodium sulfate. After the desiccant was filtered off, the filtrate was concentrated under reduced pressure. The residue was diluted with chloroform, and silica gel [Wako gel C200] was added thereto. After being concentrated under reduced pressure and then left to stand for 18 hours at room temperature, the residue was purified by column chromatography (silica gel: Wako gel C200, eluent: hexane-ethyl acetate=2:1), thereby yielding 2.78 g of (1R,2S,3R,5R,6R)-2-amino-3-(3,4-dichlorobenzylsulfanyl)-6-fluorobicyclo[3.1.0]hexane-2,6-dicarboxylic acid diethyl ester $^1$H-NMR (300 MHz, CDCl$_3$, TMS); 1.31 (t, J=7.2 Hz, 3H), 1.35 (t, J=7.2 Hz, 3H), 2.08-2.15 (m, 1H), 2.24-2.40 (m, 3H), 2.86-2.93 (m, 1H), 3.73 (d, J=13.4 Hz, 1H), 3.88 (d, J=13.4 Hz, 1H), 4.21-4.37 (m, 4H), 7.15 (dd, J=8.2, 2.2 Hz, 1H), 7.36 (d, J=8.2 Hz, 1H), 7.42 (d, J=2.2 Hz, 1H).

MS (ESI)(Pos) m/z; 472 (M+Na)$^+$ $[\alpha]_D^{26}$=+94.4° (CHCl$_3$, c=0.25)

(6) 12 mg of lithium hydroxide hydrate was added to 41 mg of (1R,2S,3R,5R,6R)-2-amino-3-(3,4-dichlorobenzylsulfanyl)-6-fluorobicyclo[3.1.0]hexane-2,6-dicarboxylic acid diethyl ester dissolved in 0.8 mL of tetrahydrofuran and 0.4 mL of water, and the mixture was stirred for 5.5 days at room temperature. The mixture was adjusted to pH=3 with 1N hydrochloric acid in an ice bath. 30 mL of water was added thereto, and after the mixture was stirred for 1 hour at room temperature and then purified by ion exchange resin (AG 50W-X8 Resin (H form), eluent: water, a 40% aqueous solution of tetrahydrofuran and a 10% aqueous solution of pyridine), the obtained solids were further washed with tetrahydrofuran, thereby yielding 26 mg of (1R,2S,3R,5R,6R)-2-amino-3-(3,4-dichlorobenzylsulfanyl)-6-fluorobicyclo[3.1.0]hexane-2,6-dicarboxylic acid.

$^1$H-NMR (300 MHz, D$_2$O, TMSP); 2.17-2.48 (m, 4H), 3.04-3.13 (m, 1H), 3.80 (d, J=14.9 Hz, 1H), 3.85 (d, J=14.9 Hz, 1H), 7.31 (d, J=8.1 Hz, 1H), 7.53 (d, J=8.1 Hz, 1H), 7.59 (s, 1H).

MS (ESI)(Nega) m/z; 392 (M–H)$^-$ $[\alpha]_D^{30}$=+47.5° (1N NaOH, c=0.41)

Reference Example 3

Synthesis of (1R,2S,3R,5R,6R)-2-amino-3-(3,4-dichlorobenzylsulfinyl)-6-fluorobicyclo[3.1.0]hexane-2,6-dicarboxylic acid (1) 32 mg of 3-chloroperbenzoic acid was added to 73 mg of (1R,2S,3R,5R,6R)-2-azide-3-(3,4-dichlorobenzylsulfanyl)-6-fluorobicyclo[3.1.0]hexane-2,6-dicarboxylic acid diethyl ester dissolved in 1.46 mL of dichloromethane in a dry ice-acetone bath, and the mixture was stirred for 1 hour. The mixture was further stirred for 3.5 hours in an ice bath, and then for 11 hours at room temperature. After 15 mg of 3-chloroperbenzoic acid was further added in a dry ice-acetone bath, the mixture was stirred for 1 hour, and further stirred for 4 hours in an ice bath. The reaction solution was washed with a saturated aqueous solution of sodium hydrogen carbonate and with a saturated aqueous solution of sodium chloride, and then dried over anhydrous sodium sulfate. After the desiccant was filtered off, the filtrate was concentrated under reduced pressure The residue was purified by column chromatography (silica gel: Wako gel C200, eluent: hexane-ethyl acetate=4:1 to 2:1), thereby yielding 63 mg of (1R,2S,3R,5R,6R)-2-azide-3-(3,4-dichlorobenzylsulfinyl)-6-fluorobicyclo[3.1.0]hexane-2,6-dicarboxylic acid diethyl ester and 12 mg of (1R,2S,3R,5R,6R)-2-azide-3-(3,4-dichlorobenzylsulfonyl)-6-fluorobicyclo[3.1.0]hexane-2,6-dicarboxylic acid diethyl ester.

(1R,2S,3R,5R,6R)-2-azide-3-(3,4-dichlorobenzylsulfinyl)-6-fluorobicyclo[3.1.0]hexane-2,6-dicarboxylic acid diethyl ester $^1$H-NMR (200 MHz, CDCl$_3$, TMS); 1.36 (t, J=7.03 Hz, 3H), 1.38 (t, J=7.03 Hz, 3H), 2.33 (dd, J=14.06, 8.35 Hz, 1H), 2.43-2.61 (m, 2H), 2.80-2.97 (m, 1H), 3.11-3.24 (m, 1H), 3.79 (d, J=13.19 Hz, 1H), 4.09 (d, J=13.19 Hz, 1H), 4.25-4.43 (m, 4H), 7.17 (dd, J=8.35, 2.20 Hz, 1H), 7.40-7.50 (m, 2H).

MS (ESI)(Pos) m/z; 514 (M+Na)$^+$ $[\alpha]_D^{28}$=+36.0° (CHCl$_3$, c=0.5)

(1R,2S,3R,5R,6R)-2-azide-3-(3,4-dichlorobenzylsulfonyl)-6-fluorobicyclo[3.1.0]hexane-2,6-dicarboxylic acid diethyl ester $^1$H-NMR (200 MHz, CDCl$_3$, TMS); 1.36 (t, J=7.03 Hz, 3H), 1.39 (t, J=7.03 Hz, 3H), 2.33-2.58 (m, 3H), 2.86-3.05 (m, 1H), 3.53 (dd, J=11.21, 8.13 Hz, 1H), 4.24-4.46 (m, 6H), 7.28 (dd, J=8.35, 2.20 Hz, 1H), 7.44-7.56 (m, 2H).

MS (ESI)(Pos) m/z; 530 (M+Na)$^+$ $[\alpha]_D^{29}$=+7.9° (CHCl$_3$, c=0.7)

(2) By means of the same method as Reference Example 2(5), 41 mg of (1R,2S,3R,5R,6R)-2-amino-3-(3,4-dichlorobenzyl sulfinyl)-6-fluorobicyclo[3.1.0]hexane-2,6-dicarboxylic acid diethyl ester was yielded from 61 mg of (1R,2S,3R,5R,6R)-2-azide-3-(3,4-dichlorobenzylsulfinyl)-6-fluorobicyclo[3.1.0]hexane-2,6-dicarboxylic acid diethyl ester.

$^1$H-NMR (200 MHz, CDCl$_3$, TMS); 1.34 (t, J=7.0 Hz, 3H), 1.35 (t, J=7.0 Hz, 3H), 2.30-2.43 (m, 3H), 2.78-3.12 (m, 2H), 3.80 (d, J=13.2 Hz, 1H), 4.19-4.36 (m, 5H), 7.17 (dd, J=8.4, 2.2 Hz, 1H), 7.44 (d, J=8.4 Hz, 1H), 7.44 (d, J=2.2 Hz, 1H).

MS (ESI)(Pos) m/z; 488 (M+Na)$^+$ $[\alpha]_D^{29}$=+59.1° (CHCl$_3$, c=0.32)

(3) By means of the same method as Reference Example 2(6), 17 mg of (1R,2S,3R,5R,6R)-2-amino-3-(3,4-dichlorobenzylsulfinyl)-6-fluorobicyclo[3.1.0]hexane-2,6-dicarboxylic acid was yielded from 38 mg of (1R,2S,3R,5R,6R)-2-amino-3-(3,4-dichlorobenzylsulfinyl)-6-fluorobicyclo[3.1.0]hexane-2,6-dicarboxylic acid diethyl ester.

$^1$H-NMR (300 MHz, D$_2$O, TMSP); 2.16-2.29 (m, 2H), 2.44-2.49 (m, 1H), 2.77-2.88 (m, 1H), 3.44-3.53 (m, 1H), 4.05 (d, J=13.1 Hz, 1H), 4.26 (d, J=13.1 Hz, 1H), 7.29 (d, J=8.5 Hz, 1H), 7.56 (s, 1H), 7.60 (d, J=8.5 Hz, 1H).

MS (ESI)(Nega) m/z; 408 (M-H)$^-$ $[\alpha]_D^{25}$=+79.7° (1N NaOH, c=0.30)

Reference Example 4

Synthesis of (1R,2S,3R,5R,6R)-2-amino-3-(3,4-dichlorobenzylsulfonyl)-6-fluorobicyclo[3.1.0]hexane-2,6-dicarboxylic acid (1) By means of the same method as Reference Example 2(5), 169 mg of (1R,2S,3R,5R,6R)-2-amino-3-(3,4-dichlorobenzylsulfonyl)-6-fluorobicyclo[3.1.0]hexane-2,6-dicarboxylic acid diethyl ester was yielded from 190 mg of (1R,2S,3R,5R,6R)-2-azide-3-(3,4-dichlorobenzylsulfonyl)-6-fluorobicyclo[3.1.0]hexane-2,6-dicarboxylic acid diethyl ester.

$^1$H-NMR (200 MHz, CDCl$_3$, TMS); 1.34 (t, J=7.0 Hz, 3H), 1.36 (t, J=7.0 Hz, 3H), 2.28-2.42 (m, 3H), 2.83-3.01 (m, 1H), 3.41-3.53 (m, 1H), 4.23-4.37 (m, 6H), 7.28 (dd, J=8.4, 1.8 Hz, 1H), 7.46 (d, J=8.4 Hz, 1H), 7.55 (d, J=1.8 Hz, 1H).

MS (ESI)(Pos) m/z; 482 (M+H)$^+$ $[\alpha]_D^{29}$=+24.0° (CHCl$_3$, c=0.86)

(2) 108 mg of (1R,2S,3R,5R,6R)-2-amino-3-(3,4-dichlorobenzylsulfonyl)-6-fluorobicyclo[3.1.0]hexane-2,6-dicarboxylic acid diethyl ester was stirred in 1.08 mL of 60% sulfuric acid (W/V %) for 3 days at 130° C. The reaction solution was ice-cooled, and neutralized with an aqueous solution of 5N sodium hydroxide. The mixture was stirred for 1 hour at room temperature, and then purified by ion exchange resin (AG 50W-X8 Resin (H form), eluent: water, a 30% aqueous solution of tetrahydrofuran, and a 10% aqueous solution of pyridine), thereby yielding 76 mg of (1R,2S,3R,5R,6R)-2-amino-3-(3,4-dichlorobenzylsulfonyl)-6-fluorobicyclo[3.1.0]hexane-2,6-dicarboxylic acid.

$^1$H-NMR (300 MHz, D$_2$O, TMSP); 2.33-2.45 (m, 3H), 2.82-2.94 (m, 1H), 3.98 (dd, J=10.1, 9.48 Hz, 1H), 4.55 (d, J=15.2 Hz, 1H), 4.60 (d, J=15.3 Hz, 1H), 7.37 (d, J=8.4 Hz, 1H), 7.63 (d, J=8.8 Hz, 1H), 7.64 (s, 1H).

MS (ESI)(Nega) m/z; 424 (M-H)$^-$ $[\alpha]_D^{28}$=-5.1° (1N NaOH, c=0.72)

Reference Example 5

Synthesis of (1R,2R,3R,5R,6R)-2-amino-3-(3,4-dichlorobenzylamino)-6-fluorobicyclo[3.1.0]hexane-2,6-dicarboxylic acid (1) 0.89 mL of a 1M trimethylphosphine/tetrahydrofuran solution was added to 245 mg of (1R,2R,3S,5R,6R)-2-azide-6-fluoro-3-hydroxybicyclo[3.1.0]hexane-2,6-dicarboxylic acid diethyl ester dissolved in 7.0 mL of tetrahydrofuran and 0.7 mL of water, and the mixture was stirred for 12 hours at room temperature. The mixture was diluted with 14 mL of diethyl ether, and after a saturated aqueous solution of sodium hydrogen carbonate was added thereto, the mixture was stirred for 1 hour at room temperature. After separation, the aqueous layer was extracted twice with chloroform. The organic layers were combined, washed with a saturated aqueous solution of sodium chloride, and then dried over anhydrous sodium sulfate. After the desiccant was filtered off, the filtrate was concentrated under reduced pressure. The residue was purified by column chromatography (silica gel: Wako gel C200, eluent: chloroform-ethanol=50:1), thereby yielding 163 mg of (1R,2R,3S,5R,6R)-2-amino-6-fluoro-3-hydroxybicyclo[3.1.0]hexane-2,6-dicarboxylic acid diethyl ester.

$^1$H-NMR (200 MHz, CDCl$_3$, TMS); 1.32 (t, J=7.25 Hz, 6H), 2.07-2.23 (m, 2H), 2.41 (dd, J=8.13, 3.30 Hz, 1H), 2.71-2.91 (m, 1H), 4.10-4.41 (m, 5H).

MS (ESI)(Pos) m/z; 276 (M+H)$^+$ $[\alpha]_D^{25}$=+2.8° (CHCl$_3$, c=1.5)

(2) 0.8 mL of a saturated aqueous solution of sodium hydrogen carbonate and 152 mg of di-t-butyldicarbonate were added to 160 mg of (1R,2R,3S,5R,6R)-2-amino-6-fluoro-3-hydroxybicyclo[3.1.0]hexane-2,6-dicarboxylic acid diethyl ester dissolved in 0.8 mL of tetrahydrofuran, and the mixture was stirred for 4 hours at room temperature. The reaction solution was extracted twice with ethyl acetate. The organic layers were combined, washed with a saturated aqueous solution of sodium chloride, and then dried over anhydrous sodium sulfate. After the desiccant was filtered off, the filtrate was concentrated under reduced pressure. The residue was purified by column chromatography (silica gel: Wako gel C200, eluent: hexane-ethyl acetate=2:1), thereby yielding 214 mg of (1R,2R,3S,5R,6R)-2-t-butoxycarbonylamino-6-fluoro-3-hydroxybicyclo[3.1.0]hexane-2,6-dicarboxylic acid diethyl ester.

$^1$H-NMR (200 MHz, CDCl$_3$, TMS); 1.29 (t, J=7.03 Hz, 3H), 1.30 (t, J=7.03 Hz, 3H), 1.44 (s, 9H), 2.20-2.48 (m, 3H), 2.77-2.98 (m, 2H), 4.07-4.48 (m, 4H), 5.57 (s, 1H).

MS (ESI)(Pos) m/z; 398 (M+Na)$^+$ $[\alpha]_D^{22}$=-14.0° (CHCl$_3$, c=0.9)

(3) By means of the same method as Reference Example 2(1), 1.65 g of (1R,2R,3S,5R,6R)-2-t-butoxycarbonylamino-6-fluoro-3-trifluoromethanesulfonyloxy-bicyclo[3.1.0]hexane-2,6-dicarboxylic acid diethyl ester was yielded from 1.47 g of (1R,2R,3S,5R,6R)-2-t-butoxycarbonylamino-6-fluoro-3-hydroxybicyclo[3.1.0]hexane-2,6-dicarboxylic acid diethyl ester.

$^1$H-NMR (200 MHz, CDCl$_3$, TMS); 1.25-1.41 (m, 6H), 1.44 (s, 9H) 2.13-2.26 (m, 1H), 2.40-2.57 (m, 2H), 2.97-3.20 (m, 1H), 4.14-4.47 (m, 4H), 5.32 (s, 1H), 5.99 (d, J=8.35 Hz, 1H).

MS (ESI)(Nega) m/z; 506 (M-H)$^-$ $[\alpha]_D^{28}$=+79.8° (CHCl$_3$, c=0.5)

(4) 313 mg of sodium azide was added to 1.63 g of (1R,2R,3S,5R,6R)-2-t-butoxycarbonylamino-6-fluoro-3-trifluoromethanesulfonyloxy-bicyclo[3.1.0]hexane-2,6-dicarboxylic acid diethyl ester dissolved in 16.3 mL of N,N-dimethylformamide, and the mixture was stirred for 1 hour at room temperature, and then for 20 hours at 35° C. 104 mg of sodium azide was further added thereto, and the mixture was stirred for 18 hours at 35° C. After being diluted with 50 mL of diethyl ether, the mixture was washed twice with water and then with a saturated aqueous solution of sodium chloride. The organic layers were dried over anhydrous sodium sulfate. After the desiccant was filtered off, the filtrate was concentrated under reduced pressure. The residue was purified by column chromatography (silica gel: Wako gel C200, eluent: hexane-ethyl acetate=5:1), thereby yielding 775 mg of (1R, 2R,3R,5R,6R)-3-azido-2-t-butoxycarbonylamino-6-fluorobicyclo[3.1.0]hexane-2,6-dicarboxylic acid diethyl ester.

$^1$H-NMR (200 MHz, CDCl$_3$, TMS); 1.29 (t, J=7.03 Hz, 3H), 1.33 (t, J=7.03 Hz, 3H), 1.45 (s, 9H), 2.21-2.56 (m, 3H), 2.92 (dd, J=7.69, 2.42 Hz, 1H), 3.78-3.88 (m, 1H), 4.17-4.41 (m, 4H), 5.01 (s, 1H).

MS (ESI)(Pos) m/z; 423 (M+Na)

$[\alpha]_D^{26}$=+0.79° (CHCl$_3$, c=1.4)

(5) By means of the same method as Reference Example 5(1), 553 mg of (1R,2R,3R,5R,6R)-3-amino-2-t-butoxycarbonylamino-6-fluorobicyclo[3.1.0]hexane-2,6-dicarboxylic acid diethyl ester was yielded from 725 mg of (1R,2R,3R,5R,6R)-3-azido-2-t-butoxycarbonylamino-6-fluorobicyclo[3.1.0]hexane-2,6-dicarboxylic acid diethyl ester.

$^1$H-NMR (200 MHz, CDCl$_3$, TMS); 1.30 (t, J=7.03 Hz, 3H), 1.32 (t, J=7.03 Hz, 3H), 1.44 (s, 9H), 2.06-2.27 (m, 2H), 2.40-2.55 (m, 1H), 2.61-2.72 (m, 1H), 3.28-3.47 (m, 1H), 4.17-4.41 (m, 4H), 5.05 (s, 1H).

MS (ESI)(Pos) m/z; 397 (M+Na)$^+$ $[\alpha]_D^{27}$=14.2° (CHCl$_3$, c=1.4)

(6) 42 µL of pyridine and 123 mg of 3,4-dichlorobenzylbromide were added to 175 mg of (1R,2R,3R,5R,6R)-3-amino-2-t-butoxycarbonylamino-6-fluorobicyclo[3.1.0]hexane-2,6-dicarboxylic acid diethyl ester dissolved in 0.88 mL of chloroform at ice-cooling, and the mixture was stirred for 3 days at room temperature. A saturated aqueous solution of sodium chloride was added thereto, and the mixture was extracted five times with chloroform. The organic layers were combined and then dried over anhydrous sodium sulfate. After the desiccant was filtered off, the filtrate was concentrated under reduced pressure. The residue was purified by column chromatography (silica gel: Wako gel C200, eluent: chloroform-ethanol=100:1 to 50:1, followed by hexane-ethyl acetate=5:1), thereby yielding 98 mg of (1R,2R,3R,5R,6R)-2-t-butoxycarbonylamino-3-(3,4-dichlorobenzylamino)-6-fluorobicyclo[3.1.0]hexane-2,6-dicarboxylic acid diethyl ester.

$^1$H-NMR (200 MHz, CDCl$_3$, TMS); 1.23-1.34 (m, 6H), 1.44 (s, 9H), 2.03-2.26 (m, 2H), 2.43 (dd, J=12.97, 7.25 Hz, 1H), 2.83-2.93 (m, 1H), 3.02-3.15 (m, 1H), 3.71 (d, J=13.19 Hz, 1H), 3.80 (d, J=13.19 Hz, 1H), 4.12-4.39 (m, 4H), 4.82 (s, 1H), 7.11 (dd, J=8.13, 1.98 Hz, 1H), 7.33-7.45 (m, 2H).

MS (ESI)(Nega) m/z; 531 (M−H)$^-$ $[\alpha]_D^{27}$=−15.1° (CHCl$_3$, c=0.5)

(7) 2.8 mL of a 4N hydrogen chloride/ethyl acetate solution was added to 28 mg of (1R,2R,3R,5R,6R)-2-t-butoxycarbonylamino-3-(3,4-dichlorobenzylamino)-6-fluorobicyclo[3.1.0]hexane-2,6-dicarboxylic acid diethyl ester, and the mixture was stirred for 6 hours at ice-cooling, and further stirred for 18 hours at room temperature. The reaction solution was ice-cooled, and then neutralized with a saturated aqueous solution of sodium hydrogen carbonate, followed by separation. The aqueous layer was extracted with ethyl acetate. The organic layers were combined, washed with saturated aqueous solution of sodium chloride, and then dried over anhydrous sodium sulfate. After the desiccant was filtered off, the filtrate was concentrated under reduced pressure, thereby yielding 21 mg of (1R,2R,3R,5R,6R)-2-amino-3-(3,4-dichlorobenzylamino)-6-fluorobicyclo[3.1.0]hexane-2,6-dicarboxylic acid diethyl ester.

$^1$H-NMR (200 MHz, CDCl$_3$, TMS); 1.31 (t, J=7.0 Hz, 3H), 1.34 (t, J=6.2 Hz, 3H), 2.03-2.28 (m, 3H), 2.35-2.51 (m, 1H), 2.94-3.08 (m, 1H), 3.77 (s, 2H), 4.16-4.40 (m, 4H), 7.12 (d, J=7.9 Hz, 1H), 7.35 (d, J=7.9 Hz, 1H), 7.40 (s, 1H).

MS (ESI)(Pos) m/z, 433 (M+H)$^+$ $[\alpha]_D^{24}$=−8.4° (CHCl$_3$, c=0.56)

(8) By means of the same method as Reference Example 2(6), 17 mg of (1R,2R,3R,5R,6R)-2-amino-3-(3,4-dichlorobenzylamino)-6-fluorobicyclo[3.1.0]hexane-2,6-dicarboxylic acid was yielded from 28 mg of (1R,2R,3R,5R,6R)-2-amino-3-(3,4-dichlorobenzylamino)-6-fluorobicyclo[3.1.0]hexane-2,6-dicarboxylic acid diethyl ester.

$^1$H-NMR (300 MHz, D$_2$O, TMSP); 2.31-2.77 (m, 4H), 3.59-3.74 (m, 1H), 4.06 (d, J=13.5 Hz, 1H), 4.15 (m, J=13.5 Hz, 1H), 7.35 (d, J=7.77 Hz, 1H), 7.58-7.64 (m, 2H).

MS (ESI)(Nega) 375 (M−H)$^-$ $[\alpha]_D^{27}$=−14.6° (1N NaOH, c=0.29)

Reference Example 6

Synthesis of (1R,2R,3R,5R,6R)-2-amino-3-[N,N-(3,4-dichlorobenzyl)methylamino]-6-fluorobicyclo[3.1.0]hexane-2,6-dicarboxylic acid (1) 71 mg of potassium carbonate and 64 µL of methyl iodide were added to 136 mg of (1R,2R,3R,5R,6R)-2-t-butoxycarbonylamino-3-(3,4-dichlorobenzylamino)-6-fluorobicyclo[3.1.0]hexane-2,6-dicarboxylic acid diethyl ester dissolved in 1.36 mL of N,N-dimethylformamide, and the mixture was stirred for 3 days at room temperature. A saturated aqueous solution of sodium thiosulfate was added thereto, and the mixture was extracted twice with ethyl acetate. The organic layers were combined, washed with a saturated aqueous solution of sodium chloride, and then dried over anhydrous sodium sulfate. After the desiccant was filtered off, the filtrate was concentrated under reduced pressure. The residue was purified by column chromatography (silica gel: Wako gel C200 (made by Wako Pure Chemical Industries Ltd.), eluent: hexane-ethyl acetate=5:1), thereby yielding 126 mg of (1R,2R,3R,5R,6R)-2-t-butoxycarbonylamino-3-[N,N-(3,4-dichlorobenzyl)methylamino]-6-fluorobicyclo[3.1.0]hexane-2,6-dicarboxylic acid diethyl ester.

$^1$H-NMR (200 MHz, CDCl$_3$, TMS); 1.28 (t, J=7.03 Hz, 3H), 1.29 (t, J=7.03 Hz, 3H), 1.43 (s, 9H), 2.11 (s, 3H), 2.16-2.58 (m, 3H), 2.80-3.07 (m, 2H), 3.29 (d, J=13.62 Hz, 1H), 3.78 (d, J=13.62 Hz, 1H), 4.05-4.43 (m, 4H), 4.86 (s, 1H), 7.08 (dd, J=8.35, 1.76 Hz, H), 7.31-7.41 (m, 2H).

MS (ESI)(Pos) m/z; 547 (M+H)$^+$ $[\alpha]_D^2$=−51.9° (CHCl$_3$, c=0.5)

(2) By means of the same method as Reference Example 5(7), 96 mg of (1R,2R,3R,5R,6R)-2-amino-3-[N,N-(3,4-dichlorobenzyl)methylamino]-6-fluorobicyclo[3.1.0]hexane-2,6-dicarboxylic acid diethyl ester was yielded from 124 mg of (1R,2R,3R,5R,6R)-2-t-butoxycarbonylamino-3-[N,N-(3,4-dichlorobenzyl)methylamino]-6-fluorobicyclo[3.1.0]hexane-2,6-dicarboxylic acid diethyl ester.

$^1$H-NMR (300 MHz, CDCl$_3$, TMS); 1.33 (t, J=7.0 Hz, 3H), 1.35 (t, J=7.0 Hz, 3H), 2.06 (s, 3H), 2.03-2.21 (m, 1H), 2.23-2.60 (m, 3H), 2.68-2.84 (m, 1H), 3.22 (d, J=14.1 Hz, 1H), 3.97 (d, J=14.1 Hz, 1H), 4.18-4.32 (m, 4H), 7.07 (dd, J=8.1, 2.0 Hz, 1H), 7.30-7.39 (m, 2H).

MS (ESI)(Pos) m/z; 447 (M+H)$^+$ $[\alpha]_D^{23}$=−24.9° (CHCl$_3$, c=0.84)

(3) By means of the same method as Reference Example 2(6), 62 mg of (1R,2R,3R,5R,6R)-2-amino-3-[N,N-(3,4-dichlorobenzyl)methylamino]-6-fluorobicyclo[3.1.0]hexane-2,6-dicarboxylic acid was yielded from 94 mg of (1R,2R,3R,5R,6R)-2-amino-3-[(3,4-dichlorobenzyl)methylamino]-6-fluorobicyclo[3.1.0]hexane-2,6-dicarboxylic acid diethyl ester.

$^1$H-NMR (300 MHz, D$_2$O, TMSP); 2.31-2.41 (m, 1H), 2.45-2.53 (m, 1H), 2.64 (s, 3H), 2.73-2.82 (m, 2H), 3.72-3.82

(m, 1H), 4.01 (d, J=13.4 Hz, 1H), 4.27 (d, J=13.4 Hz, 1H), 7.35-7.41 (m, 1H), 7.61-7.69 (m, 2H).

MS (ESI)(Nega) m/z; 389 (M–H)$^-$ $[\alpha]_D^{24}$=–35.2° (1N NaOH, c=0.51)

Reference Example 7

Synthesis of (1R,2R,3R,5R,6R)-2-amino-3-(3,4-dichlorobenzoylamino)-6-fluorobicyclo[3.1.0]hexane-2,6-dicarboxylic acid (1) 7.3 μL of pyridine and 14 mg of 3,4-dichlorobenzoyl chloride were added to 17 mg of (1R,2R,3R,5R,6R)-3-amino-2-t-butoxycarbonylamino-6-fluorobicyclo[3.1.0]hexane-2,6-dicarboxylic acid diethyl ester dissolved in 0.17 mL of chloroform, and the mixture was stirred for 3 hours at room temperature. The reaction solution was concentrated under reduced pressure. The residue was purified by column chromatography (silica gel: Wako gel C200, eluent: chloroform-ethanol=100:1), thereby yielding 21 mg of (1R,2R,3R,5R,6R)-2-t-butoxycarbonylamino-3-(3,4-dichlorobenzoylamino)-6-fluorobicyclo[3.1.0]hexane-2,6-dicarboxylic acid diethyl ester $^1$H-NMR (200 MHz, CDCl$_3$, TMS); 1.19 (t, J=7.03 Hz, 3H), 1.31 (t, J=7.25 Hz, 3H), 1.41 (s, 9H), 2.21-2.64 (m, 3H), 2.82-2.91 (m, 1H), 4.07-4.37 (m, 4H), 4.58-4.75 (m, 1H), 6.20 (s, 1H), 6.39-6.50 (m, 1H), 7.46-7.57 (m, 2H), 7.80-7.85 (m, 1H).

MS (ESI)(Nega) m/z; 545 (M–H)$^-$ $[\alpha]_D^{23}$=+12.1° (CHCl$_3$, c=0.9)

(2) By means of the same method as Reference Example 5(7), 85 mg of (1R,2R,3R,5R,6R)-2-amino-3-(3,4-dichlorobenzoylamino)-6-fluorobicyclo[3.1.0]hexane-2,6-dicarboxylic acid diethyl ester was yielded from 107 mg of (1R,2R,3R,5R,6R)-2-t-butoxycarbonylamino-3-(3,4-dichlorobenzoylamino)-6-fluorobicyclo[3.1.0]hexane-2,6-dicarboxylic acid diethyl ester.

$^1$H-NMR (200 MHz, CDCl$_3$, TMS); 1.30 (t, J=6.8 Hz, 3H), 1.33 (t, J=7.0 Hz, 3H), 2.09-2.43 (m, 3H), 2.53-2.38 (m, 1H), 4.19-4.38 (m, 4H), 4.52-4.71 (m, 1H), 7.48-7.55 (m, 2H), 7.75-7.84 (m, 1H).

MS (ESI)(Pos) m/z; 469 (M+Na)$^+$ $[\alpha]_D^{27}$=+8.3° (CHCl$_3$, c=0.93)

(3) By means of the same method as Reference Example 2(6), 24 mg of (1R,2R,3R,5R,6R)-2-amino-3-(3,4-dichlorobenzoylamino)-6-fluorobicyclo[3.1.0]hexane-2,6-dicarboxylic acid was yielded from 48 mg of (1R,2R,3R,5R,6R)-2-amino-3-(3,4-dichlorobenzoylamino)-6-fluorobicyclo[3.1.0]hexane-2,6-dicarboxylic acid diethyl ester.

$^1$H-NMR (300 MHz, D$_2$O, TMSP); 2.33-2.42 (m, 2H), 2.57-2.67 (m, 2H), 4.46-4.55 (m, 1H), 7.58-7.68 (m, 2H), 7.87-7.90 (m, 1H).

MS (ESI)(Nega) m/z; 389 (M–H)$^-$ $[\alpha]_D^{28}$=+6.0° (CHCl$_3$, c=0.34)

Reference Example 8

Synthesis of (1R,2R,3R,5R,6R)-2-amino-3-(3,4-dichlorobenzoyloxy)-6-fluorobicyclo[3.1.0]hexane-2,6-dicarboxylic acid (1) 234 mg of 3,4-dichlorobenzoyl chloride was added to 202 mg of (1R,2R,3R,5R,6R)-2-azide-6-fluoro-3-hydroxybicyclo[3.1.0]hexane-2,6-dicarboxylic acid 2-benzyl ester 6-ethyl ester dissolved in 3.7 mL of pyridine, and the mixture was stirred for 28 hours at room temperature under a nitrogen atmosphere. 100 mL of ethyl acetate was added to the reaction solution, and the ethyl acetate solution was washed with a saturated aqueous solution of copper sulfate and with water, and then dried over anhydrous sodium sulfate. After the desiccant was filtered off, the filtrate was concentrated under reduced pressure, and the residue was purified by column chromatography (silica gel: Wako gel C200, eluent: hexane-ethyl acetate=10:1), thereby yielding 298 mg of (1R,2R,3R,5R,6R)-2-azide-3-(3,4-dichlorobenzoyloxy)-6-fluorobicyclo[3.1.0]hexane-2,6-dicarboxylic acid 2-benzyl ester 6-ethyl ester.

$^1$H-NMR (200 MHz, CDCl$_3$); 1.35 (t, J=7.3 Hz, 3H), 2.35-2.55 (m, 3H), 2.77-2.87 (m, 1H), 4.31 (q, J=7.3 Hz, 2H), 5.24-5.46 (m, 3H), 7.28-7.60 (m, 6H), 7.90-8.20 (m, 2H).

MS (ESI)(Pos) m/z; 558 (M+Na)$^+$ (2) By means of the same method as Reference Example 2(5), 218 mg of (1R,2R,3R,5R,6R)-2-amino-3-(3,4-dichlorobenzoyloxy)-6-fluorobicyclo[3.1.0]hexane-2,6-dicarboxylic acid 2-benzyl ester 6-ethyl ester was yielded from 298 mg of (1R,2R,3R,5R,6R)-2-azide-3-(3,4-dichlorobenzoyloxy)-6-fluorobicyclo[3.1.0]hexane-2,6-dicarboxylic acid 2-benzyl ester 6-ethyl ester.

$^1$H-NMR (200 MHz, CDCl$_3$, TMS); 1.33 (t, J=7.3 Hz, 3H), 2.25-2.80 (m, 4H), 4.28 (q, J=7.3 Hz, 2H), 5.05-5.13 (m, 1H), 5.16 (d, J=12.3 Hz, 1H), 5.31 (d, J=12.3 Hz, 1H), 7.24-7.36 (m, 5H), 7.44 (d, J=8.4 Hz, 1H), 7.57 (dd, J=8.4, 2.20 Hz, 1H), 7.90 (d, J=2.2 Hz, 1H).

MS (ESI)(Pos) m/z; 532 (M+Na)$^+$ $[\alpha]_D^{22}$=+31.8° (CHCl$_3$, c=0.55)

(3) 15 mg of 5% palladium carbon was added to 218 mg of (1R,2R,3R,5R,6R)-2-amino-3-(3,4-dichlorobenzoyloxy)-6-fluorobicyclo[3.1.0]hexane-2,6-dicarboxylic acid 2-benzyl ester 6-diethyl ester dissolved in 10 mL of ethanol, and the mixture was stirred for 50 minutes at room temperature under a hydrogen atmosphere. After the palladium carbon was filtered off through celite, the filtrate was concentrated under reduced pressure, and the obtained solids were dissolved in a mixture of 2 mL of tetrahydrofuran and 1 mL of water. 10 mg of lithium hydroxide monohydrate was added thereto at ice-cooling, and the mixture was stirred for 30 minutes. 0.5 mL of 1N hydrochloric acid was further added thereto, and after being diluted to 50 mL with water, the mixture was purified by ion exchange resin (AG 50W-X8 Resin (H form), eluent: water, a 40% aqueous solution of tetrahydrofuran and a 10% aqueous solution of pyridine), thereby yielding 25 mg of (1R,2R,3R,5R,6R)-2-amino-3-(3,4-dichlorobenzoyloxy)-6-fluorobicyclo[3.1.0]hexane-2,6-dicarboxylic acid.

$^1$H-NMR (300 MHz, D$_2$O, TMSP); 2.40-2.45 (m, 2H), 2.71-2.77 (m, 2H), 5.28-5.36 (m, 1H), 7.68 (d, J=8.5 Hz, 1H), 7.89 (d, J=8.5 Hz, 1H), 8.16 (s, 1H).

MS (ESI)(Nega) m/z; 390 (M–H)$^-$ $[\alpha]_D^{28}$=+9.20 (MeOH, c=0.23)

Example 1

Synthesis of (1R,2R,3R,5R,6R)-2-amino-3-(3,4-dichlorobenzyloxy)-6-fluorobicyclo[3.1.0]hexane-2,6-dicarboxylic acid 6-methyl ester hydrochloride 0.65 mL of thionyl chloride was added to 800 mg of (1R,2R,3R,5R,6R)-2-amino-3-(3,4-dichlorobenzyloxy)-6-fluorobicyclo[3.1.0]hexane-2,6-dicarboxylic acid suspended in 8 mL of methanol at ice-cooling, and the mixture was stirred for 4 hours at 50° C. The mixture was further stirred for 3 hours at room temperature, and methanol was distilled under reduced pressure. After 20 mL of hexane was added to the residue, the mixture was stirred for 2 hours, and then the solids were filtered. The solids were washed with diisopropyl ether and hexane, thereby yielding 820 mg of (1R,2R,3R,5R,6R)-2-amino-3-(3,4-dichlorobenzyloxy)-6-fluorobicyclo[3.1.0]hexane-2,6-dicarboxylic acid 6-methyl ester hydrochloride.

Example 2

Synthesis of (1R,2R,3R,5R,6R)-2-amino-3-(3,4-dichlorobenzyloxy)-6-fluorobicyclo[3.1.0]hexane-2,6-dicarboxylic acid 6-pentyl ester 225 μL of thionyl chloride was added to 300 mg of (1R,2R,3R,5R,6R)-2-amino-3-(3,4-dichlorobenzyloxy)-6-fluorobicyclo[3.1.0]hexane-2,6-dicarboxylic acid suspended in 4 mL of pentanol at ice-cooling, and the mixture was stirred for 3 hours at 50° C. After standing to cool, the reaction solution was concentrated to about 1 mL under reduced pressure, 200 mL of hexane was added thereto, and the mixture was stirred for 12 hours. After the precipitated solids were filtered, the residue was purified by reverse phase column chromatography (Wako gel 50C18 (made by Wako Pure Chemical Industries Ltd.), eluent: water to a 50% aqueous solution of acetonitrile), thereby yielding 188 mg of (1R,2R,3R,5R,6R)-2-amino-3-(3,4-dichlorobenzyloxy)-6-fluorobicyclo[3.1.0]hexane-2,6-dicarboxylic acid 6-pentyl ester.

Example 3

Synthesis of (1R,2R,3R,5R,6R)-2-amino-3-(3,4-dichlorobenzyloxy)-6-fluorobicyclo[3.1.0]hexane-2,6-dicarboxylic acid diethoxycarbonylmethyl ester 4.4 mg of lithium hydroxide hydrate was added to 36 mg of (1R,2R,3R,5R,6R)-2-amino-3-(3,4-dichlorobenzyloxy)-6-fluorobicyclo[3.1.0]hexane-2,6-dicarboxylic acid suspended in a mixture of 0.8 mL of tetrahydrofuran and 0.4 mL of water at room temperature, and the mixture was stirred for 10 minutes. After the mixture was concentrated under reduced pressure, 0.36 mL of N,N-dimethylformamide and 21 μL of ethyl bromoacetate were added to the residue, and then the mixture was stirred for 2 hours at room temperature, 2 hours at 50° C. and 4 hours at 90° C. Water was added thereto, and the reaction solution was extracted with ethyl acetate. The organic layers were dried over anhydrous sodium sulfate. After the desiccant was filtered off, the filtrate was concentrated under reduced pressure. The residue was purified by thin layer chromatography (silica gel: 60F$_{254}$ (made by Merck & Co., Inc), eluent: hexane-ethyl acetate=1:1), thereby yielding 12 mg of (1R,2R,3R,5R,6R)-2-amino-3-(3,4-dichlorobenzyloxy)-6-fluorobicyclo[3.1.0]hexane-2,6-dicarboxylic acid diethoxycarbonylmethyl ester.

Example 4

Synthesis of (1R,2R,3R,5R,6R)-2-amino-3-(3,4-dichlorobenzyloxy)-6-fluorobicyclo[3.1.0]hexane-2,6-dicarboxylic acid 6-(2-azidoethyl) ester 6 mg of sodium azide was added to 18 mg of (1R,2R,3R,5R,6R)-2-amino-3-(3,4-dichlorobenzyloxy)-6-fluorobicyclo[3.1.0]hexane-2,6-dicarboxylic acid 6-(2-iodoethyl) ester dissolved in a mixture of 0.2 mL of N,N-dimethylformamide and 0.02 mL of water at room temperature, and the mixture was stirred for 12 hours at 60° C. After standing to cool, the solvent was distilled under reduced pressure, and the residue was purified by reverse phase column chromatography (Wako gel 50C18, eluent: water to a 70% aqueous solution of acetonitrile), thereby yielding 7 mg of (1R,2R,3R,5R,6R)-2-amino-3-(3,4-dichlorobenzyloxy)-6-fluorobicyclo[3.0]hexane-2,6-dicarboxylic acid 6-(2-azidoethyl) ester.

Example 5

Synthesis of (1R,2R,3R,5R,6R)-2-amino-3-(3,4-dichlorobenzyloxy)-6-fluorobicyclo[3.1.0]hexane-2,6-dicarboxylic acid 6-(2-aminoethyl) ester 20 μL of a 1M trimethylphosphine/tetrahydrofuran solution was added to 6 mg of (1R,2R,3R,5R,6R)-2-amino-3-(3,4-dichlorobenzyloxy)-6-fluorobicyclo[3.1.0]hexane-2,6-dicarboxylic acid 6-(2-azidoethyl) ester dissolved in a mixture of 0.15 mL of tetrahydrofuran and 0.02 mL of water at room temperature, and the mixture was stirred for 13 hours. After the solvent was distilled under reduced pressure, the residue was purified by reverse phase column chromatography (Wako gel 50C18 (made by Wako Pure Chemical Industries Ltd.), eluent: water to a 50% aqueous solution of acetonitrile), and the obtained solids were further washed with tetrahydrofuran, thereby yielding 2 mg of (1R,2R,3R,5R,6R)-2-amino-3-(3,4-dichlorobenzyloxy)-6-fluorobicyclo[3.1.0]hexane-2,6-dicarboxylic acid 6-(2-aminoethyl) ester.

The structure and physical data of the compounds described in Examples 1, 2, 3, 4 and 5, as well as those of compounds yielded by means of the same methods are shown in table 1 below.

TABLE 1

The structure and pysical data of the compounds described in Examples 1, 2, 3, 4 and 5

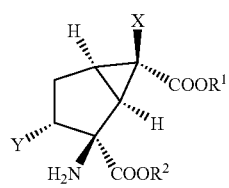

| No. | X | Y | R$^1$ | R$^2$ | NMR (TMS) | MS | Example |
|---|---|---|---|---|---|---|---|
| 1*$^1$ | F | Cl-⟨benzyl⟩-O (3,4-dichlorobenzyloxy) | Me | H | (200 MHz, CD$_3$OD) 2.37-2.63 (m, 4 H) 3.81 (s, 3 H) 4.03-4.18 (m, 1 H) 4.55 (s, 2 H) 7.26 (dd, J = 8.3, 1.8 Hz, 1 H) 7.48 (d, J = 8.3 Hz, 1 H) 7.53 (d, J = 1.8 Hz, 1 H) | ESI (Nega) 390 (M − H)$^-$ | 1 |

TABLE 1-continued

The structure and pysical data of the compounds described in Examples 1, 2, 3, 4 and 5

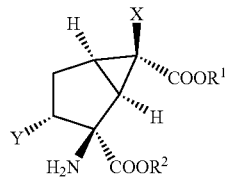

| No. | X | Y | R¹ | R² | NMR (TMS) | MS | Example |
|---|---|---|---|---|---|---|---|
| 2*¹ | F | 3,4-diClC₆H₃CH₂O | n-Pr | H | (200 MHz, CD₃OD) 0.96 (t, J = 6.8 Hz, 3 H) 1.69 (sextet, J = 6.8 Hz, 2 H) 2.37-2.65 (m, 4 H) 4.02-4.12 (m, 1 H) 4.17 (t, J = 6.6 Hz, 2 H) 4.51 (d, J = 11.9 Hz, 1 H) 4.59 (d, J = 11.9 Hz, 1 H) 7.27 (dd, J = 8.4, 1.8 Hz, 1 H) 7.48 (d, J = 8.4 Hz, 1 H) 7.54 (d, J = 1.8 Hz, 1 H) | ESI (Nega) 418 (M − H)⁻ | 1 |
| 3*¹ | F | 3,4-diClC₆H₃CH₂O | i-Pr | H | (500 MHz, CD₃OD) 1.28 (d, J = 5.8 Hz, 6 H) 2.38-2.44 (m, 2 H) 2.54-2.62 (m, 2 H) 4.07-4.12 (m, 1 H) 4.53 (d, J = 11.6 Hz) 4.57 (d, J = 11.6 Hz) 5.07-5.12 (m, 1 H) 7.26 (dd, J = 1.8, 8.6 Hz, 1 H) 7.48 (d, J = 8.6 Hz, 1 H) 7.52 (d, J = 1.8 Hz, 1 H) | ESI (Nega) 418 (M − H)⁻ | 1 |
| 4*¹ | F | 3,4-diClC₆H₃CH₂O | n-Bu | H | (500 MHz, CD₃OD) 0.95 (t, J = 7.9 Hz, 3 H) 1.40 (sextet, J = 7.9 Hz, 2 H) 1.65 (quintet, J = 7.9 Hz, 2 H) 2.38-2.44 (m, 2 H) 2.53-2.62 (m, 2 H) 4.06-4.10 (m, 1 H) 4.22 (t, J = 6.7 Hz, 2 H) 4.52 (d, J = 11.6 Hz, 1 H) 4.58 (d, J = 11.6 Hz, 1 H) 7.26 (dd, J = 1.8, 7.9 Hz, 1 H) 7.47 (d, J = 7.9 Hz, 1 H) 7.53 (d, J = 1.8 Hz, 1 H). | ESI (Nega) 432 (M − H)⁻ | 1 |
| 5*¹ | F | 3,4-diClC₆H₃CH₂O | i-Bu | H | (300 MHz, CD₃OD) 0.95 (d, J = 6.7 Hz, 6 H) 1.90-2.03 (m, 1 H) 2.35-2.66 (m, 4 H) 4.00 (d, J = 6.5 Hz, 2 H) 4.03-4.20 (m, 1 H) 4.52 (d, J = 10.7 Hz, 1 H) 4.58 (d, J = 10.7 Hz, 1 H) 7.26 (dd, J = 8.2, 1.9 Hz, 1 H) 7.47 (d, J = 8.2 Hz, 1 H) 7.53 (d, J = 1.9 Hz, 1 H) | ESI (Nega) 432 (M − H)⁻ | 2 |
| 6 | F | 3,4-diClC₆H₃CH₂O | n-Pentyl | H | (300 MHz, CD₃OD) 0.88-0.96 (m, 3 H) 1.29-1.45 (m, 4 H) 1.63-1.72 (m, 2 H) 2.33-2.64 (m, 4 H) 3.99-4.06 (m, 1 H) 4.20 (t, J = 6.6 Hz, 2 H) 4.48 (d, J = 11.2 Hz, 1 H) 4.60 (d, J = 11.2 Hz, 1 H) 7.29 (dd, J = 8.2, 2.0 Hz, 1 H) 7.46 (d, J = 8.2 Hz, 1 H) 7.55 (d, J = 2.0 Hz, 1 H) | ESI (Nega) 446 (M − H)⁻ | 2 |
| 7 | F | 3,4-diClC₆H₃CH₂O | n-Decyl | H | (300 MHz, CD₃OD) 0.87-0.92 (m, 3 H) 1.23-1.41 (m, 14 H) 1.60-1.71 (m, 2 H) 2.31-2.65 (m, 4 H) 3.97-4.07 (m, 1H) 4.19 (t, J = 6.6 Hz, 2 H) 4.47 (d, J = 12.0 Hz, 1 H) 4.59 (d, J = 12.0 Hz, 1 H) 7.28 (dd, J = 8.0, 2.3 Hz, 1 H) 7.45 (d, J = 8.0 Hz, 1 H) 7.54 (d, J = 2.3 Hz, 1 H) | ESI (Nega) 516 (M − H)⁻ | 2 |

TABLE 1-continued

The structure and pysical data of the compounds described in Examples 1, 2, 3, 4 and 5

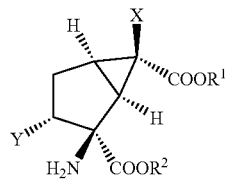

| No. | X | Y | R¹ | R² | NMR (TMS) | MS | Example |
|---|---|---|---|---|---|---|---|
| 8*¹ | F | 3,4-dichlorobenzyloxy | Cyclohexyl | H | (500 MHz, CD₃OD) 1.29-1.59 (m, 6 H) 1.71-1.76 (m, 2 H) 1.85-1.90 (m, 2 H) 2.39-2.45 (m, 2 H) 2.55-2.63 (m, 2 H) 4.08-4.12 (m, 1 H) 4.53 (d, J = 12.2 Hz, 1 H) 4.57 (d, J = 12.2 Hz, 1 H) 7.26 (dd, J = 1.8, 8.6 Hz, 1 H) 7.48 (d, J = 8.6 Hz, 1 H) 7.52 (d, J = 1.8 Hz, 1 H) | ESI (Nega) 472 (M − H)− | 1 |
| 9*¹ | F | 3,4-dichlorobenzyloxy | CH₂-Cyclohexyl | H | (500 MHz, CD₃OD) 0.97-1.05 (m, 2 H) 1.16-1.33 (m, 3 H) 1.63-1.77 (m, 6 H) 2.40-2.46 (m, 2 H) 2.58-2.60 (m, 2 H) 4.03 (d, J = 6.7 Hz, 2 H) 4.09-4.13 (m, 1 H) 4.54 (d, J = 11.6 Hz, 1 H) 4.58 (d, J = 11.6 Hz, 1 H) 7.26 (dd, J = 1.8, 8.6 Hz, 1 H) 7.48 (d, J = 8.6 Hz, 1 H) 7.52 (d, J = 1.8 Hz, 1 H) | ESI (Nega) 472 (M − H)− | 1 |
| 10 | F | 3,4-dichlorobenzyloxy | Benzyl | H | (300 MHz, CD₃OD) 2.30-2.61 (m, 4 H) 3.95-4.05 (m, 1 H) 4.46 (d, J = 11.8 Hz, 1 H) 4.58 (d, J = 11.8 Hz, 1 H) 5.23 (s, 2 H) 7.28 (dd, J = 8.2, 1.9 Hz, 1 H) 7.33-7.41 (m, 5 H) 7.45 (d, J = 8.2 Hz, 1 H) 7.53 (d, J = 1.9 Hz, 1 H) | ESI (Nega) 466 (M − H)− | 2 |
| 11 | F | 3,4-dichlorobenzyloxy | CH₂-CH=CH₂ | H | (300 MHz, CD₃OD) 2.26-2.66 (m, 4 H) 3.99-4.08 (m, 1 H) 4.47 (d, J = 11.8 Hz, 1 H) 4.59 (d, J = 11.8 Hz, 1 H) 4.69 (d, J = 5.7 Hz, 2 H) 5.22-5.41 (m, 2 H) 5.87-6.03 (m, 1 H) 7.28 (dd, J = 8.2, 1.7 Hz, 1 H) 7.45 (d, J = 8.2 Hz, 1 H) 7.54 (d, J = 1.7 Hz, 1 H) | ESI (Nega) 416 (M − H)− | 2 |
| 12 | F | 3,4-dichlorobenzyloxy | H₂C-C≡C-H | H | (300 MHz, CD₃OD) 2.33-2.68 (m, 4 H) 2.99-3.05 (m, 1 H) 3.97-4.10 (m, 1 H) 4.48 (d, J = 12.0 Hz, 1 H) 4.60 (d, J = 12.0 Hz, 1 H) 7.24-7.33 (m, 1 H) 7.42-7.58 (m, 2 H) | ESI (Nega) 414 (M − H)− | 2 |
| 13 | F | 3,4-dichlorobenzyloxy | CH₂CH₂Cl | H | (300 MHz, CD₃OD) 2.36-2.68 (m, 4 H) 3.75-3.81 (m, 2 H) 3.99-4.08 (m, 1 H) 4.41-4.50 (m, 3 H) 4.61 (d, J = 12.0 Hz, 1 H) 7.29 (dd, J = 8.2, 2.0 Hz, 1 H) 7.46 (d, J = 8.2 Hz, 1 H) 7.55 (d, J = 2.0 Hz, 1 H) | ESI (Nega) 438 (M − H)− | 2 |
| 14 | F | 3,4-dichlorobenzyloxy | CH₂CH₂Br | H | (300 MHz, CD₃OD) 2.36-2.96 (m, 4 H) 3.62 (t, J = 5.4 Hz, 2 H) 3.98-4.07 (m, 1 H) 4.48 (d, J = 11.7 Hz, 1 H) 4.50 (t, J = 5.4 Hz, 2 H) 4.60 (d, J = 11.7 Hz, 1 H) 7.25-7.32 (m, 1 H) 7.43-7.57 (m, 2 H) | ESI (Nega) 482 (M − H)− | 2 |

TABLE 1-continued

The structure and pysical data of the compounds described in Examples 1, 2, 3, 4 and 5

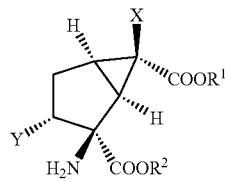

| No. | X | Y | R¹ | R² | NMR (TMS) | MS | Example |
|---|---|---|---|---|---|---|---|
| 15 | F | 3,4-diCl-C₆H₃-CH₂-O-CH₂-CH₂- | -CH₂CH₂I | H | (300 MHz, CD₃OD) 2.41-2.67 (m, 4 H) 3.40 (t, J = 6.6 Hz, 2 H) 4.00-4.09 (m, 1 H) 4.40-4.63 (m, 4 H) 7.30 (dd, J = 8.6, 1.8 Hz, 1 H) 7.47 (d, J = 8.6 Hz, 1 H) 7.56 (d, J = 1.8 Hz, 1 H) | ESI (Pos) 532 (M + H)⁻ | 2 |
| 16 | F | 3,4-diCl-C₆H₃-CH₂-O-CH₂- | -CH₂CH₂OH | H | (300 MHz, CD₃OD) 2.36-2.66 (m, 4 H) 3.71-3.78 (m, 2 H) 3.98-4.07 (m, 1 H) 4.22-4.28 (m, 2 H) 4.48 (d, J = 12.0 Hz, 1 H) 4.59 (d, J = 12.0 Hz, 1 H) 7.28 (dd, J = 8.3, 1.9 Hz, 1 H) 7.45 (d, J = 8.3 Hz, 1 H) 7.54 (d, J = 1.9 Hz, 1 H) | ESI (Nega) 420 (M − H)⁻ | 2 |
| 17 | F | 3,4-diCl-C₆H₃-CH₂-O- | -CH₂-COOEt | *2 | (200 MHz, CDCl₃) 1.29 (t, J = 7.3 Hz, 6 H) 2.25-2.61 (m, 4 H) 3.75-3.91 (m, 1 H) 4.23 (q, J = 7.3 Hz, 4 H) 4.43-4.87 (m, 6 H) 7.08 (dd, J = 7.9, 2.2 Hz, 1 H) 7.34-7.42 (m, 2 H) | ESI (Pos) 572 (M + Na)⁺ | 3 |
| 18 | F | 3,4-diCl-C₆H₃-CH₂-O- | -CH₂CH₂N₃ | H | (300 MHz, CD₃OD) 2.19-2.63 (m, 4 H) 3.48-3.61 (m, 2 H) 3.80-3.98 (m, 1 H) 4.28-4.37 (m, 2 H) 4.48 (d, J = 12.3 Hz, 1 H) 4.66 (d, J = 12.3 Hz, 1 H) 7.25-7.33 (m, 1 H) 7.41-7.48 (m, 1 H) 7.53-7.57 (m, 1 H) | ESI (Nega) 445 (M − H)⁻ | 4 |
| 19 | F | 3,4-diCl-C₆H₃-CH₂-O- | -CH₂CH₂NH₂ | H | (300 MHz, CD₃OD) 2.12-2.65 (m, 4 H) 3.34-3.45 (m, 2 H) 3.57-3.69 (m, 2 H) 3.81-3.96 (m, 1 H) 4.49 (d, J = 12.1 Hz, 1 H) 4.65 (d, J = 12.1 Hz, 1 H) 7.25-7.35 (m, 1 H) 7.42-7.48 (m, 1 H) 7.53-7.58 (m, 1 H) | ESI (Nega) 419 (M − H)⁻ | 5 |
| 20 | H | 3,4-diCl-C₆H₃-CH₂-O- | Et | H | (300 MHz, CD₃OD) 1.24 (t, J = 7.1 Hz, 3 H) 1.97-2.01 (m, 1 H) 2.15-2.51 (m, 4 H) 3.76-3.80 (m, 1 H) 4.13 (q, J = 7.20 Hz, 2 H) 4.50 (s, 2 H) 7.24 (dd, J = 8.2, 1.9 Hz, 1 H) 7.48 (d, J = 8.2 Hz, 1 H) 7.51 (d, J = 1.9 Hz, 1 H). | ESI (Nega) 386 (M − H)⁻ | 2 |
| 21 | F | 3,4-diCl-C₆H₃-CH₂-S- | i-Pr | H | (300 MHz, CD₃OD) 1.26 (d, J = 7.0 Hz, 6 H) 2.21-2.38 (m, 3 H) 2.50-2.63 (m, 1 H) 2.99-3.11 (m, 1 H) 3.76 (d, J = 12.9 Hz, 1 H) 3.81 (d, J = 12.9 Hz, 1 H) 5.00-5.13 (m, 1 H) 7.24-7.32 (m, 1 H) 7.42-7.56 (m, 2 H) | ESI (Pos) 458 (M + Na)⁺ | 2 |

TABLE 1-continued

The structure and pysical data of the compounds described in Examples 1, 2, 3, 4 and 5

| No. | X | Y | R¹ | R² | NMR (TMS) | MS | Example |
|---|---|---|---|---|---|---|---|
| 22 | F | 3,4-dichlorobenzyl-S- | i-Bu | H | (300 MHz, CD$_3$OD) 0.94 (d, J = 6.7 Hz, 6 H) 1.86-1.99 (m, 1 H) 2.23-2.62 (m, 4 H) 2.99-3.08 (m, 1 H) 3.76 (d, J = 13.0 Hz, 1 H) 3.81 (d, J = 13.0 Hz, 1 H) 3.96 (d, J = 6.7 Hz, 2 H) 7.27 (dd, J = 8.4, 1.9 Hz, 1 H) 7.45 (d, J = 8.4 Hz, 1 H) 7.52 (d, J = 2.0 Hz, 1 H) | ESI (Pos) 472 (M + Na)⁺ | 2 |
| 23 | F | 3,4-dichlorobenzyl-S- | n-decyl | H | (300 MHz, CD$_3$OD) 0.89-0.98 (m, 3 H) 1.21-1.45 (m, 14 H) 1.56-1.74 (m, 2 H) 2.19-2.42 (m, 3 H) 2.47-2.68 (m, 1 H) 2.95-3.13 (m, 1 H) 3.75-3.85 (m, 2 H) 4.17 (t, J = 6.5 Hz, 2 H) 7.21-7.34 (m, 1 H) 7.42-7.56 (m, 2 H) | ESI (Pos) 556 (M + Na)⁺ | 2 |
| 24 | F | 3,4-dichlorobenzyl-S- | Benzyl | H | (300 MHz, CD$_3$OD) 2.19-2.43 (m, 3 H) 2.47-2.63 (m, 1 H) 2.96-3.12 (m, 1 H) 3.75 (d, J = 13.2 Hz, 1 H) 3.81 (d, J = 13.2 Hz, 1 H) 5.22 (s, 2 H) 7.23-7.54 (m, 8 H) | ESI (Nega) 482 (M − H)⁻ | 2 |

*¹hydrochloride salt
*²CH$_3$CH$_2$COOCH$_2$CH$_3$

Example 6

Synthesis of (1R,2R,3R,5R,6R)-2-amino-3-(3,4-dichlorobenzyloxy)-6-fluorobicyclo[3.1.0]hexane-2,6-carboxylate 6-diethylcarbamoylmethyl ester

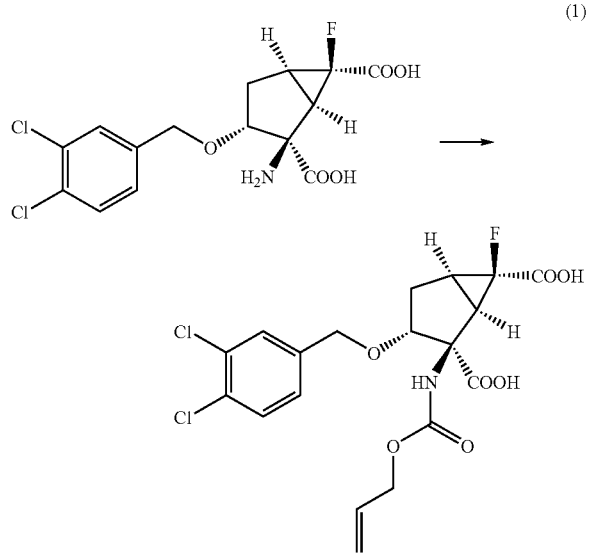

6.7 mL of saturated sodium hydrogen carbonate was added to 740 mg of (1R,2R,3R,5R,6R)-2-amino-3-(3,4-dichlorobenzyl)-6-fluorobicyclo[3.1.0]hexane-2,6-di carboxylic acid suspended in 2.6 mL of dioxane, and the mixture was stirred for 10 minutes at room temperature. 0.41 mL of allyl chloroformate was added dropwise thereto, and the solution was stirred for 12 hours at room temperature. After 2.6 mL of water was added to the reaction solution, the aqueous layer was washed with ethyl acetate, acidified with 1N hydrochloric acid in an ice bath, and then extracted twice with ethyl acetate. The ethyl acetate layers were combined, dried over anhydrous sodium sulfate, and then concentrated under reduced pressure, thereby yielding 930 mg of (1R,2R,3R,5R,6R)-2-allyloxycarbonylamino-3-(3,4-dichlorobenzyloxy)-6-fluorobicyclo[3.1.0]hexane-2,6-dicarboxylic acid.

¹H-NMR (300 MHz, CD$_3$OD, TMS); 2.15-2.53 (m, 3H) 2.89-3.01 (m, 1H) 4.06-4.19 (m, 1H) 4.46 (d, J=11.7 Hz, 1H) 4.55 (d, J=4.8 Hz, 1H) 4.71 (d, J=11.7 Hz, 1H) 5.16-5.20 (m, 1H) 5.29-5.36 (m, 1H) 5.89-5.99 (m, 1H) 7.22 (dd, J=8.2, 2.0 Hz, 1H) 7.44 (d, J=8.2 Hz, 1H) 7.48 (d, J=2.0 Hz, 1H).

MS (ESI)(Nega) m/z; 460 (M−H)⁻

(2)

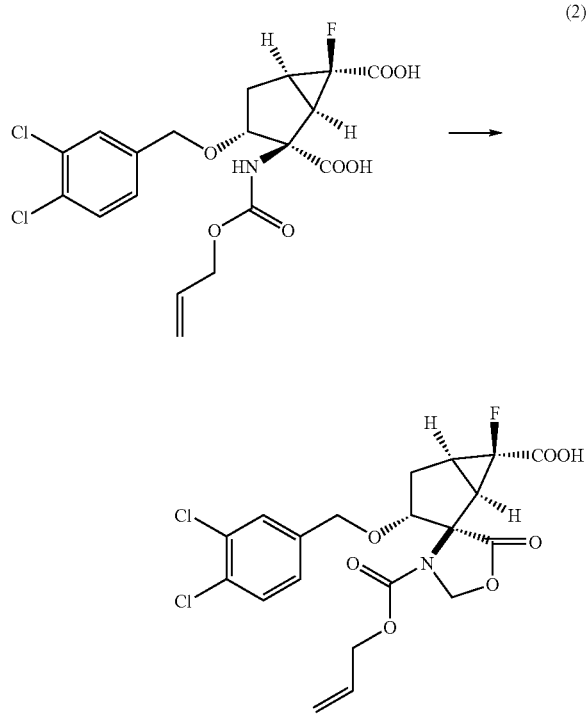

A mixture of 380 mg of (1R,2R,3R,5R,6R)-2-allyloxycarbonylamino-3-(3,4-dichlorobenzyloxy)-6-fluorobicyclo[3.1.0]hexane-2,6-dicarboxylic acid, 109 mg of paraformaldehyde and 8 mg of paratoluenesulfonic acid monohydrate dissolved in 10 mL of benzene was heated to reflux for 3.5 hours using a Dean-Stark distillation trap. After standing to cool, the mixture was diluted with ethyl acetate, and the ethyl acetate solution was washed with water. The ethyl acetate layer was dried over anhydrous sodium sulfate, and then concentrated under reduced pressure, thereby yielding 370 mg of (1'R,2'R,3'R,5'R,6'R)-3'-(3,4-dichlorobenzyloxy)-6'-fluoro-3-allyloxycarbonyl-5-oxo-oxazolidinone-4-spiro-2'-bicyclo[3.1.0]hexane-6'-carboxylate.

$^1$H-NMR (300 MHz, CDCl$_3$, TMS); 2.07-2.54 (m, 4H) 4.17-4.24 (m, 1H) 4.39 (d, J=12.3 Hz, 1H) 4.52 (d, J=12.3 Hz, 1H) 4.63 (d, J=6.2 Hz, 2H) 5.23 (d, J=4.4 Hz, 1H) 5.28-5.54 (m, 2H) 5.53 (d, J=4.5 Hz, 1H) 5.85-5.98 (m, 1H) 7.07 (dd, J=8.2, 1.9 Hz, 1H) 7.32 (d, J=1.9 Hz, 1H) 7.41 (d, J=8.2 Hz, 1H).

MS (ESI)(Nega) m/z; 472 (M–H)$^-$ (3)

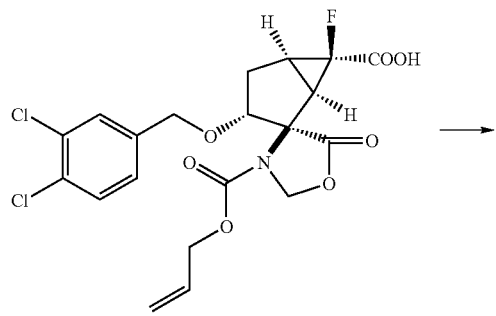

-continued

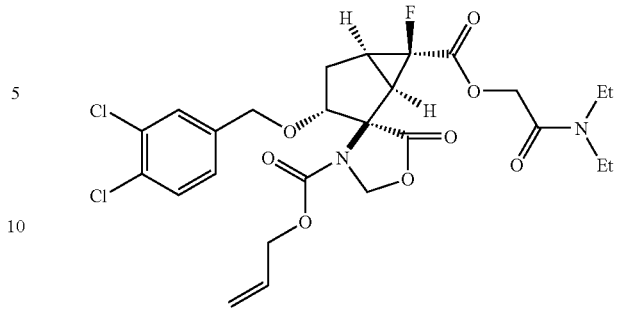

37 mg of potassium carbonate and 37 μL of N,N-diethylchloroacetoamide were added to 58 mg of (1'R,2'R,3'R,5'R,6'R)-3'-(3,4-dichlorobenzyloxy)-6'-fluoro-3-allyloxycarbonyl-5-oxo-oxazolidinone-4-spiro-2'-bicyclo[3.1.0]hexane-6'-carboxylate dissolved in 2 mL of N,N-dimethylformamide, and the mixture was stirred for 15 hours at room temperature. After the mixture was diluted with ethyl acetate, the ethyl acetate layer was washed with water and with a saturated aqueous solution of sodium chloride, and then dried over anhydrous sodium sulfate. After the drying agent was filtered off, the filtrate was concentrated under reduced pressure, and the residue was purified by column chromatography (silica gel: silica gel 60N (Kanto Chemical Co., Inc), eluent: hexane-ethyl acetate=1:2), thereby yielding 60 mg of (1'R,2'R,3'R,5'R,6'R)-3'-(3,4-dichlorobenzyloxy)-6'-fluoro-3-allyloxycarbonyl-5-oxo-oxazolidinone-4-spiro-2'-bicyclo[3.1.0]hexane-6'-carboxylate 6-(N,N-diethylaminocarbonylmethyl) ester.

$^1$H-NMR (300 MHz, CDCl$_3$, TMS); 1.12 (t, J=7.23 Hz, 3H) 1.23 (t, J=7.2 Hz, 3H) 2.21-2.60 (m, 4H) 3.23 (q, J=7.2 Hz, 2H) 3.38 (q, J=7.2 Hz, 2H) 4.19-4.27 (m, 1H) 4.38 (d, J=12.3 Hz, 1H) 4.52 (d, J=12.3 Hz, 1H) 4.63-4.65 (m, 2H) 4.74 (d, J=14.1 Hz, 1H) 4.85 (m, J=14.1 Hz, 1H) 5.23 (d, J=4.3 Hz, 1H) 5.24-5.33 (m, 2H) 5.51 (d, J=4.3 Hz, 1H) 5.87-6.00 (m, 1H) 7.07 (dd, J=8.2, 2.0 Hz, 1H) 7.31 (d, J=2.0 Hz, 1H) 7.40 (d, J=8.2 Hz, 1H).

MS (ESI)(Pos) m/z; 609 (M+Na)$^+$ (4)

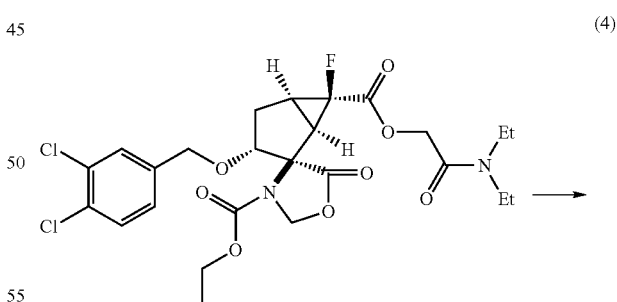

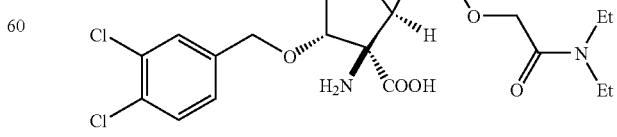

46 mg of 1,3-dimethylbarbituric acid and 4 mg of tetrakis(triphenylphosphine) palladium were added to 58 mg of (1'R, 2'R,3'R,5'R,6'R)-3'-(3,4-dichlorobenzyloxy)-6'-fluoro-3-allyloxycarbonyl-5-oxo-oxazolidinone-4-spiro-2'-bicyclo[3.1.0]hexane-6'-carboxylate-6-(N,N-diethylaminocarbonylmethyl)ester dissolved in chloroform under a nitrogen atmosphere, and the mixture was stirred for 1.5 hours at 40° C. After the reaction solution was concentrated under reduced pressure, ethyl acetate was added to the residue, and the mixture was stirred for 1 hour at room temperature. After the precipitated solids were filtered off, the filtrate was concentrated under reduced pressure and the obtained residue was purified by reverse phase chromatography (Wako gel 50C18 (made by Wako Pure Chemical Industries Ltd.) eluent: water to a 50% aqueous solution of acetonitrile), and then the obtained solids were further washed with ethyl acetate, thereby yielding 5 mg of (1R,2R,3R,5R,6R)-2-amino-3-(3,4-dichlorobenzyloxy)-6-fluorobicyclo[3.1.0]hexane-2,6-carboxylic acid-6-(N,N-diethylaminocarbonylmethyl)ester.

Example 7

Synthesis of (1R,2R,3R,5R,6R)-2-amino-3-(3,4-dichlorobenzyloxy)-6-fluorobicyclo[3.1.0]hexane-2,6-dicarboxylic acid 6-(4-fluorobenzyl)ester

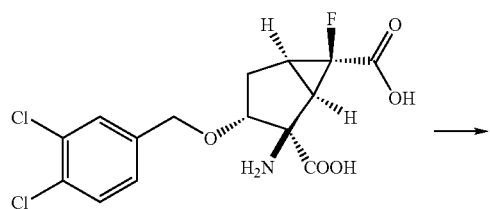

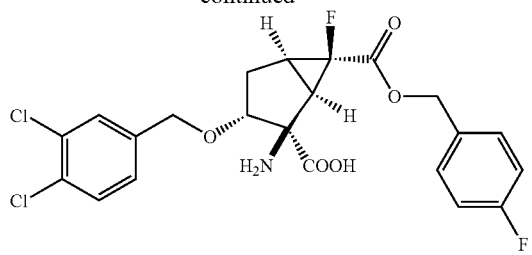

23 µL of thionyl chloride was added to 30 mg of (1R,2R,3R,5R,6R)-2-amino-3-(3,4-dichlorobenzyloxy)-6-fluorobicyclo[3.1.0]hexane-2,6-dicarboxylic acid suspended in 0.3 mL of 4-fluorobenzyl alcohol at room temperature, and the mixture was stirred for 3 days at 60° C. After standing to cool, the reaction solution was purified by reverse phase chromatography (Wako gel 50C18 (made by Wako Pure Chemical Industries Ltd.) eluent: water, a 70% aqueous solution of acetonitrile), thereby yielding 5 mg of (1R,2R,3R,5R,6R)-2-amino-3-(3,4-dichlorobenzyloxy)-6-fluorobicyclo[3.1.0]hexane-2,6-dicarboxylic acid 6-(4-fluorobenzyl)ester.

The structure and physical data of the compounds described in Examples 6 and 7, as well as those of compounds yielded by means of the same methods are shown in table 2 below.

TABLE 2

The structure and physical data of the compounds described in Examples 6 and 7

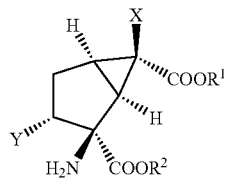

| No. | X | Y | R¹ | R² | NMR (300 MHz, TMS, CD3OD) | MS ESI (Nega) | Example |
|---|---|---|---|---|---|---|---|
| 25 | F | Cl-(3,4-dichlorobenzyl)-O | H₂C-(3-methoxybenzyl) | H | 2.31-2.63 (m, 4 H) 3.79 (s, 3 H) 3.96-4.06 (m, 1 H) 4.46 (d, J = 11.7 Hz, 1 H) 4.59 (d, J = 11.7 Hz, 1 H) 5.20 (s, 2 H) 6.85-6.97 (m, 3 H) 7.22-7.31 (m, 2 H) 7.41-7.56 (m, 2 H) | 496 (M − H)⁻ | 7 |

TABLE 2-continued

The structure and physical data of the compounds described in Examples 6 and 7

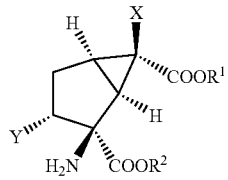

| No. | X | Y | R¹ | R² | NMR (300 MHz, TMS, CD3OD) | MS ESI (Nega) | Example |
|---|---|---|---|---|---|---|---|
| 26 | F | 3,4-Cl₂-C₆H₃-CH₂-O- | 4-MeO-C₆H₄-CH₂- | H | 2.30-2.63 (m, 4 H) 3.79 (s, 3 H) 3.95-4.03 (m, 1 H) 4.46 (d, J = 12.4 Hz, 1 H) 4.58 (d, J = 12.4 Hz, 1 H) 5.16 (s, 2 H) 6.90 (d, J = 8.9 Hz, 2 H) 7.29 (m, 3 H) 7.44 (d, J = 8.2 Hz, 1 H) 7.53 (d, J = 1.9 Hz, 1 H) | 496 (M − H)⁻ | 6 |
| 27 | F | 3,4-Cl₂-C₆H₃-CH₂-O- | 4-F-C₆H₄-CH₂- | H | 2.30-2.65 (m, 4 H) 3.95-4.05 (m, 1 H) 4.46 (d, J = 12.3 Hz, 1 H) 4.58 (d, J = 12.3 Hz, 1 H) 5.21 (s, 1 H) 7.06-7.14 (m, 2 H) 7.25-7.30 (m, 1 H) 7.38-7.46 (m, 3 H) 7.51-7.55 (m, 1 H) | 484 (M − H)⁻ | 7 |
| 28 | F | 3,4-Cl₂-C₆H₃-CH₂-O- | EtOOC-CH₂- | H | 1.27 (t, J = 7.1 Hz, 3 H) 2.42-2.68 (m, 4 H) 3.98-4.08 (m, 1 H) 4.22 (q, J = 7.1 Hz, 2 H) 4.48 (d, J = 12.0 Hz, 1 H) 4.60 (d, J = 12.0 Hz, 1 H) 4.76 (s, 2 H) 7.29 (dd, J = 8.2, 2.0 Hz, 1 H) 7.45 (d, J = 8.2 Hz, 1 H) 7.55 (d, J = 2.0 Hz, 1 H) | 462 (M − H)⁻ | 6 |
| 29 | F | 3,4-Cl₂-C₆H₃-CH₂-O- | Et₂N-CO-CH₂- | H | 1.13 (t, J = 7.1 Hz, 3 H) 1.23 (t, J = 7.1 Hz, 3 H) 2.42-2.68 (m, 4 H) 3.32-3.43 (m, 4 H) 3.98-4.09 (m, 1 H) 4.48 (d, J = 12.3 Hz, 1 H) 4.60 (d, J = 12.3 Hz, 1 H) 4.94 (s, 2 H) 7.26-7.32 (m, 1 H) 7.45 (d, J = 8.2 Hz, 1 H) 7.53-7.56 (m, 1 H) | 489 (M − H)⁻ | 6 |
| 30 | F | 3,4-Cl₂-C₆H₃-CH₂-O- | morpholino-CH₂-CH₂- | H | (300 MHz, D2O, TMSP) 2.47-1.58 (m, 4 H) 3.33-3.41 (m, 4 H) 3.52-3.58 (m, 2 H) 3.92-4.13 (m, 5 H) 4.48-4.64 (m, 4 H) 7.29 (dd, J = 8.2, 1.9 Hz, 1 H) 7.53-7.56 (m, 2 H) | 489 (M − H)⁻ | 6 |

TABLE 2-continued

The structure and physical data of the compounds described in Examples 6 and 7

| No. | X | Y | R¹ | R² | NMR (300 MHz, TMS, CD3OD) | MS ESI (Nega) | Example |
|---|---|---|---|---|---|---|---|
| 31 | F | 3,4-dichlorobenzyloxy | Farnesyl | H | 1.60 (s, 6 H) 1.66 (s, 3 H) 1.73 (s, 3 H) 1.92-2.18 (m, 8 H) 2.22-2.61 (m, 4 H) 3.83-3.96 (m, 1 H) 4.46 (d, J = 12.1 Hz, 1 H) 4.63 (d, J = 12.1 Hz, 1 H) 4.70 (d, J = 7.2 Hz, 2 H) 5.02-5.16 (m, 2 H) 5.30-5.39 (m, 1 H) 7.24-7.32 (m, 1 H) 7.44 (d, J = 8.2 Hz, 1 H) 7.51-7.57 (m, 1 H) | 580 (M − H)⁻ | 6 |
| 32 | F | 3,4-dichlorobenzyloxy | MeCH(O-)OC(O)OEt | H | 1.28 (t, J = 7.1 Hz, 1.5 H) 1.29 (t, J = 7.1 Hz, 1.5 H) 1.51 (d, J = 5.4 Hz, 1.5 H) 1.52 (d, J = 5.4 Hz, 1.5 H) 2.49 (m, 4 H) 4.01 (m, 1 H) 4.20 (q, J = 7.1 Hz, 2 H) 4.47 (d, J = 11.8 Hz, 1 H) 4.59 (m, J = 11.8 Hz, 1 H) 6.76 (q, J = 5.4 Hz, 1 H) 7.28 (dd, J = 8.2, 2.0 Hz, 1 H) 7.45 (d, J = 8.2 Hz, 1 H) 7.54 (d, J = 2.0 Hz, 1 H) | 492 (M − H)⁻ | 6 |
| 33 | F | 3,4-dichlorobenzyloxy | MeCH(O-)OC(O)O-iPr | H | 1.27 (d, J = 6.2 Hz, 6 H) 1.51 (d, J = 6.2 Hz, 3 H) 2.31-2.66 (m, 4 H) 3.98-4.05 (m, 1 H) 4.47 (d, J = 11.8 Hz, 1 H) 4.59 (d, J = 11.8 Hz, 2 H) 6.76 (q, J = 6.2 Hz, 1 H) 7.28 (dd, J = 8.2, 2.0 Hz, 1 H) 7.45 (d, J = 8.2 Hz, 1 H) 7.54 (d, J = 2.0 Hz, 1 H) | 506 (M − H)⁻ | 6 |
| 34 | F | 3,4-dichlorobenzyloxy | MeCH(O-)OC(O)O-cyclohexyl | H | 1.21-1.61 (m, 8 H) 1.68-1.96 (m, 4 H) 2.30-2.66 (m, 4 H) 3.98-4.07 (m, 1 H) 4.47 (d, J = 12.0 Hz, 1 H) 4.57-4.67 (m, 2 H) 6.76 (q, J = 5.3 Hz, 1 H) 7.28 (dd, J = 8.3, 2.0 Hz, 1 H) 7.45 (d, J = 8.3 Hz, 1 H) 7.54 (d, J = 2.0 Hz, 1 H) | 546 (M − H)⁻ | 6 |

TABLE 2-continued

The structure and physical data of the compounds described in Examples 6 and 7

| No. | X | Y | R¹ | R² | NMR (300 MHz, TMS, CD3OD) | MS ESI (Nega) | Example |
|---|---|---|---|---|---|---|---|
| 35 | F | Cl | 3,4-dichlorobenzyl | 4-methyl-2-oxo-1,3-dioxol-5-ylmethyl | H | 2.18 (s, 3 H) 2.32-2.66 (m, 4 H) 3.95-4.08 (m, 1 H) 4.47 (d, J = 11.8 Hz, 1 H) 4.59 (d, J = 11.8 Hz, 1 H) 5.06 (s, 2 H) 7.25-7.32 (m, 1 H) 7.45 (d, J = 8.2 Hz, 1 H) 7.51-7.57 (m, 1 H) | 488 (M − H)⁻ | 6 |
| 36 | F | Cl | 3,4-dichlorobenzyl | (4-methoxyphenoxycarbonyl)oxymethyl | H | 2.34-2.67 (m, 4 H) 3.87 (s, 3 H) 3.95-4.06 (m, 1 H) 4.46 (d, J = 12.0 Hz, 1 H) 4.58 (d, J = 12.0 Hz, 1 H) 6.05 (s, 2 H) 7.02 (d, J = 9.0 Hz, 2 H) 7.24-7.30 (m, 1 H) 7.44 (d, J = 8.2 Hz, 1 H) 7.50-7.56 (m, 1 H) 8.00 (d, J = 9.0 Hz, 3 H) | 540 (M − H)⁻ | 6 |
| 37 | F | Cl | 3,4-dichlorobenzyl | (2-ethoxynaphthalen-1-yloxycarbonyl)oxymethyl | H | 1.41 (t, J = 7.0 Hz, 3 H) 2.44-2.69 (m, 4 H) 3.99-4.10 (m, 4 H) 4.26 (q, J = 7.0 Hz, 2 H) 4.48 (d, J = 12.0 Hz, 1 H) 4.60 (d, J = 12.0 Hz, 1 H) 6.15 (s, 2 H) 7.25-7.56 (m, 6 H) 7.73 (d, J = 8.1 Hz, 1 H) 7.85 (d, J = 8.1 Hz, 1 H) 8.00 (d, J = 9.8 Hz, 1 H) | 604 (M − H)⁻ | 6 |
| 38 | F | Cl | 3,4-dichlorobenzyl | butanoyloxymethyl | H | 0.95 (t, J = 7.4 Hz, 3 H) 1.64 (sextet, J = 7.4 Hz, 2 H) 2.31-2.97 (m, 6 H) 3.97-4.06 (m, 1 H) 4.47 (d, J = 12.1 Hz, 1 H) 4.59 (d, J = 12.1 Hz, 2 H) 5.83 (s, 2 H) 7.28 (dd, J = 8.2, 2.0 Hz, 1 H) 7.45 (d, J = 8.2 Hz, 1 H) 7.54 (d, J = 2.0 Hz, 1 H) | 476 (M − H)⁻ | 6 |
| 39 | F | Cl | 3,4-dichlorobenzyl | pivaloyloxymethyl | H | 1.20 (s, 9 H) 2.34-2.66 (m, 4 H) 3.96-4.04 (m, 1 H) 4.47 (d, J = 11.8 Hz, 1 H) 459 (d, J = 11.8 Hz, 1 H) 5.83 (s, 2 H) 7.28 (dd, J = 8.2, 2.0 Hz, 1 H) 7.45 (d, J = 8.2 Hz, 1 H) 7.52 (d, J = 2.0 Hz, 1 H) | 490 (M − H)⁻ | 6 |

TABLE 2-continued
The structure and physical data of the compounds described in Examples 6 and 7
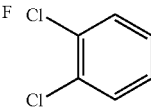
| No. | X | Y | R$^1$ | R$^2$ | NMR (300 MHz, TMS, CD3OD) | MS ESI (Nega) | Example |
|---|---|---|---|---|---|---|---|
| 40 | F | Cl | 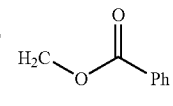 | 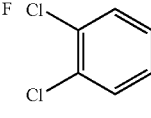 | H | 2.35-2.66 (m, 4 H) 3.97-4.05 (m, 1 H) 4.46 (d, J = 12.1 Hz, 1 H) 4.58 (d, J = 12.1 Hz, 1 H) 6.08 (s, 2 H) 7.27 (dd, J = 8.3, 1.9 Hz, 1 H) 7.44 (d, J = 8.3 Hz, 1 H) 7.48-7.56 (m, 3 H) 7.61-7.69 (m, 2 H) 8.05 (d, J = 7.2 Hz, 2 H) | 510 (M − H)$^-$ | 6 |
| 41 | F | Cl | 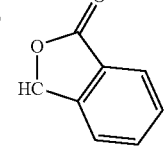 | H | 2.35-2.67 (m, 4 H) 3.96-4.06 (m, 1 H) 4.46 (d, J = 12.0 Hz, 1 H) 4.59 (d, J = 12.0 Hz, 1 H) 7.27 (dd, J = 8.2, 1.9 Hz, 1 H) 7.44 (d, J = 8.2 Hz, 1 H) 7.52-7.54 (m, 2 H) 7.69-7.95 (m, 4 H) | 508 (M − H)$^-$ | 6 |
| 42 | H | Cl | 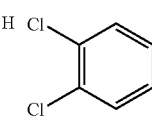 | 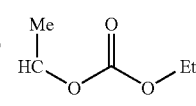 | H | 1.22-1.32 (m, 3 H) 1.42-1.50 (m, 3 H) 1.87-1.94 (m, 1 H) 2.11-2.27 (m, 2 H) 2.32-2.41 (m, 2 H) 3.61-3.70 (m, 1 H) 4.11-4.23 (m, 2 H) 4.44 (d, J = 11.97 Hz, 1 H) 4.51 (d, J = 11.97 Hz, 1 H) 6.63-6.72 (m, 1 H) 7.22-7.30 (m, 1 H) 7.45 (d, J = 8.24 Hz, 1 H) 7.53 (s, 1 H) | 474 (M − H)$^-$ | 6 |

TABLE 2-continued

The structure and physical data of the compounds described in Examples 6 and 7

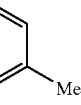

| No. | X | Y | R¹ | R² | NMR (300 MHz, TMS, CD3OD) | MS ESI (Nega) | Example |
|---|---|---|---|---|---|---|---|
| 43 | F |  | 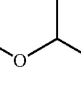 | H | 2.03 (3 H, s), 2.30-2.64 (4 H, m), 3.97-4.07 (1 H, m), 4.46 (1 H, d, J = 11.8 Hz), 4.58 (1 H, d, J = 11.80 Hz), 5.18 (2 H, s) 7.14-7.57 (7 H, m) | 480 (M − H)⁻ | 7 |
| 44 | H |  |  | H | 1.30-1.98 (14 H, m), 2.11-2.27 (2 H, m), 2.31-2.42 (2 H, m), 3.59-3.71 (1 H, m), 4.44 (1 H, d, J = 12.1 Hz), 4.51 (1 H, d, J = 12.1 Hz), 4.54-4.66 (1 H, m), 6.61-6.72 (1 H, m), 7.26 (1 H, dd, J = 8.2, 1.7 Hz), 7.45 (1 H, d, J = 8.2 Hz), 7.53 (1 H, d, J = 1.7 Hz) | 528 (M − H)⁻ | 6 |
| 45 | F |  | Benzyl | H | 2.31-2.62 (4 H, m), 3.94-4.04 (1 H, m), 4.46 (1 H, d, J = 11.7 Hz), 4.59 (1 H, d, J = 11.7 Hz), 5.23 (2 H, s), 7.26-7.39 (9 H, m) | 432 (M − 1)⁻ | 7 |

Example 8

Synthesis of (1R,2R,3R,5R,6R)-2-amino-3-(3,4-dichlorobenzyloxy)-6-fluorobicyclo[3.1.0]hexane-2,6-dicarboxylic acid 6-(3-methyl)butyl ester 1.0 mL of thionyl chloride was added to 1.50 g of (1R,2R,3R,5R,6R)-2-amino-3-(3,4-dichlorobenzyloxy)-6-fluorobicyclo[3.1.0]hexane-2,6-dicarboxylic acid suspended in 20 mL of 3-methylbutanol at ice-cooling, and the mixture was stirred for 3 hours at 70° C. After standing to cool, 3-methylbutanol was distilled under reduced pressure. 15 mL of ethanol and 15 mL of propyleneoxide were added to the residue, and the mixture was heated to redux for 1 hour. After standing to cool, the mixture was diluted with diethyl ether, and the precipitated solids were filtered. The solids were washed with water, diisopropyl ether and hexane, thereby yielding 1.01 g of (1R,2R,3R,5R,6R)-2-amino-3-(3,4-dichlorobenzyloxy)-6-fluorobicyclo[3.1.0]hexane-2,6-dicarboxylic acid 6-(3-methyl)-n-butyl ester.

Example 9

Synthesis of (1R,2R,3R,5R,6R)-2-amino-3-(3,4-dichlorobenzyloxy)-6-fluorobicyclo[3.1.0]hexane-2,6-dicarboxylic acid 6-(6-methyl)heptyl ester 0.4 mL of thionyl chloride was added to 1.00 g of (1R,2R,3R,5R,6R)-2-amino-3-(3,4-dichlorobenzyloxy)-6-fluorobicyclo[3.1.0]hexane-2,6-dicarboxylic acid suspended in 10 mL of 6-methyl-1-heptanol at ice-cooling, and the mixture was stirred for 6 hours at 80° C. After standing to cool, the insoluble matter was filtered off, and the filtrate was concentrated under reduced pressure. The residue was purified by reverse phase column chromatography (Wako gel 50C18 (made by Wako Pure Chemical Industries Ltd.) eluent: water to a 70% aqueous solution of acetonitrile). The obtained solids were recrystallized from ethanol:water, thereby yielding 557 mg of (1R,2R,3R,5R,6R)-2-amino-3-(3,4-dichlorobenzyloxy)-6-fluorobicyclo[3.1.0]hexane-2,6-dicarboxylic acid 6-(6-methyl) heptyl ester.

The structure and physical data of the compounds described in Examples 8 and 9, as well as those of compounds yielded by means of the same methods are shown in table 3 below.

TABLE 3

The structure and physical data of the compounds described in Examples 8 and 9

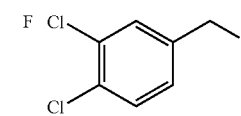

| No. | X | Y | R¹ | R² | NMR (300 MHz, TMS, CD3OD) | MS ESI (Nega) | Example |
|---|---|---|---|---|---|---|---|
| 46 | F | 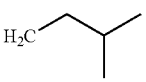 | 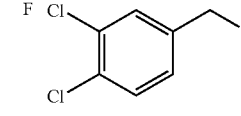 | H | 0.93 (6 H, d, J = 6.5 Hz), 1.52-1.59 (2 H, m), 1.65-1.74 (1 H, m) 2.31-2.64 (4 H, m), 3.97-4.05 (1 H, m), 4.24 (2 H, t. J = 6.7 Hz), 4.47 (1 H, d, J = 12.1 Hz), 4.59 (1 H, d, J = 12.1 Hz), 7.28 (1 H, dd, J = 8.2, 2.0 Hz), 7.45 (1 H, d, J = 8.2 Hz), 7.54 (1 H, d, J = 2.0 Hz) | 446 (M − H)⁻ | 8 |
| 47 | F |  | 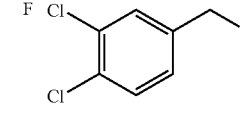 | H | 0.91 (3 H, t, J = 6.7 Hz), 1.26-1.43 (6 H, m), 1.60-1.72 (2 H, m), 2.31-2.67 (4 H, m), 3.97-4.06 (1 H, m), 4.19 (2 H, t, J = 6.6 Hz), 4.47 (1 H, d, J = 12.0 Hz), 4.59 (1 H, d, J = 12.0 Hz), 7.28 (1 H, dd, J = 8.2, 1.7 Hz), 7.45 (1 H, d, J = 8.2 Hz), 7.54 (1 H, d, J = 1.7 Hz) | 460 (M − H)⁻ | 8 |
| 48 | F | 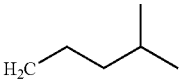 | 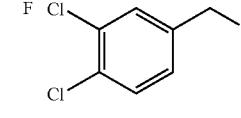 | H | 0.91 (6 H, d, J = 6.7 Hz), 1.19-1.31 (2 H, m), 1.49-1.72 (3 H, m), 2.32-2.66 (4 H, m), 3.98-4.70 (1 H, m), 4.18 (1 H, t, J = 6.6 Hz), 4.48 (1 H, d, J = 11.8 Hz), 4.60 (1 H, d, J = 11.8 Hz), 7.29 (1 H, dd, J = 8.2, 2.1 Hz), 7.46 (1 H, d, J = 8.2 Hz), 7.55 (1 H, d, J = 2.1 Hz) | 460 (M − H)⁻ | 8 |
| 49 | F | 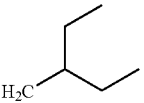 | 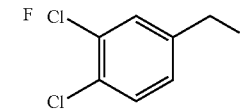 | H | 0.91 (6 H, t, J = 7.5 Hz), 1.33-1.43 (4 H, m), 1.46-1.60 (1 H, m), 2.31-2.65 (4 H, m), 3.98-4.05 (1 H, m), 4.14 (2 H, d, J = 5.1 Hz), 4.47 (1 H, d, J = 12.0 Hz), 4.59 (1 H, d, J = 12.0 Hz), 7.28 (1 H, dd, J = 8.1, 1.9 Hz), 7.45 (1 H, d, J = 8.1 Hz), 7.54 (1 H, d, J = 1.9 Hz) | 460 (M − H)⁻ | 8 |
| 50 | F | 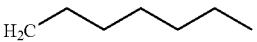 | 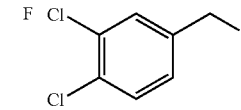 | H | 0.90 (3 H, t, J = 6.5 Hz), 1.26-1.42 (8 H, m), 1.59-1.72 (2 H, m), 2.31-2.40 (2 H, m), 2.48 (1 H, dd, J = 13.3, 7.4 Hz), 2.50-2.66 (1 H, m), 3.98-4.03 (1 H,m), 4.19 (2 H, t, J = 6.5 Hz), 4.47 (1 H, d, J = 12.0 Hz), 4.59 (1 H, d, J = 12.0 Hz), 7.28 (1 H, dd, J = 8.2, 1 H), 7.45 (1 H, d, J = 8.2 Hz), 7.54 (1 H, d, J = 2.0 Hz) | 476 (M + H)⁺ | 8 |
| 51 | F | 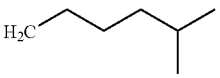 |  | H | 0.90 (6 H, d, J = 6.5 Hz), 1.17-1.71 (7 H, m), 2.32-2.40 (2 H, m), 2.49 (1 H, dd, J = 13.2, 7.3 Hz), 2.55-2.66 (1 H, m), 3.98-4.07 (1 H, m), 4.20 (2 H, t, J = 6.5 Hz), 4.48 (1 H, d, J = 12.0 Hz), 4.60 (1 H, d, J = 12.0 Hz), 7.29 (1 H, dd, J = 8.2, 1.9 Hz), 7.46 (1 H, d, J = 8.2 Hz), 7.55 (1 H, d, J = 1.9 Hz) | 476 (M + H)⁺ | 8 |

TABLE 3-continued

The structure and physical data of the compounds described in Examples 8 and 9

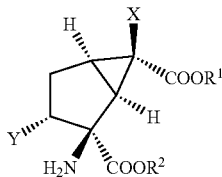

| No. | X | Y | R¹ | R² | NMR (300 MHz, TMS, CD3OD) | MS ESI (Nega) | Example |
|---|---|---|---|---|---|---|---|
| 52 | F | 3,4-diCl-C6H3-CH2-O- | H2C-(CH2)6-CH3 | H | 0.90 (3 H, t, J = 6.6 Hz), 1.25-1.42 (10 H, m), 1.60-1.71 (2 H, m), 2.31-2.40 (2 H, m), 2.48 (1 H, dd, J = 13.4, 7.6 Hz), 2.5-2.7 (1 H, m), 4.05-4.06 (1 H, m), 4.19 (2 H, t, J = 6.6 Hz), 4.47 (1 H, d, J = 12.0 Hz), 4.59 (1 H, d, J = 12.0 Hz), 7.28 (1 H, dd, J = 8.2, 1.9 Hz), 7.45 (1 H, d, J = 8.2 Hz), 1.9 (1 H, d, J = 1.9 Hz) | 490 (M + H)⁺ | 8 |
| 53 | F | 3,4-diCl-C6H3-CH2-O- | H2C-(CH2)3-CH(CH3)2 | H | 0.89 (6 H, d, J = 6.7 Hz), 1.15-1.39 (6 H, m), 1.47-1.71 (3 H, m), 2.33-2.65 (4 H, m), 4.02 (1 H, m), 4.19 (2 H, t, J = 6.5 Hz), 4.48 (1 H, d, J = 12.1 Hz), 4.60 (1 H, d, J = 12.1 Hz), 7.29 (1 H, dd, J = 8.2, 2.0 Hz), 7.46 (1 H, d, J = 8.2 Hz), 7.54 (1 H, d, J = 2.0 Hz) | 488 (M − H)⁻ | 9 |
| 54 | F | 3,4-diCl-C6H3-CH2-O- | H2C-CH(CH3)-(CH2)3-CH(CH3)2 | H | 0.86-0.95 (9 H, m), 1.06-1.76 (10 H, m), 2.31-2.66 (4 H, m), 3.98-4.05 (1 H, m), 4.24 (2 H, t, J = 6.8 Hz), 4.47 (1 H, d, J = 11.8 Hz), 4.59 (1 H, m), 7.28 (1 H, dd, J = 8.2, 1.8 Hz), 7.45 (1 H, d, J = 8.2 Hz), 7.54 (1 H, d, J = 1.8 Hz) | 516 (M − H)⁻ | 9 |
| 55 | F | 3,4-diCl-C6H3-CH2-NH- | i-Bu | H | 0.94 (6 H, d, J = 6.7 Hz), 1.88-2.01 (1 H, m), 2.28-2.55 (4 H, m), 3.15-3.23 (1 H, m), 3.74 (1 H, d, J = 15.4 Hz), 3.79 (1 H, d, J = 15.4 Hz), 3.93-4.02 (2 H, m), 7.27 (1 H, dd, J = 8.2, 2.0 Hz), 7.45 (1 H, d, J = 8.2 Hz), 7.54 (1 H, d, J = 2.0 Hz) | 431 (M − H)⁻ | 8 |
| 56 | F | Ph2CH-O- | Et | H | 1.25 (3 H, t, J = 7.2 Hz), 2.04-2.34 (3 H, m), 2.48-2.60 (1 H, m), 3.89-4.03 (1 H, m), 4.21 (2 H, q, J = 7.2 Hz), 5.51 (1 H, s), 7.15-7.39 (10 H, m) | 412 (M − 1)⁻ | 8 |
| 57 | F | 2-Naphthyl-CH2-O- | i-Pr | H | 1.26 (6 H, d, J = 6.2 Hz), 2.31-2.67 (4 H, m), 4.04-4.11 (1 H, m), 4.66 (1 H, d, J = 11.8 Hz), 4.79 (1 H, d, J = 11.8 Hz), 5.01-5.13 (1 H, m), 7.40-7.51 (3 H, m), 7.78-7.87 (4 H, m) | 400 (M − 1)⁻ | 8 |

Example 10

Synthesis of (1R,2R,3R,5R,6R)-2-amino-3-(3,4-dichlorobenzyloxy)-6-fluorobicyclo[3.1.0]hexane-2,6-dicarboxylic acid 2-butyl ester 6-ethyl ester and (1R,2R,3R,5R,6R)-2-amino-3-(3,4-dichlorobenzyloxy)-6-fluorobicyclo[3.1.0]hexane-2,6-dicarboxylic acid 2-butyl ester (1) By means of the same method as Example 1, 2.96 g of (1R,2R,3R,5R,6R)-2-amino-3-(3,4-dichlorobenzyloxy)-6-fluorobicyclo[3.1.0]hexane-2,6-dicarboxylic acid 6-ethyl ester hydrochloride was yielded from 4.00 g of (1R,2R,3R,5R,6R)-2-amino-3-(3,4-dichlorobenzyloxy)-6-fluorobicyclo[3.1.0]hexane-2,6-dicarboxylic acid.

(2) 400 mg of (1R,2R,3R,5R,6R)-2-amino-3-(3,4-dichlorobenzyloxy)-6-fluorobicyclo[3.1.0]hexane-2,6-dicarboxylic acid 6-ethyl ester hydrochloride was added to a mixture of 5 mL of ethanol and 5 mL of propyleneoxide, and the mixture was heated to redux for 2.5 hours. After standing to cool, the precipitated solids were filtered, and the solids were washed with diethyl ether and then recrystallized from water:ethanol, thereby yielding 230 g of (1R,2R,3R,5R,6R)-2-amino-3-(3,4-dichlorobenzyloxy)-6-fluorobicyclo[3.1.0]hexane-2,6-dicarboxylic acid 6-ethyl ester.

(3) 2 mL of saturated sodium hydrogen carbonate was added to 200 mg of (1R,2R,3R,5R,6R)-2-amino-3-(3,4-dichlorobenzyloxy)-6-fluorobicyclo[3.1.0]hexane-2,6-dicarboxylic acid 6-ethyl ester suspended in 1 mL of dioxane, and the mixture was stirred for 10 minutes at room temperature. 0.18 mL of allyl chloroformate was added thereto, and the solution was stirred for 8 hours at room temperature. After the reaction solution was acidified with 1 mL of 1N hydrochloric acid, 10 mL of water was added thereto, and the mixture was extracted twice with ethyl acetate. The ethyl acetate layers were combined, dried over anhydrous sodium sulfate and concentrated under reduced pressure, and the obtained residue was dissolved in 20 mL of N,N-dimethylformamide. 141 mg of 1-iodobutane and 106 mg of potassium carbonate were added to the solution, and the mixture was stirred for 16 hours at room temperature. Water was added thereto, and the reaction solution was extracted twice with ethyl acetate. After the ethyl acetate layers were combined and dried over anhydrous sodium sulfate, the solvent was distilled under reduced pressure and purified by column chromatography (silica gel: Kanto Chemical silica gel 60 (spherical), eluent: hexane-ethyl acetate=5:1), thereby yielding 159 mg of (1R,2R,3R,5R,6R)-2-allyloxycarbonylamino-3-(3,4-dichlorobenzyloxy)-6-fluorobicyclo[3.1.0]hexane-2,6-dicarboxylic acid 2-butyl ester 6-ethyl ester.

$^1$H-NMR (300 MHz, CDCl$_3$, TMS) 0.89 (3H, t, J=7.4 Hz), 1.24-1.43 (5H, m), 1.56-1.66 (2H, m), 2.22-2.51 (3H, m), 2.93-3.00 (1H, m), 3.81-3.89 (1H, m), 4.08-4.65 (8H, m), 5.16-5.37 (3H, m), 5.84-5.98 (1H, m), 7.09 (1H, dd, J=8.2, 2.0 Hz), 7.37 (1H, d, J=2.0 Hz), 7.40 (1H, d, J=8.2 Hz).

(4) 81 mg of 1,3-dimethylbarbituric acid and 12 mg of tetrakis(triphenylphosphine) palladium were added to 190 mg of (1R,2R,3R,5R,6R)-2-allyloxycarbonylamino-3-(3,4-dichlorobenzyloxy)-6-fluorobicyclo[3.1.0]hexane-2,6-dicarboxylic acid 2-butyl ester 6-ethyl ester dissolved in chloroform under a nitrogen atmosphere, and the mixture was stirred for 1 hour at 50° C. The reaction solution was concentrated under reduced pressure, and the obtained residue was purified by column chromatography (silica gel: Kanto Chemical silica gel 60 (spherical), eluent: hexane-ethyl acetate=5:1), thereby yielding 180 mg of (1R,2R,3R,5R,6R)-2-amino-3-(3,4-dichlorobenzyloxy)-6-fluorobicyclo[3.1.0]hexane-2,6-dicarboxylic acid 2-butyl ester 6-ethyl ester.

(5) 15 mg of lithium hydroxide monohydrate was added to 131 mg of (1R,2R,3R,5R,6R)-2-amino-3-(3,4-dichlorobenzyloxy)-6-fluorobicyclo[3.1.0]hexane-2,6-dicarboxylic acid 2-butyl ester 6-ethyl ester dissolved in 2 mL of tetrahydrofuran and 1 mL of water, and the mixture was stirred for 1.5 hours at room temperature. After 2 mL of 1N hydrochloric acid was added thereto, the reaction solution was concentrated under reduced pressure, and the obtained residue was purified by reverse phase chromatography (Wako gel 50C18 (made by Wako Pure Chemical Industries Ltd.) eluent: water to a 40% acetonitrile solution), thereby yielding 37 mg of (1R,2R,3R,5R,6R)-2-amino-3-(3,4-dichlorobenzyloxy)-6-fluorobicyclo[3.1.0]hexane-2,6-dicarboxylic acid 2-butyl ester.

The structure and physical data of the compound described in Example 10, as well as those of compounds yielded by means of the same method are shown in table 4 below.

TABLE 4

The structure and physical data of the compound described in Example 10

| No. | X | Y | R$^1$ | R$^2$ | NMR (300 MHz, TMS, CD3OD) | MS ESI (Nega) | Example |
|---|---|---|---|---|---|---|---|
| 58 | F | 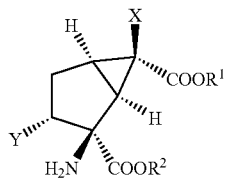 | H | Bu | 0.88 (3 H, t, J = 7.4 Hz), 1.37-1.47 (2 H, m), 1.64-1.71 (2 H, m), 2.22-2.62 (4 H, m), 4.06-4.15 (1 H, m), 4.20-4.41 (2 H, m), 4.53 (2 H, s), 7.21-7.25 (1 H, m), 7.48-7.51 (2 H, m) | 432 (M − 1)$^−$ | 10 |

TABLE 4-continued

The structure and physical data of the compound described in Example 10

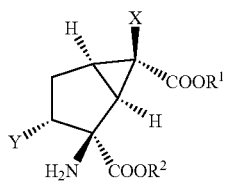

| No. | X | Y | R¹ | R² | NMR (300 MHz, TMS, CD3OD) | MS ESI (Nega) | Example |
|---|---|---|---|---|---|---|---|
| 59 | F | Cl-⟨⟩-CH₂O (3,4-dichlorobenzyloxy) | Et | Bu | (300 MHz, TMS, CDCl₃) 0.90 (3 H, t, J = 7.4 Hz), 1.24-1.45 (5 H, m), 1.60-1.69 (2 H, m), 2.13-2.27 (2 H, m), 2.38-2.49 (2 H, m), 3.74-3.86 (1 H, m), 4.07-4.29 (4 H, m), 4.46 (1 H, d, J = 12.1 Hz), 4.63 (1 H, d, J = 12.1 Hz) 7.09 (1 H, d, J = 8.24 Hz), 7.67 (1 H, s), 7.38 (1 H, d, J = 8.39 Hz) | 484 (M + Na)⁺ | 10 |

Test Example 1

Measurement of the Amount of Exposure In Vivo from the Plasma Concentration in Rat The amount of exposure in vivo was measured, for example, according to the following methods. Compounds 1, 4 and 10 of the present invention and the parent compounds of compounds 1, 4 and 10 of the present invention where in formula [IV], X represents a fluorine atom and Y represents a 3,4-dichlorobenzyloxy group, were orally administered to rat, and then the plasma concentration of the parent compound of the present invention was measured, compared and investigated as shown below. Also, by means of the same method, compound 44 of the present invention and the parent compound of compound 44 were orally administered to rat, and then the plasma concentration of the parent compound of compound 44 of the present invention was measured, compared and examined.

7-week-old rat (240-280 g, male, strain CD(SD)IGS) obtained from Charles River Japan, Inc. habituated for more than 2 days was used as the test subject. The compound of the present invention was dissolved in 0.03N hydrochloric acid containing 10% HP-β-CD, adjusted to a concentration of 2 mg/mL, and then 10 mg/kg of the mixture was orally administered to rat. 1 hour and 2 hours later, blood was collected from the caudal vein with a blood collecting tube (with EDTA) and immediately centrifuged (10000×g, 4° C., 10 minutes), thereby extracting the plasma for the plasma sample. The plasma sample was frozen and stored at −80° C. and below. While still being cooled on ice, the plasma sample was melted, methanol solution was added thereto as an internal standard substance, and after the sample was deproteinized and then centrifuged (10000×g, 4° C., 10 minutes), the concentration of the parent compound of the compound of the present invention in the supernatant was measured by LC/MS/MS.

As shown in the table below, the administration of the compound of the present invention resulted in a significantly higher plasma concentration of the parent compound of the compound of the present invention, and the amount of exposure in vivo was increased.

Comparison of the plasma concentration of the compound of the present invention and of the parent compound of the compound of the present invention

| Compound (10 mg/kg p.o.) | The plasma concentration of the parent compound of the compound of the present invention (ng/mL) | |
|---|---|---|
| | 1 hour later | 2 hours later |
| Compound A*¹ | 123 | 178 |
| The compound of the present invention 1*² | 11332 | 8162 |
| The compound of the present invention 4*³ | 6863 | 7057 |
| The compound of the present invention 10*⁴ | 5956 | 5754 |
| Compound B*⁵ | 73 | 125 |
| The compound of the present invention 44*⁶ | 235 | 610 |

*¹Compound A (the parent compound of compound 1, 4 and 10 of the present invention): (1R,2R,3R,5R,6R)-2-amino-3-(3,4-dichlorobenzyloxy)-6-fluorobicyclo[3.1.0]hexane-2,6-dicarboxylic acid
*²Compound 1 of the present invention: (1R,2R,3R,5R,6R)-2-amino-3-(3,4-dichlorobenzyloxy)-6-fluorobicyclo[3.1.0]hexane-2,6-dicarboxylic acid 6-methyl ester
*³Compound 4 of the present invention: (1R,2R,3R,5R,6R)-2-amino-3-(3,4-dichlorobenzyloxy)-6-fluorobicyclo[3.1.0]hexane-2,6-dicarboxylic acid 6-n-butyl ester
*⁴Compound 10 of the present invention: (1R,2R,3R,5R,6R)-2-amino-3-(3,4-dichlorobenzyloxy)-6-fluorobicyclo[3.1.0]hexane-2,6-dicarboxylic acid 6-benzyl ester
*⁵Compound B (the parent compound of compound 44 of the present invention): (1S,2R,3R,5R,6S)-2-amino-3-(3,4-dichlorobenzyloxy)-bicyclo[3.1.0]hexane-2,6-dicarboxylic acid
*⁶Compound 44 of the present invention: (1R,2R,3R,5R,6R)-2-amino-3-(3,4-dichlorobenzyloxy)-6-fluorobicyclo[3.1.0]hexane-2,6-dicarboxylic acid 6-(1-(cyclohexyloxycarbonyloxy)ethyl)ester

INDUSTRIAL APPLICABILITY

The compound of the present invention, a pharmaceutically acceptable salt thereof or a hydrate thereof may be employed as a prodrug of a metabotropic glutamate receptor antagonist, and thus can significantly increase the amount of exposure in vivo of the parent compound.

Therefore, the present invention makes it possible to provide a drug which is effective for the treatment and prevention of psychiatric disorders such as schizophrenia, anxiety and related ailments thereof, bipolar disorder and epilepsy; for the treatment and prevention of neurological diseases such as drug dependence, cognitive disorders, Alzheimer's disease, Huntington's chorea, Parkinson's disease, dyskinesia associated with muscular rigidity, cerebral ischemia, cerebral failure, myelopathy and head trauma; and for relieving convulsions, pain and nausea. The drug shows high activity in oral administration, which is preferable from the point of usability and medicinal benefits.

The invention claimed is:

1. A 2-amino-bicyclo[3.1.0]hexane-2,6-dicarboxylic ester compound, or a pharmaceutically acceptable salt thereof, represented by formula [I]

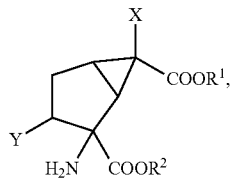

[I]

wherein, $R^1$ and $R^2$ are different, and when either one represents a hydrogen atom, the other is a group represented by formula [i]

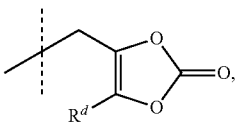

[i]

wherein $R^d$ represents a $C_{1-10}$alkyl group, a $C_{2-10}$alkenyl group or an aryl group; or, both $R^1$ and $R^2$ are represented by formula [i]

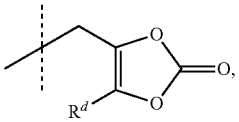

[i]

wherein $R^d$ is the same as described above;

X represents a fluorine atom; and

Y represents —OCHR$^3$R$^4$ wherein $R^3$ and $R^4$ are identical or different, and each represents a hydrogen atom, a $C_{1-10}$alkyl group, a $C_{2-10}$alkenyl group, a phenyl group, a naphthyl group, a naphthyl group substituted by one to seven halogen atoms, or a phenyl group substituted by one to five substituents selected from a group consisting of a halogen atom, a phenyl group, a $C_{1-10}$alkyl group, a $C_{1-10}$alkoxy group, a trifluoromethyl group, a hydroxycarbonyl group, an amino group, a nitro group, a cyano group and a phenoxy group.

2. A 2-amino-bicyclo[3.1.0]hexane-2,6-dicarboxylic ester compound, or a pharmaceutically acceptable salt thereof, represented by formula [II]

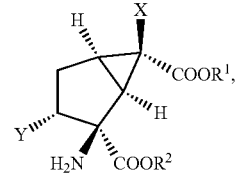

[II]

wherein, $R^1$ and $R^2$ are different, and when either one represents a hydrogen atom, the other is a group represented by formula [i]

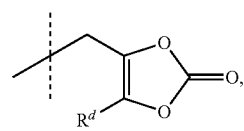

[i]

wherein $R^d$ represents a $C_{1-10}$alkyl group, a $C_{2-10}$alkenyl group or an aryl group; or, both $R^1$ and $R^2$ are represented by formula [i]

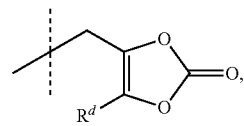

[i]

wherein $R^d$ is the same as described above;

X represents a fluorine atom; and

Y represents —OCHR$^3$R$^4$ wherein $R^3$ and $R^4$ are identical or different, and each represents a hydrogen atom, a $C_{1-10}$alkyl group, a $C_{2-10}$alkenyl group, a phenyl group, a naphthyl group, a naphthyl group substituted by one to seven halogen atoms, or a phenyl group substituted by one to five substituents selected from a group consisting of a halogen atom, a phenyl group, a $C_{1-10}$alkyl group, a $C_{1-10}$alkoxy group, a trifluoromethyl group, a hydroxycarbonyl group, an amino group, a nitro group, a cyano group and a phenoxy group.

3. A 2-amino-bicyclo[3.1.0]hexane-2,6-dicarboxylic ester compound, or a pharmaceutically acceptable salt thereof according to claim 2, wherein in the formula [II], $R^2$ represents a hydrogen atom; X represents a fluorine atom; Y represents —$OCHR^3R^4$ wherein $R^3$ and $R^4$ are the same as described above; and $R^1$ represents a group represented by formula [i]

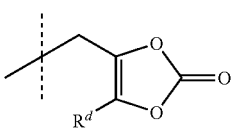

[i]

wherein $R^d$ represents a $C_{1-10}$alkyl group, a $C_{2-10}$alkenyl group or an aryl group.

4. A drug comprising the 2-amino-bicyclo[3.1.0]hexane-2,6-dicarboxylic ester compound, or the pharmaceutically acceptable salt thereof according claim 2 as an active ingredient.

5. A drug according to claim 4, wherein the drug is a group II metabotropic glutamate receptor antagonist.

6. A 2-amino-bicyclo[3.1.0]hexane-2,6-dicarboxylic ester compound represented by the following structure:

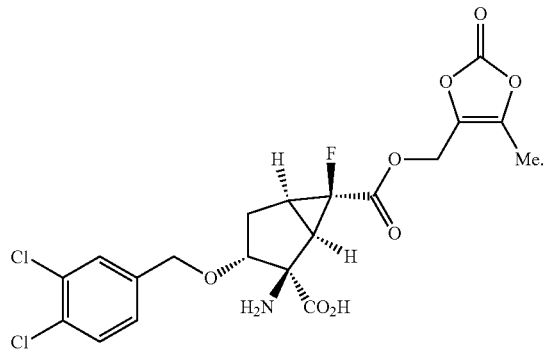

* * * * *